United States Patent
Huh et al.

(10) Patent No.: US 11,732,226 B2
(45) Date of Patent: Aug. 22, 2023

(54) DIGITAL FLUID TELEPORTATION, ADVANCED BIOLOGICAL VIRTUALIZATION, AND LARGE SCALE INTEGRATION OF ORGAN-ON-CHIPS AND MICROPHYSIOLOGICAL MODELS

(71) Applicant: The Trustees of the University of Pennsylvania, Philadelphia, PA (US)

(72) Inventors: Dongeun Huh, Villanova, PA (US); Andrei Georgescu, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 18/048,987

(22) Filed: Oct. 24, 2022

(65) Prior Publication Data

US 2023/0078827 A1    Mar. 16, 2023

Related U.S. Application Data

(63) Continuation of application No. PCT/US2021/028774, filed on Apr. 23, 2021.

(60) Provisional application No. 63/015,242, filed on Apr. 24, 2020.

(51) Int. Cl.
  *C12M 3/00*     (2006.01)
  *C12M 3/06*     (2006.01)
  *C12M 1/36*     (2006.01)

(52) U.S. Cl.
  CPC ............ *C12M 21/08* (2013.01); *C12M 23/16* (2013.01); *C12M 41/48* (2013.01)

(58) Field of Classification Search
  CPC ....... C12M 21/08; C12M 23/16; C12M 41/48
  See application file for complete search history.

(56) References Cited

U.S. PATENT DOCUMENTS

| | | |
|---|---|---|
| 6,867,048 B2 | 3/2005 | Kovacs |
| 8,003,378 B2 | 8/2011 | Wikswo et al. |
| 10,360,819 B2 | 7/2019 | Huh et al. |
| 10,633,623 B2 | 4/2020 | Huh et al. |
| 2004/0038420 A1 | 2/2004 | Gelbart et al. |

(Continued)

FOREIGN PATENT DOCUMENTS

| | | |
|---|---|---|
| WO | 2013/086486 A1 | 6/2013 |
| WO | 2019/036666 A1 | 2/2019 |

(Continued)

*Primary Examiner* — Michael L Hobbs
(74) *Attorney, Agent, or Firm* — BakerHostetler

(57) ABSTRACT

A microphysiological platform described herein includes a fluidic synthesizer with a first fluid input selectively coupleable to a source of a first input fluid solution and a second fluid input selectively coupleable to a source of a second input fluid solution. The fluidic synthesizer further includes a fluid output. The microphysiological platform further includes a fluid addressing system with a fluid input fluidically coupled to the fluidic synthesizer fluid output. The fluid addressing system further includes a first fluid output and a second fluid output. The microphysiological platform further includes a first microphysiological device with a fluid input fluidically coupled to the first fluid output of the fluid addressing system and a second microphysiological device with a fluid input fluidically coupled to the second fluid output of the fluid addressing system.

29 Claims, 35 Drawing Sheets

(56) References Cited

U.S. PATENT DOCUMENTS

| | | |
|---|---|---|
| 2010/0267142 A1 | 10/2010 | Wang et al. |
| 2012/0101268 A1 | 4/2012 | Elizarov et al. |
| 2018/0126037 A1 | 5/2018 | Huh et al. |
| 2018/0216058 A1 | 8/2018 | Huh et al. |
| 2018/0223251 A1 | 8/2018 | Huh et al. |
| 2018/0230415 A1 | 8/2018 | Huh et al. |
| 2018/0312810 A1 | 11/2018 | Huh et al. |
| 2020/0190456 A1 | 6/2020 | Huh et al. |

FOREIGN PATENT DOCUMENTS

| | | | |
|---|---|---|---|
| WO | WO-2019036666 A1 * | 2/2019 | ............ C12M 1/005 |
| WO | 2019/191111 A1 | 10/2019 | |
| WO | 2020/073043 A1 | 4/2020 | |

* cited by examiner

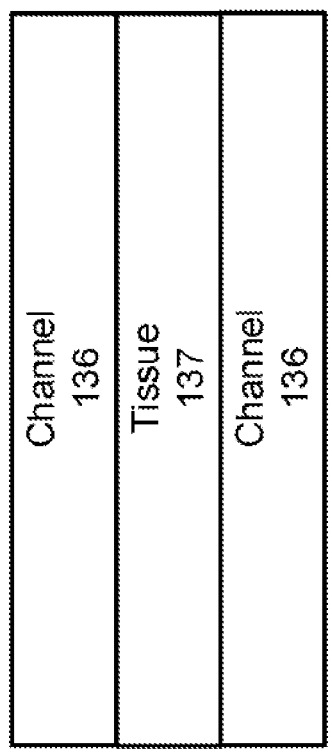
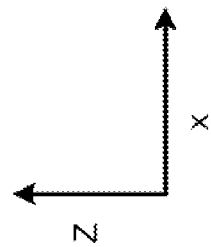
FIG. 5B

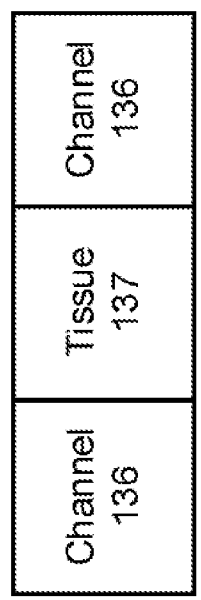
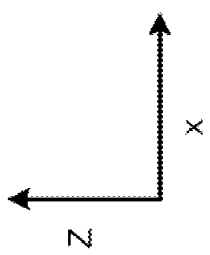
FIG. 5C

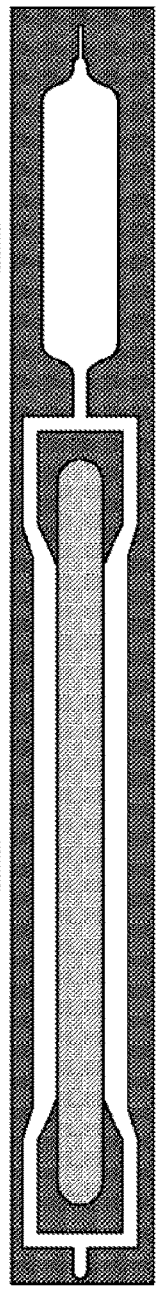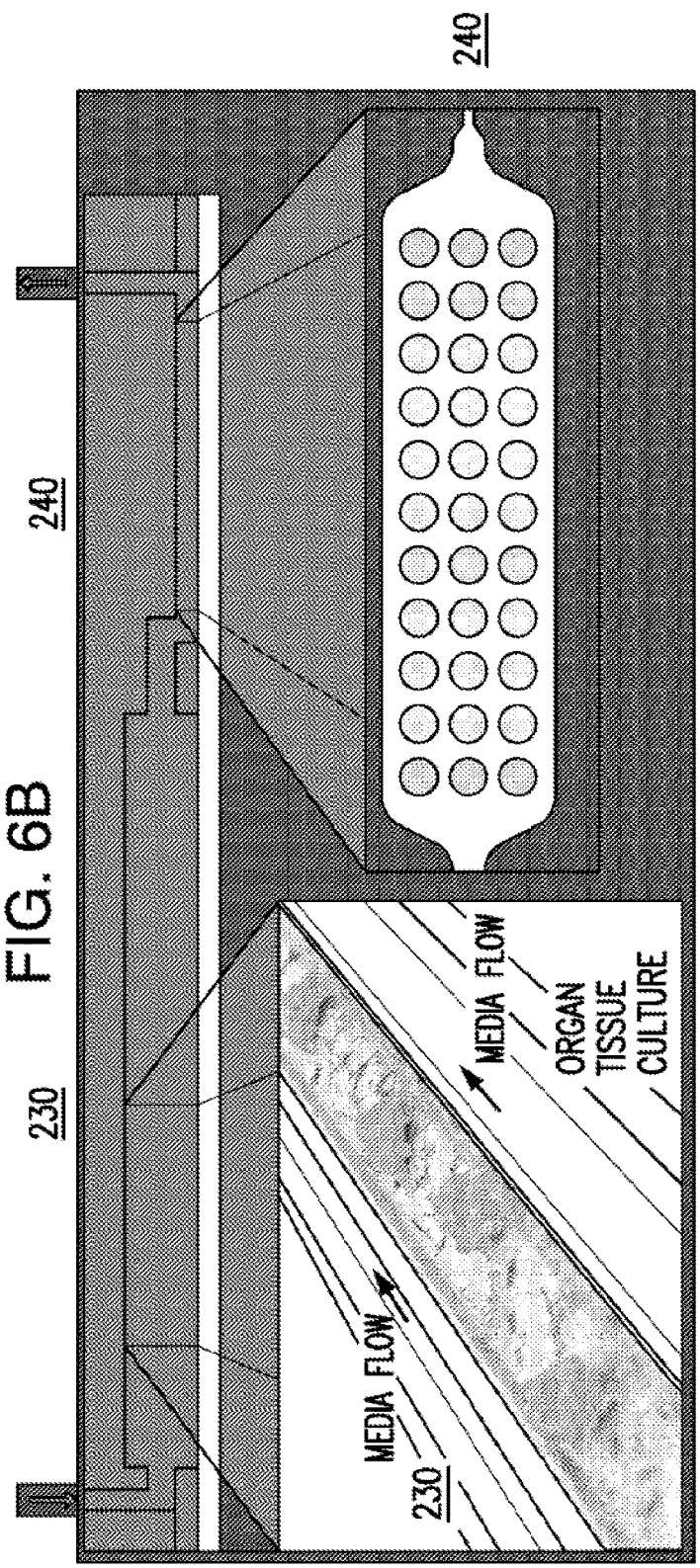

600

700

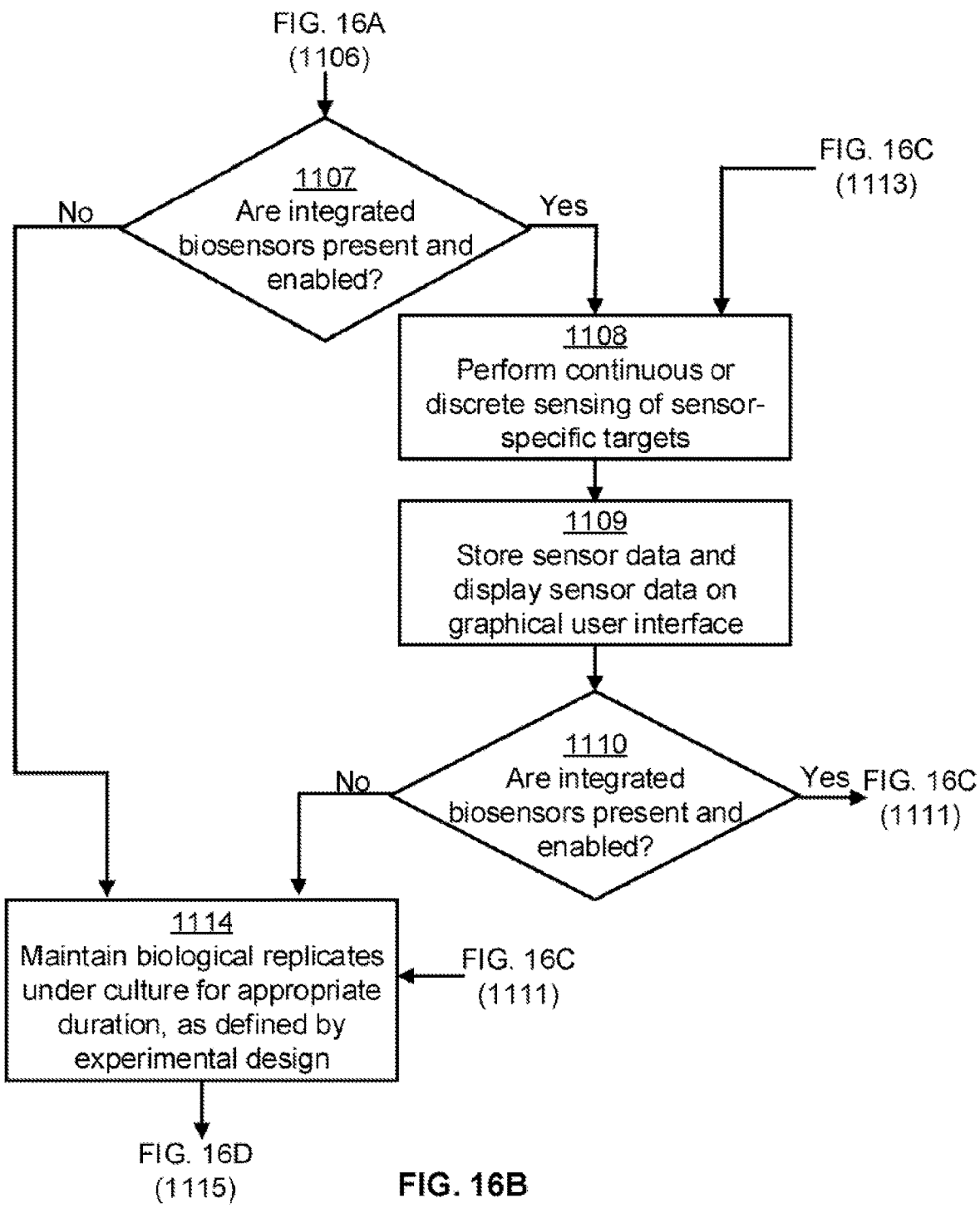

DIGITAL FLUID TELEPORTATION, ADVANCED BIOLOGICAL VIRTUALIZATION, AND LARGE SCALE INTEGRATION OF ORGAN-ON-CHIPS AND MICROPHYSIOLOGICAL MODELS

CROSS REFERENCE TO RELATED APPLICATIONS

This application is a bypass continuation application under 35 U.S.C. § 120 of International Application No. PCT/US2021/028774, filed on Apr. 23, 2021; which claims priority to and the benefit of U.S. Provisional Patent Application Ser. No. 63/015,242, filed on Apr. 24, 2020. Each of the foregoing applications is incorporated herein by reference in its entirety for any and all purposes.

BACKGROUND

Certain organ-on-chip devices can include a microengineered biological cell-culture compartment in which tissue- and organ-level elements of human physiology can be recapitulated. Cells implanted therein can be expected to behave and organize in a physiologically realistic and relevant manner, allowing accurate in vitro modeling of functional biological units of the organ system.

However, certain organ-chip systems fail to create functional and/or realistic multi-organ networks and thus are unable to recapitulate complex, physiological responses and multi-organ interactions at the systemic level. Each organ-chip can require a different composition of growth media that needs to be formulated with hormones, nutrients, and other molecules to mimic the native microenvironment of the tissues in that specific organ. Due to the different biochemical cues required by different cell types to maintain their differentiated functions in different organs, it can be difficult to produce one single universal media composition that can be carried between organ units and still support the appropriate differentiation and long-term maintenance of all these multiple organ units simultaneously.

Furthermore, the translation of organ-on-chip devices into practical screening platforms can face challenges in terms of the complexity of operating these devices. For example, fluids in certain organ-on-chip devices need to be driven either by bulky syringe pumps or manually by scientists with pipettes. This reduced throughput can limit the adoption of organ-on-chip models in the pharmaceutical industry because processes like drug-candidate screening rely on automated, large-quantity, and high-throughput testing.

Accordingly, there remains a need to improve the throughput and the efficiency of the organ-on-chip devices. There is also a need for improved organ-on-chip devices, which can permit certain transmissions of cell-released signaling molecules, including hormones, between organs or tissues while relegating certain growth media formulations that can define a certain tissue microenvironment solely to the organs for which they are intended.

SUMMARY

Embodiments described herein relate to microphysiological platforms and methods of producing the same. In some embodiments, a microphysiological platform can include a fluidic synthesizer with a first fluid input selectively coupleable to a source of a first input fluid solution and a second fluid input selectively coupleable to a source of a second input fluid solution. The fluidic synthesizer further includes a fluid output. The fluidic synthesizer creates an output solution by mixing first input fluid solution received from the first fluid input and second input fluid solution received from the second fluid input and discharges the output solution from the fluid output. The microphysiological platform further includes a fluid addressing system with a fluid input fluidically coupled to the fluidic synthesizer fluid output. The fluid addressing system further includes a first fluid output and a second fluid output. The fluid addressing system conveys output solution from the fluid addressing system fluid input to a selected one, or both, of the first fluid output and the second fluid output. The microphysiological platform further includes a first microphysiological device with a fluid input fluidically coupled to the first fluid output of the fluid addressing system and a second microphysiological device with a fluid input fluidically coupled to the second fluid output of the fluid addressing system. Each of the first microphysiological device and the second microphysiological device culture biological tissue and perfuse the biological tissue with the output solution from the fluidic synthesizer received at the fluid input of the respective microphysiological device via the fluid addressing system. In some embodiments, the fluidic synthesizer can have at least a third fluid input selectively coupleable to at least a source of at least a third input fluid solution and is further operable to create the output solution by mixing one or both of the first input fluid solution received from the first fluid input and the second input fluid solution received from the second fluid input with the at least a third input fluid solution received at the at least a third fluid input. In some embodiments, the fluidic synthesizer can include a mixing chamber fluidically coupled to the fluid inputs and to the fluid output of the fluidic synthesizer and mix the input fluid solutions to create the output solution.

BRIEF DESCRIPTION OF THE DRAWINGS

FIGS. 5A to 5C are each a schematic illustration of an embodiment of a microphysiological device that may be included in the microphysiological platform of FIG. 1. FIG. 5B is a schematic illustration of a microphysiological device in a horizontal configuration, and FIG. 5C is a schematic illustration of a microphysiological device in a vertical configuration.

FIG. 6A is a schematic top view, and FIG. 6B is a schematic side cross-sectional view of a microphysiological device and biosensor arrangement, according to an embodiment, FIG. 6C is an exemplary illustration of an organ tissue culture contained in the microphysiological device of FIGS. 6A and 6B, and FIG. 6D is a detailed, schematic top view of the biosensor of FIGS. 6A and 6B.

FIGS. 16A-16D are flow diagrams illustrating a method of a screen-backward mode of fluid transportation, according to an embodiment.

Figure 1:
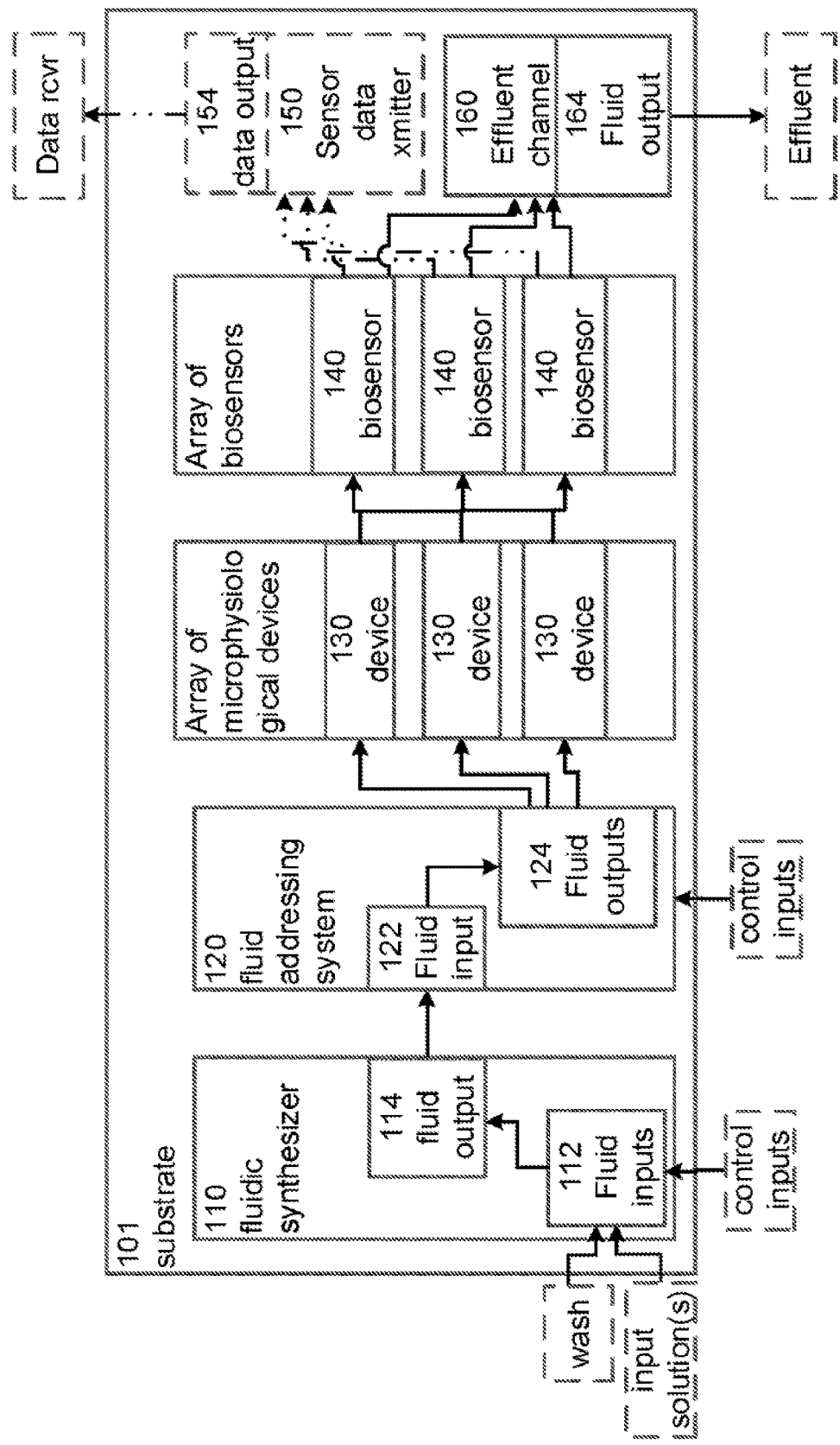
FIG. 1 is a schematic illustration of a microphysiological platform, according to an embodiment.

Throughout the figures, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments.

DETAILED DESCRIPTION

The disclosed subject matter provides systems and methods for one or a combination of integration, management, automation, analog interconnection, digital interconnection, maintenance, observation, analysis, or electronic control, of one or a plurality of microphysiological devices.

Techniques for producing a microphysiological platform including one or a plurality of microphysiological devices are disclosed herein. The disclosed subject matter can perform a fully or partially automated biological culture using the microphysiological devices without the need for specialized personnel. In certain embodiments, it can model the feed-forward and feed-back effects between biological systems or biological tissues modeled in a plurality of microphysiological devices, among which one or multiple subsets can be interconnected.

Microphysiological Platform and Control System Architecture

FIG. 1 is a schematic illustration of a microphysiological platform 100, according to an embodiment. As shown in FIG. 1, microphysiological platform 100 can include a fluidic synthesizer 110, a fluid addressing system 120, an array of microphysiological devices 130, an array of biosensors 140, a sensor data transmitter 150, and an effluent channel 160. Fluids can flow into platform 100, such as into fluid inputs 112 of fluidic synthesizer 110, through and between the components, and out of platform 100, such as out of fluid output 164 of effluent channel 160. Such fluids can include a wash fluid and one or more input solutions. As described in more detail below with reference to FIG. 3, multiple input solutions received at fluidic inputs 112 of fluidic synthesizer 110 can be mixed within fluidic synthesizer 110, in some embodiments under the control of control inputs received by fluidic synthesizer 110, and the resultant customized solution can be output from fluid output 114. Fluid output 114 is fluidically coupled to fluid input 122 of fluid addressing system 120. As described below with reference to FIG. 4, fluid addressing system 120 can route a discrete bolus, or continuous flow, of the output solution from fluid input 122 to a selected one of fluid outputs 124. The routing of the fluid can be controlled by control inputs received by fluid addressing system 120. Each fluid output 124 is fluidically connected to an input of a specific one of microphysiological devices 130 in the arm of microphysiological devices 130. As described in more detail below with reference to FIGS. 5A to 5C, each microphysiological device 130 may be implemented as an organ on a chip, and the solution delivered to the input of microphysiological device 130 can interact with the content of the device 130, and its composition changed before reaching the output of device 130. The output of device 130 is fluidically coupled to the input of one or more biosensors 140 in the array of biosensors 140, such that the bolus of modified fluid can be received by one or more of the biosensors 140. As described in more detail below in part with reference to FIGS. 6A to 6D, each biosensor 140 can detect or measure one or more properties of the modified solution, and can generate a data signal indicative of the one or more properties. In some embodiments, the generated sensor data can be communicated to a sensor data transmitter 150, which can transmit the sensor data through a data output 154 to be received by a data receiver separate from the microphysiological platform 100. In some embodiments, the generated sensor data can be read directly from the biosensors 140 (i.e., without the use of the sensor data transmitter 150). In other words, the generated sensor data can be read without the use of a data transmission system. Each biosensor 140 has a fluid output that is fluidically connected to an input of a effluent channel 160, such that the modified fluid can be conveyed from biosensor 140 to effluent channel 160, from which it can be discharged through fluid output 164 of effluent channel 160 to a effluent separate from the neurophysiological platform 100. In some embodiments, the fluid output 164 can be routed to recycle fluid. In some embodiments, the fluid output 164 can route fluid back to the fluid addressing system 120. In some embodiments, the fluid output 164 can route fluid back to the fluidic synthesizer 110. In some embodiments, the fluid output 164 can route fluid back to the array of microphysiological devices 130 in some embodiments, the fluid output 164 can undergo further processing prior to being re-integrated into the microphysiological platform 100.

In some embodiments, the fluidic synthesizer 110 can generate microliter quantities of a specified fluidic mixture to perform conditional or combinatorial screening on all or some of the microphysiological devices 130 in the microphysiological platform 100. In some embodiments, the fluidic synthesizer 110 can generate quantities ranging from less than nanoliter to more than one milliliter of a specified fluidic mixture. In some embodiments, the quantities generated of one or a plurality of fluid mixtures can depend on the requirements of a specific platform, an intended experiment, a biological system, or a combination thereof.

In some embodiments, the fluid addressing system 120 can be controlled manually, semi-automatically, or automatically to dynamically change which individual microphysiological devices or which subset of microphysiological devices is selected as outputs for delivery of an input fluid or fluids. In certain embodiments, the fluid addressing system 120 can include at least one valve that is configured to divert the flow of a fluidic mixture to a plurality of selected outputs or microphysiological devices 130.

In some embodiments, the fluidic synthesizer 110 can repeatedly produce the at least one target fluid mixture which can be delivered by the fluidic addressing system 120 to a plurality of microphysiological devices 130. In non-limiting embodiments, such operation can be cycled autonomously to create an automated microphysiological platform.

In some embodiments, the microphysiological platform 100 can include a first fluidic synthesizer 110 for creating a first fluidic mixture, a first fluid addressing system 120 for routing the first fluid mixture to all or a subset of at least one microphysiological device 130, and at least one microphysiological device 130 for incubating a biological tissue or material with the first fluidic mixture to generate a second fluidic mixture. For example, the second fluidic mixture can be generated by biochemical interaction between the first fluidic mixture and the first microphysiological device.

In some embodiments, the biologic tissue can include a lung tissue, a bone marrow tissue, a bone tissue, a pancreatic tissue, an endocrine islets tissue, a liver tissue, a kidney tissue, a placenta tissue, an eye tissue, an intestinal tissue, a bladder tissue, a brain tissue, a mouth tissue, a tongue tissue, a tooth tissue, a nose tissue, a thymus tissue, a lymph node tissue, a lymphatic system tissue, a throat tissue, or an combination thereof. In some embodiments, the biologic tissue can include a specific human tissue. In some embodiments, a specific human tissue can include one or more of a human organ, an organ subcomponent, a system of two or more organs, a system of a generic tissue element (e.g., blood vessel or a ligament), or a specific cell type (e.g., a fibroblast cell that might be engaging in behavior of interest such as creating fibrosis). In some embodiments, the biologic tissue can include a specific human tissue undergoing a specific routine behavior, a lung tissue that is cyclically breathing, a specific human tissue undergoing an atypical condition, a lung tissue undergoing an asthma attack, a specific human tissue undergoing a specific interaction with an outside agent, a lung tissue being infected with bacteria, a lung tissue exposed to environmental factors, a lung tissue exposed to pollution, a lung tissue exposed to corrosive gas, a specific human tissue undergoing a specific interaction with an outside agent that is intended for use as a therapeutic, a specific human tissue undergoing a specific interaction with a drug, a specific human tissue undergoing a specific interaction with a biological antibody, a specific human tissue undergoing a specific interaction with a cellular therapy, a lung tissue undergoing an asthma attack while being monitored for its interaction with a bronchodilator as therapy for asthma, or any combination thereof.

In some embodiments, the biosensors 140 can include at least one chemical sensor. In some embodiments, the at least one chemical sensor can be coupled to the at least one microphysiological device 130 for detecting target analytes in the second fluidic mixture. In some embodiments, the at least one chemical sensor can include a thin conductive film for generating a resonant plasmonic coupling with incident light, and at least one biorecognition molecule for binding to the at least one target analyte to create an SPR sensor. The thin film can be configured to induce a transducible disturbance or shift in said resonant coupling when the at least one biorecognition molecule binds to the target analyte. In non-limiting embodiments, the at least one multiplexed plasmonic biosensor can include a transducer for transmitting a measured target analyte data (e.g. name and concentration of target analyte) to an external receiver. In some embodiments, the microphysiological platform 100 can include at least one external receiver, which can be configured to monitor and/or process the measured target analyte data. In some embodiments, the at least one sensor can utilize at least one sensing modality in addition to the SPR chemical sensing.

Figure 2A:
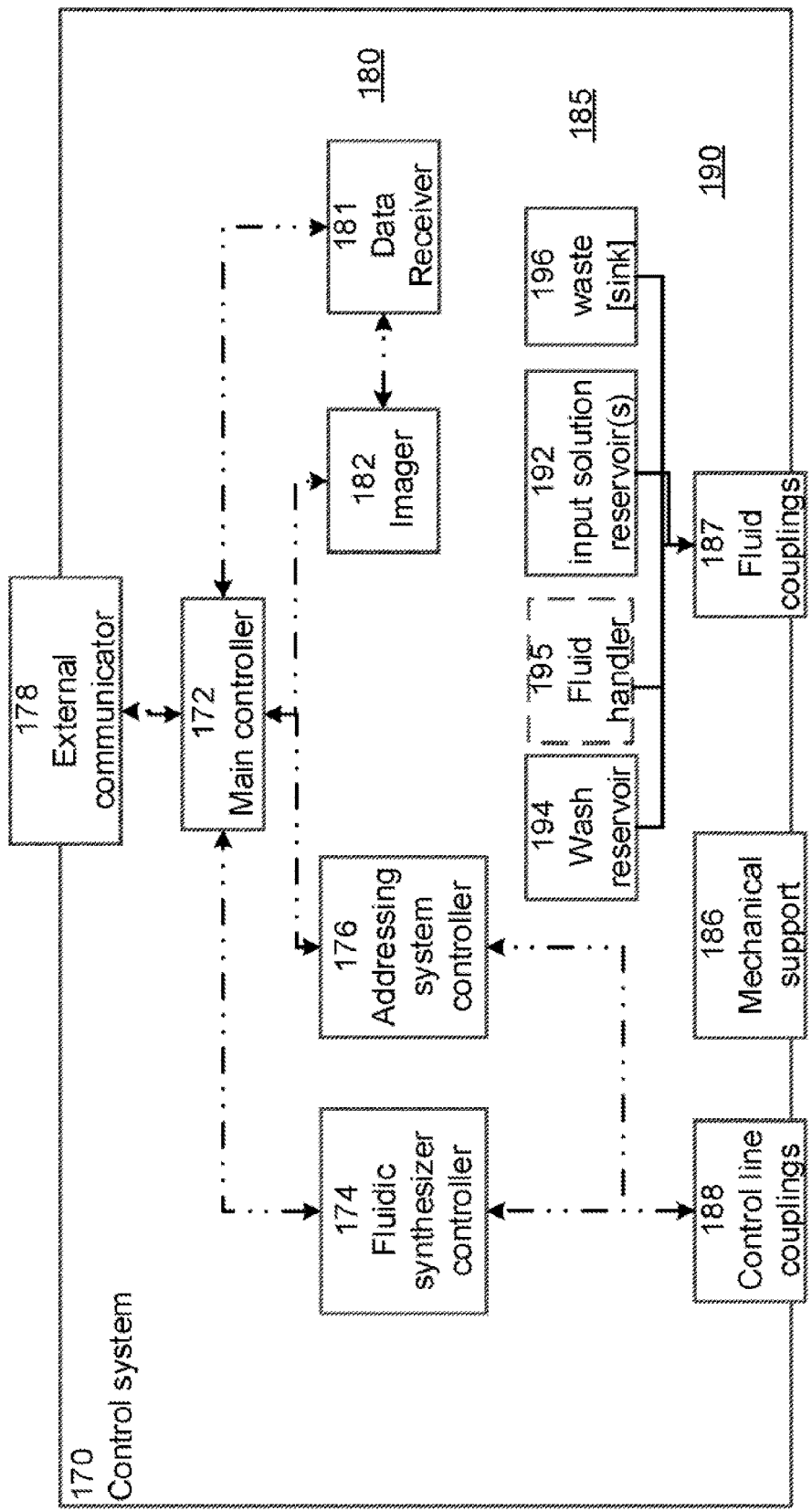
FIG. 2A is a schematic illustration of a control system and FIG. 2B is a schematic illustration of the microphysiological platform of FIG. 1 engaged with a control system, according to an embodiment.

Microphysiological platform 100 can be supported by, can receive fluid and control inputs from, and can provide data and fluid outputs to, a control system 170, shown schematically in FIG. 2A. As shown in FIG. 2A, control system 170 can include controllers, a data system 180, an engagement system 185, and a fluid system 190. Controllers can include a main controller 172, one or more fluid synthesizer controllers 174, one or more addressing system controllers 176, and an external communicator 178. Data system 180 can include an imager 182 and one or more sensor data receivers 181. Engagement system 185 can include a mechanical support 186, one or more fluid couplings 187, and one or more control line couplings 188. Fluid system 190 can include one or more input solution reservoirs 192, one or more wash solution reservoirs 194, one or more fluid handlers 195, and one or more effluent reservoirs 196.

For example, the control system 170 can include fluid reservoirs, such as a wash fluid reservoir 194 and reservoirs for input solutions for the fluidic synthesizer 110, and/or can provide fluid conduits to fluidically couple reservoirs external to the control system 170, to provide fluids to the respective inputs on the microphysiological platform 100. It can also provide a reservoir for fluid output 164 from the effluent channel 160 of the microphysiological platform 100, and/or can provide fluid conduit(s) to fluidically couple effluent reservoir(s) external to the control system 170. The control system 170 can also include one or more controllers, such a fluidic synthesizer controller 174 to control the operation of the fluidic synthesizer 110 (e.g. control application of pneumatic pressure to valves in the fluidic synthesizer 110), and an addressing system controller 176 to control the operation of the fluid addressing system 120 (e.g., via communication with valves in the fluid addressing system 120 to guide fluid flow). The control system 170 can include a data receiver 181 to receive sensor data provided by the sensor data transmitter(s) 150 associated with the biosensors. It can also include an imager 182 (such as a charge-coupled device, an active-pixel sensor, an optical microscope, a magnetic resonance imaging machine, a computed tomography machine, or a MOS field-effect transistor sensor) that can acquire image data from the microphysiological devices 130 and/or biosensors 140. The control system 170 can also include a main controller to receive data from the other controllers and components, and/or provide instructions thereto, and can communicate with other devices or systems external to the control system 170.

In some embodiments, the fluid handler 195 can selectively deliver fluid directly to desired locations on the microphysiological platform 100, including any one of the microphysiological devices 130 in the array of microphysiological devices 130. In other words, each of the microphysiological devices 130 can receive fluid from the fluid addressing system 120 as well as from the fluid handler 195. In some embodiments, the fluid handler 195 can include one or more micro injectors and/or one or more pipettes. In some embodiments, the fluid handler 195 can be movable, such that the fluid handler 195 can deliver fluid to a specified microphysiological device 130 among the array of microphysiological devices 130. This direct delivery can limit fluidic loss. For example, if fluid A is being delivered to a specified microphysiological device 130 and the user needs to deliver fluid B to the microphysiological device 130, the user can do so without flushing fluid A from the path in the fluid addressing system 120 and the fluidic synthesizer 110. This direct delivery capability can also be time-efficient, as the user does not need to take the time to flush the lines of fluid A before delivering fluid B to a desired site. In some embodiments, the fluid handler 195 can couple to the same ports on the microphysiological devices 130 as the fluid addressing system 120. In some embodiments, the fluid addressing system 120 can couple to a first port on a microphysiological device 130 and the fluid handler 195 can couple to a second port on the microphysiological device 130.

In some embodiments, the fluid handler 195 can deliver fluid to a location upstream of the microphysiological devices 130 (e.g., upstream of an interface between the fluid addressing system 120 and the microphysiological devices 130). In some embodiments, the fluid handler 195 can deliver fluid in-line to the microphysiological devices 130 in other words, a port can be integrated into a section of one or more microphysiological devices 130 for access by the fluid handler 195. In some embodiments, the fluid handler 136 can deliver fluid to a location downstream of the microphysiological devices 130. In some embodiments, each of the microphysiological devices 130 can include a valve for injection from the fluid handler 195.

In some embodiments, the fluid handler 195 can draw fluid from one or more of the microphysiological devices 130. In some embodiments, the fluid handler 195 can withdraw fluid from a location upstream of the microphysiological devices 130. In some embodiments, the fluid handler 195 can draw fluid from a location in-line to the microphysiological devices 130. In some embodiments, the fluid handler 195 can withdraw fluid from a location downstream of the microphysiological devices 130.

In some embodiments, the fluid handler 195 can deliver tissue, a tissue progenitor, stem cells, or any combination thereof to the microphysiological devices 130. In some embodiments, the fluid handler 195 can be used to develop tissue on site in the microphysiological devices 130. In some embodiments, tissue can be developed in the fluid handler 195.

In some embodiments, the fluid handler 195 can deliver or withdraw fluid from any portion of the microphysiological platform 100. In some embodiments, the fluid handler 195 can deliver fluid to the fluidic synthesizer 110 in some embodiments, the fluid handler 195 can withdraw fluid from the fluidic synthesizer 110 in some embodiments, the fluid handler 195 can deliver fluid to the fluid addressing system 120. In some embodiments, the fluid handler 195 can withdraw fluid from the fluid addressing system 120. In some embodiments, the fluid handler 195 can deliver fluid to the neurophysiological devices 130. In some embodiments, the fluid handler 195 can withdraw fluid from the microphysiological devices 130.

Figure 2B:
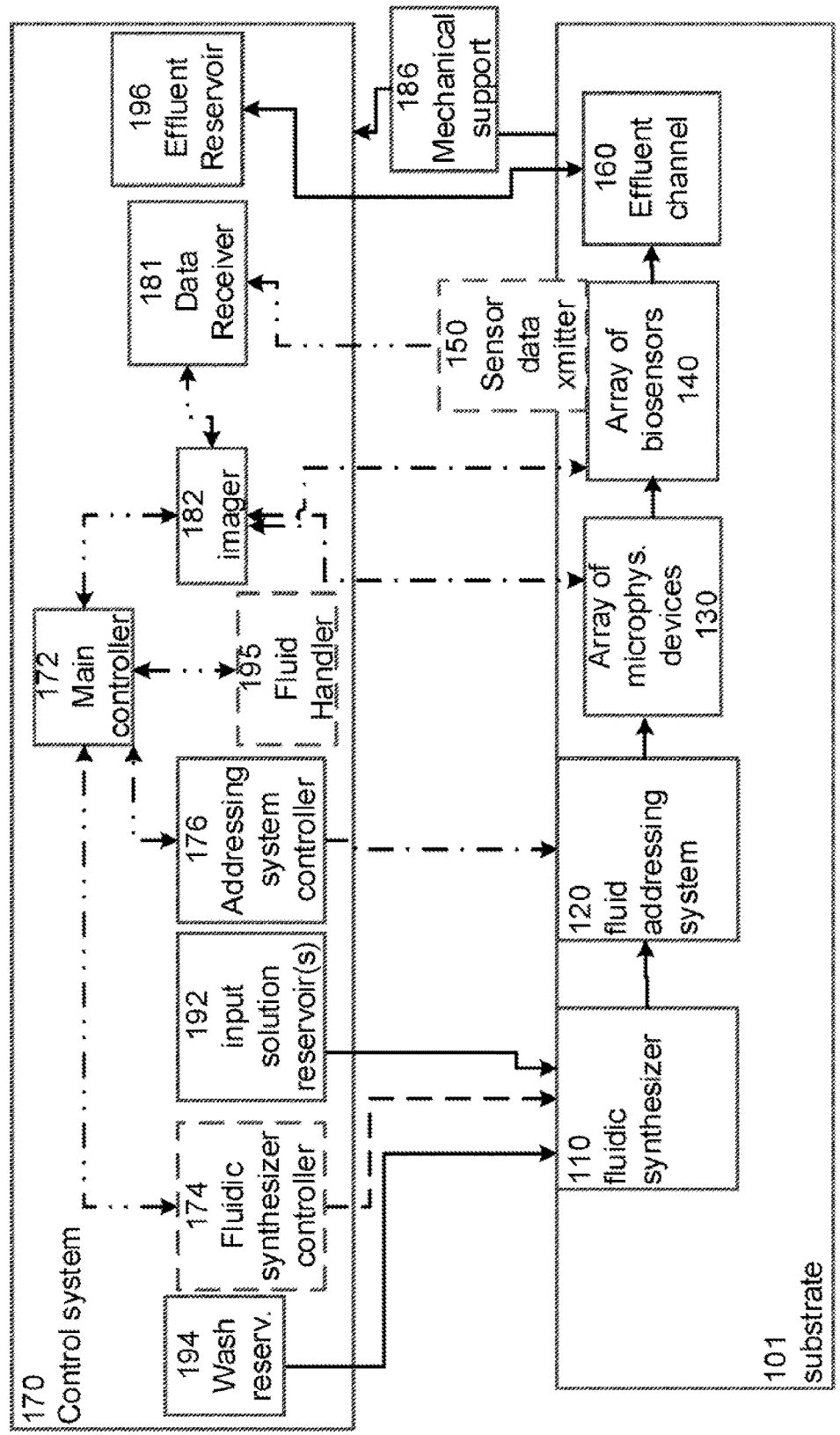

FIG. 2B is a schematic illustration of one microphysiological platform 100 engaged with control system 170. As shown, the mechanical support 186 positions the substrate 101 to be in contact with one or more of the components of the control system 170. In some embodiments, the mechanical support 186 can include a clamp to engage the substrate 101 and hold the substrate 101 in an operative relationship with one or more components of the control system 170. For example, the mechanical support 186 can support the substrate 101 in a read/write drive. In some embodiments, the mechanical support 186 can include structural components to hold the control line couplings 188 and the fluid couplings 187 in place. For example, the mechanical support 186 can include one or more platforms or clamps to hold the control line couplings 188 and the fluid couplings 187 in place. In some embodiments, the mechanical support 186 can act as, or include, a manifold for fluidic couplings (e.g., between the fluidic synthesizer 110 and the fluid addressing system 120). In some embodiments, the mechanical support 186 can align the substrate 101 with a known position. In some embodiments, the position of the substrate 101 can be constrained such that one or more fiduciary pins (not shown) on the mechanical support 186, whose position is known to the positioning systems in the fluid handler 195 and the imager 182, can act as a datum against which to reference the positions of different items. In some embodiments, these items can include tissues, targets of interest on the substrate 101, and/or the substrate 101 itself.

In some embodiments, the fluid couplings 187 can fluidically couple the wash reservoir 194, the input solution reservoir 192, and the effluent reservoir 196 to the fluidic synthesizer 110, the fluid addressing system 120, and the microphysiological devices 130. In some embodiments, the fluid couplings 187 can be established with inputs on the components of the microphysiological platform 100 (e.g., inputs into the fluidic synthesizer 110). In some embodiments, the fluid couplings 187 can be established with outputs from the microphysiological platform 100 (e.g., the outputs from the effluent channel 160). In some embodiments, the control line couplings 188 can be established with inputs on the components of the microphysiological platform 100 (e.g., inputs into the fluidic synthesizer 110). In some embodiments, the control line couplings 188 can be established with outputs from the microphysiological platform 100 (e.g., the outputs from the effluent channel 160).

In some embodiments, the data receiver 181 can establish communication with the sensor data transmitter 150. In some embodiments, the data receiver 181 can be operatively disposed to take passive readings from the biosensors 140.

In some embodiments, the imager 182 can be operatively disposed to image the components of the microphysiological platform. In some embodiments, the imager 182 can use light imaging techniques to detect fluids in various portions of the fluidic synthesizer 110, the fluid addressing system 120, and/or the microphysiological devices 130. In some embodiments, the imager 182 can be used to detect a type of cell or cell culture in the microphysiological devices 130 based on how light is absorbed, reflected, or scattered from the microphysiological devices 130.

In some embodiments, the main controller 172 can control the fluidic synthesizer controller 174, the addressing system controller 176, the data receiver 181, and the imager 182. In some embodiments, the fluidic synthesizer controller 174 can control the valve openings and the fluid flow rates into and/or out of the fluidic synthesizer 110 (i.e., the control line couplings 188). For example, the user can specify a specific mixture ratio and flow rate that the user wants to deliver to the fluid addressing system 120 via the fluidic synthesizer controller 174, and the appropriate valves can be opened and closed in the fluidic synthesizer 110 via the fluidic synthesizer controller 174.

In some embodiments, the addressing system controller 176 can control the valve openings and the fluid flow rates into and/or out of the fluid addressing system 120. In some embodiments, the addressing system controller 176 can control the opening and closing of valves between the fluid addressing system 120 and the microphysiological devices 130. In some embodiments, the addressing system controller 176 can control pressures in the fluid addressing system 120 and the microphysiological devices 130 via controlling the valves in the fluid addressing system 120.

In some embodiments, the fluidic synthesizer controller 174, the addressing system controller 176, the imager 182, and the data receiver 181 can be monitored and/or controlled via a single user interface (i.e., via the main controller 172). In some embodiments, the fluidic synthesizer controller 174, the addressing system controller 176, the imager 182, and the data receiver 181 can be monitored via separate user interfaces. In some embodiments, the main controller 172 can communicate data to the user via the external communicator 178.

Figure 20:
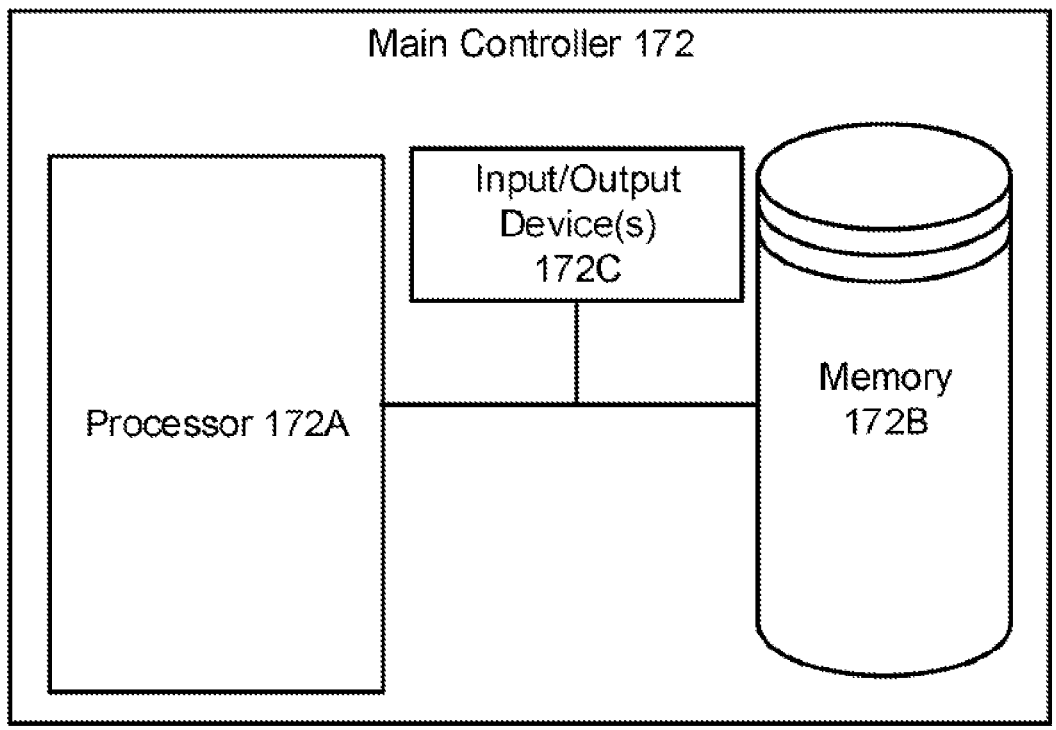
FIG. 20 is a schematic illustration of a controller, such as a main controller of a control system, according to an embodiment.

In some embodiments, the main controller 172, the fluidic synthesizer controller 174, and/or the addressing system controller 176 can include a proportional controller, an integral controller, a derivative controller, a proportional integral derivative (PID) controller, or any combination thereof. Any of the controllers described above can be implemented as general purpose compute device. For example, main controller 172 is shown schematically in FIG. 20, and can include a processor 172A, and memory 172B, and one or more input/output devices 172C. The processor 172A may be configured to receive, process, analyze, compile, store, and access data, e.g., through a network connection, as discussed in more detail herein, or through a physical connection with the device or storage medium (e.g., through Universal Serial Bus (USB) or any other type of port). Processor 172A may be any suitable processing device configured to run and/or execute a set of instructions or code and may include one or more data processors, image processors, graphics processing units, physics processing units, digital signal processors, and/or central processing units. Each processor 172A may be, for example, a general purpose processor, Field Programmable Gate Array (FPGA), an Application Specific Integrated Circuit (ASIC), and/or the like. Each processor 172A may be configured to run and/or execute application processes and/or other modules, processes and/or functions associated with the system and/or a network associated therewith. The underlying device technologies may be provided in a variety of component types (e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

Memory 172B may include a database (not shown) and may be, for example, a random access memory (RAM), a memory buffer, a hard drive, an erasable programmable read-only memory (EPROM), an electrically erasable read-only memory (EEPROM), a read-only memory (ROM). Flash memory, and the like. Memory 172B may store instructions to cause the processor to execute modules, processes, and/or functions associated with the communication device, such as patient data processing, sensor measurement, viral infection probability estimation, user device or patient monitoring control, authentication, encryption, and/or communication. Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes.

Examples of non-transitory computer-readable media include, but are not limited to, magnetic storage media such as hard disks, floppy disks, and magnetic tape, optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules, and hardware devices that are specially configured to store and execute program code, such as Application-Specific Integrated Circuits (ASICs), Programmable Logic Devices (PLDs). Read-Only Memory (ROM), and Random-Access Memory (RAM) devices. Other embodiments described herein relate to a computer program product, which may include, for example, the instructions and/or computer code disclosed herein.

Each input/output device 172C may be coupled with processor 172A and 172B and can be configured to communicate with other devices (such as other controllers and components of control system 170, other such control systems, and other devices, such as via external communicator 178). Each input/output device 172C may include a network interface configured to connect the compute device to another system (e.g., Internet, remote server, database) by wired or wireless connection. In some embodiments, the network interface may include a radiofrequency (RF) receiver, transmitter, and/or optical (e.g., infrared) receiver and transmitter configured to communicate with one or more devices and/or networks.

Microphysiological platform 100, and the components thereof, can be implemented on a chip or substrate 101. The substrate 101 can be manufactured through a cleanroom nanofabrication and/or a lithographic process similar to that used in the microprocessor fabrication industries. For example, when embedded into a single microfluidic substrate, the microphysiological platform can be fabricated by casting a thermoset polymer onto molds defined by negative photoresists, by hot embossing or stamping processes that can imprint the intended microfluidic patterns onto a thermoplastic material, and/or by injection molding. In certain embodiments, the platform can be fabricated from multiple bonded layers, which may be optically aligned, such as by utilizing complementary fiduciary markings. In certain embodiments, a platform fabricated from two or more layers can be bonded by the application of heat, by a dispensed adhesive, by the application of uncured thermoset plastic, including uncured polydimethylsiloxane (PDMS), which can subsequently cure to provide bonding force, and/or by the application of force in the direction of layer stratification for containing enclosed fluids or biological compounds with the resulting pressure-based seal. In some embodiments, the biosensors 140 can be integrated into the substrate 101. In some embodiments, the biosensors 140 can be located separate from the substrate 101, and/or may be external to the substrate 101. In some embodiments, the biosensors 140 can be integrated into a structure separate from the substrate 101.

In certain embodiments, the microphysiological platform 100 can include various geometric features. The geometric features can be patterned into the microphysiological platform to affect the flow path of liquid. For example, the geometric features can include one or a combination of the followings, selectively permeable membranes to restrict passage of some fluid compounds or phases and not others (e.g., selective gas or liquid permeability), porous membranes, notches, pillars, edges to manipulate liquid by capillary pinning or surface tension trapping, micropillar, nanopillar arrays, surface metal deposition, thin wall features to enable elastomeric actuation, molded or mechanically punched holes to transport fluid between bonded layers, matching geometric features to enable mechanical alignment of at least two layers of a multilayered device by optical overlay or mechanical conformal fit, arrows or indicators for the purpose of indicating to a user a location, port, or zone of interest, or fiduciary marks to assist autofocus, stitching, motion, or positional homing routines in imaging or automated analysis.

In some embodiments, microphysiological platform 10 can include a microfluidic system to which at least one inlet connection and at least one outlet connection can be formed. For example, as described in more detail below, an inlet connection can be a fluid input to fluidic synthesizer 110, a control input to fluid addressing system 120, a fluid input to a component on the microphysiological platform such as a microphysiological device 130, or a combination thereof. An outlet connection can be a waste output, a sampling output, or a combination thereof. The disclosed system can include an external compressor to generate regulated gas pressures. The gas pressures can drive fluid flow and gate the fluid addressing system 120, as described in more detail below.

Figure 3:
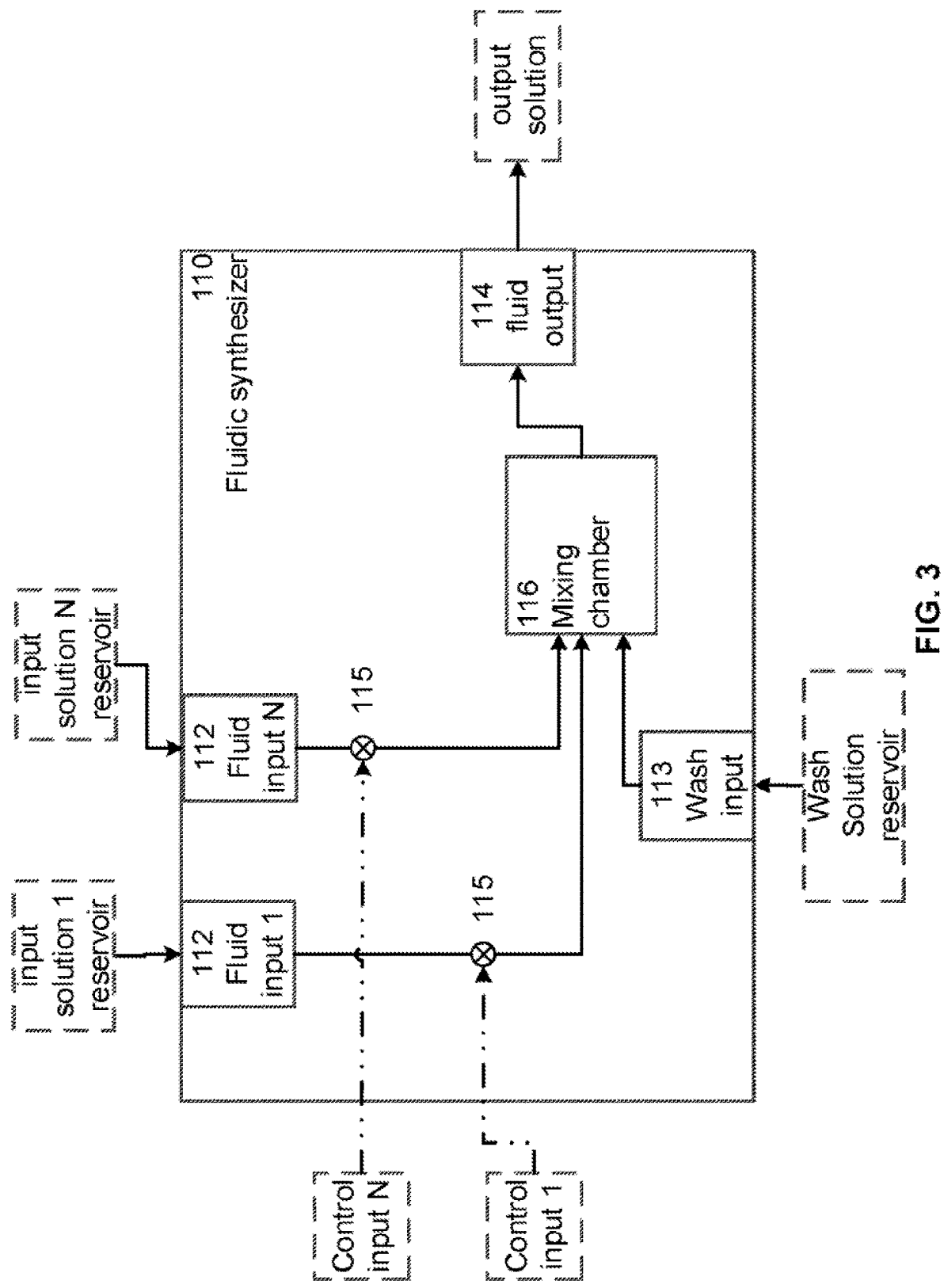
FIG. 3 is a schematic illustration of the fluidic synthesizer of the microphysiological platform of FIG. 1, according to an embodiment.

FIG. 3 is a schematic illustration of fluidic synthesizer 110. Fluidic synthesizer 110 can mix together two or more input solutions at individually specified ratios or proportions to create a custom fluid mixture, or output solution. As shown in FIG. 3, fluidic synthesizer 110 can include two or more fluid inputs 112, identified in FIG. 3 as fluid input 1 and fluid input N (where N can be 2 or more). In some embodiments, the fluid entering the fluidic synthesizer 110 via fluid input 1 can be the same as the fluid entering the fluidic synthesizer 110 via fluid input N or any of the other fluid inputs 112. In some embodiments, a first fluid can enter the fluidic synthesizer 110 via a first fluid input 112 and a second fluid can enter the fluidic synthesizer 110 via a second fluid input 112, the second fluid different from the first fluid. In some embodiments, many different fluids (e.g., at least about 3, at least about 4, at least about 5, at least about 6, at least about 7, at least about 8, at least about 9, at least about 10, at least about 20, at least about 30, at least about 40, at least about 50, at least about 60, at least about 70, at least about 80, at least about 90, or at least about 100) can enter the fluidic synthesizer 110 via the fluid inputs 112. Each fluid input 112 is fluidically connected (e.g. by any suitable fluid conduit or channel) to a mixing chamber 116. Each fluidic input can be selectively fluidically coupled to a respective reservoir of an input solution (not part of microphysiological platform 100, but optionally part of control system 170) to receive the input solution and convey it to mixing chamber 116. For example, a reservoir of input solution 1 is coupleable to fluid input 1, so that input solution 1 can be delivered via fluid input 1 to mixing chamber 116, and a reservoir of input solution N is coupleable to fluid input N, so that input solution N can be delivered by fluid input N to mixing chamber 116. A desired quantity (or flow rate) of input solution 1 and a desired quantity (or flow rate) of input solution N can thus be received in mixing chamber 116, and mixed together (e.g. passively or via an active mechanism such as an agitator) to form a desired quantity or bolus (or a flow rate), of an output solution mixing chamber 116 is fluidically coupled to fluid output 114 of fluidic synthesizer 110, from which the output solution (a discrete bolus, or a continuous flow at a desired flow rate) can be conveyed to downstream component(s), e.g., to one or more of the microphysiological devices 130, such as through fluid addressing system 120.

Wash input 113 is fluidically coupled to mixing chamber 116, and is selectively fluidically coupleable to a reservoir of wash solution (not part of microphysiological platform 100). After a desired quantity of output solution has been delivered from fluidic synthesizer 110 via fluid output 114, a quantity of wash solution can be conveyed to mixing chamber 116 via wash input 113, and can expel or clear the output solution from mixing chamber 116 through fluid output 114 and downstream components. In some embodiments, the mixing chamber 116 can include additional outlet streams (not shown) for expelling waste or recirculating fluid back into the fluidic synthesizer 110.

The quantity (or flow rate) of each input solution delivered via the respective fluid input 112 can be controlled by the input solution reservoir, e.g. by use of a pump controlling the flow of fluid from the reservoir, and/or a valve associated with the reservoir. Alternatively, the quantity (or flow rate) of any one of more of the input solutions delivered to mixing chamber 116 can be controlled by a separate mechanism, such as active valve included in the fluidic synthesizer 110. As shown in FIG. 3, the fluidic coupling between each fluid input 112 and mixing chamber 116 can include a valve 115. Valve 115 can be open, permitting flow of input solution to mixing chamber 116, or closed, preventing the flow of input solution. Each valve 115 can be controlled by a respective control input (not part of microphysiological platform 100), such as the fluidic synthesizer controller 174 included in the control system 170 as described above with reference to FIG. 2. In some embodiments, the valves 115 can include check valves, ball valves, globe valves, plug valves, needle valves, butterfly valves, pinch valves, gate valves, relief valves, or any combination thereof. In some embodiments, fluidic synthesizer 110 can be controlled by closed-loop control systems, including without limitation closed-loop fluidic control of flow rates by utilizing a feedback control loop (including, without limitation, a proportional-integral-derivative controller or "PID" controller) between one or a combination of a flow sensor, a pressure regulator, and a flow control valve.

Figure 4:
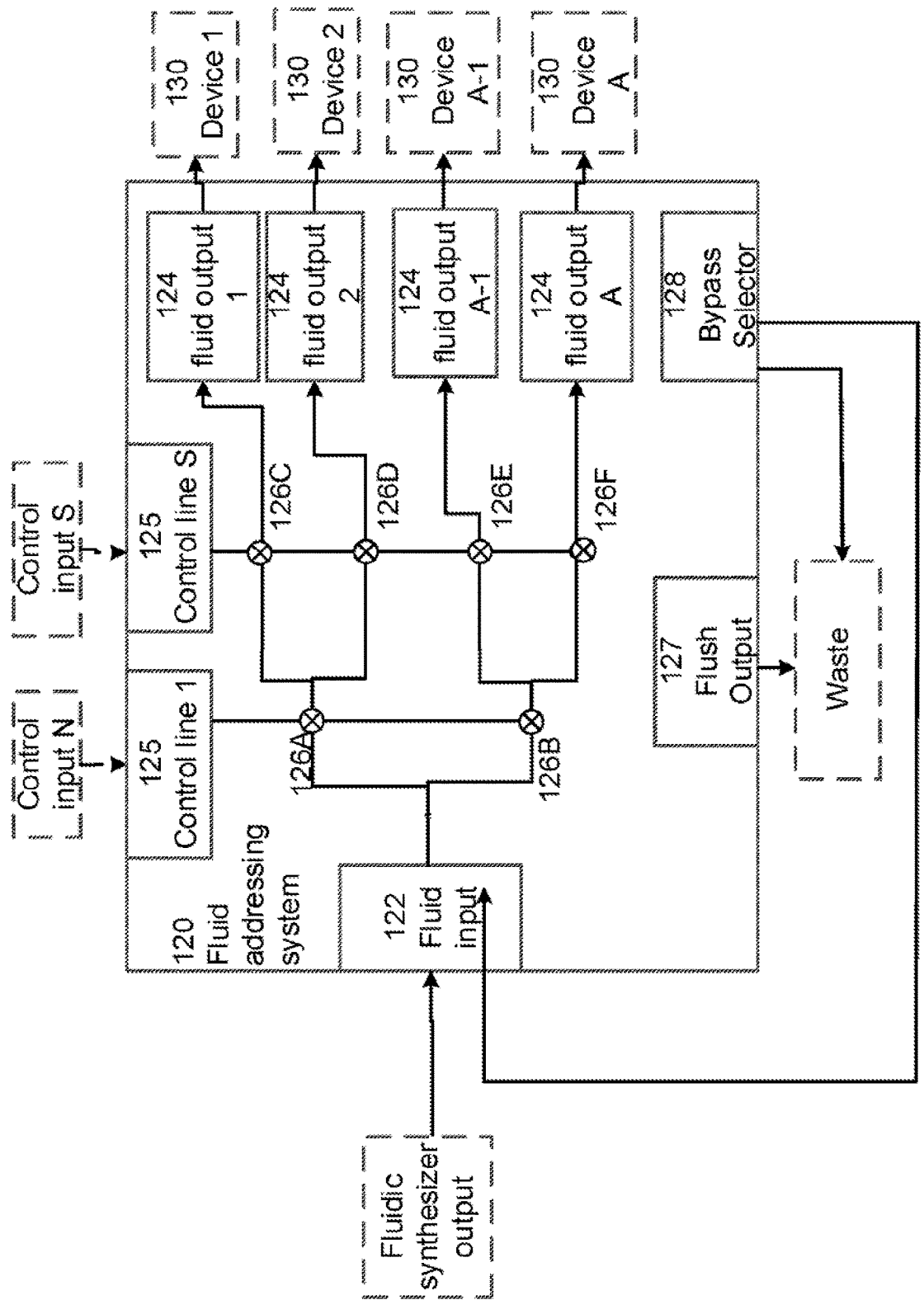
FIG. 4 is a schematic illustration of the fluid addressing system of the microphysiological platform of FIG. 1, according to an embodiment.

Fluid addressing system 120 is illustrated schematically in FIG. 4. Fluid addressing system 120 can route the output solution from the fluidic synthesizer 110 to a target location on microphysiological platform 100. For example, fluid addressing system 110 can divert the output solution to at least one microphysiological device 130. As shown in FIG. 4, fluid addressing system 120 can function as a demultiplexer component, to selectively route fluid (e.g., the output of fluid synthesizer 110) received at fluid input 122 to any one or more of multiple fluid outputs 124, under the control of control or select lines 125. The control lines 125 include control line 1, up to control line S. The control lines 125 control the valves 126A, 126B. 126C. 126D, 126E, 126F (collectively referred to as valves 126) to be open or closed. As shown, the valves 126 are arranged in pairs. As an example, the control lines 125 can include "high" lines and "low" lines, where the high lines control the first of each pair of valves 126 and the low lines control the second of each pair of valves 126. For example, control line 1 can include a high line and a low line. The high line of control line 1 can control valve 126A while the low line of control line 1 can control valve 126B. Control line S can include a high line that controls valve 126C and valve 126E as well as a low line that controls line 126D and line 126F. An advantage of such a system is the ability to control multiple valves with a single line. However, the open/closed status of some of the valves 126 would be coupled together. In other words, it would not be possible to control each of the valves 126 independently. For example valve 126C and valve 126E would have the same open/closed status, while valve 126D and valve 126F would have the same open/closed status. In some embodiments, one or more of the valves 126 can be a dome-shaped membrane valve connected to the at least one microphysiological device 130 through a rectangular-profile microchannel. In certain embodiments, one or more of the valves 126 can operated by positive pressure. In certain embodiments, one or more of the valves 126 can be operated by the application of a vacuum. In certain embodiments, one or more of the valves 126 can be operated by a combination of positive and negative pressure. In certain embodiments, one or more of the valves 126 can utilize rectangular profile microchannels.

In some embodiments, the fluid addressing system 120 may be implemented with a pneumatically gated or valved demultiplexer component to select output channels (fluid outputs 124). The demultiplexer can operate using binary addressing logic with integrated flow valves. For example, a "0" can symbolize a closed valve, and a "1" can symbolize an open valve. Each downstream microphysiological device 130 (or other devices) in the microphysiological platform can have a numeric address, whose binary representation can encode the valve states required to open the fluid addressing system output that corresponds to it. The binary addressing logic can be controlled by a plurality of pneumatic or hydraulic control or select lines 125. The mathematical relationship between the quantity of select lines (S) and the quantity of addresses (A) can be described by $A=2^S$. In some embodiments, two pneumatic or hydraulic connections can be used to control each select line, in which case the mathematical relationship between the quantity of select lines (S) and the quantity of addresses (A) can be described by $A=2^{S+1}$. For example, in an implementation in which the binary addressing logic has six select lines, there are 64 potential output addresses. Of course, the binary addressing logic can have fewer than six select lines, or it can have more than six select lines (e.g., 10 select lines to handle 1024 addresses). In some embodiments, each select line can be operated by an external 4-way valve, by two external 3-way valves, or two external 2-way valves. In non-limiting embodiments, the binary addressing system can include 7 total 2-way, 4-port solenoid valves as pilot valves (e.g., $2^7=128$ individually addressable fluid outputs or outputs from the fluid addressing system), or 14 total 2-way, 4-port solenoid valves as pilot valves (e.g., $2^{14}=16.384$ individually addressable fluid outputs or outputs from the fluid addressing system).

In some embodiments, the fluid addressing system can contain a "flush" output 127 to wash any liquid or dead volume currently contained in the fluid addressing system or downstream channels. In some embodiments, the flush output 127 can be fluidically coupled to the effluent channel 160, as described above with reference to FIG. 1. In some embodiments, the flush output 127 can be fluidically coupled to the fluid outputs 124. Fluid addressing system 120 provides great flexibility for operation of the microphysiological platform 100 and delivery of customized fluid and/or wash fluid to one, more than one, or all devices (such as microphysiological devices 130) downstream of fluid addressing system 120. For example, in some embodiments, fluid addressing system 120 can include an "off" state in which all outputs 124 are blocked. Fluid addressing system 120 can also open one of its fluid outputs 124, a subset of more than one of its fluid outputs 124, or all of its fluid outputs 124. In some embodiments, when the fluid addressing system 120 is delivering a fluid from its fluid input 122, the fluid addressing system 120 can simultaneously open all or a subset of the output channels connected to microphysiological devices requiring said fluid, and in doing so perfuse all of the selected microphysiological devices simultaneously.

Accordingly, the customized fluid mixture created by fluidic synthesizer 110 can be delivered to one or a plurality of microphysiological devices 130 by the fluid addressing system 120. Fluid addressing system 120 can open flow valves to the selected microphysiological device or devices 130, allowing the customized fluid mixture produced in the fluidic synthesizer 110 to flow into a target microphysiological device or devices 130 while preventing it from entering any other microphysiological device or devices 130.

In some embodiments, fluid addressing system 120 can include a bypass selector 128 that can control the flushing of all fluid upstream of a selected microphysiological device 130. For example, downstream of the most downstream select or control line 125 in the fluid addressing system 120, the fluid can continue directly to a target microphysiological device 130 or can be bypassed by the bypass selector 128 into a waste stream without disrupting the target microphysiological device 130. In other words, the bypass selector 128 can determine whether fluid output from the fluid addressing system 120 reaches its target location in the array of microphysiological devices 130 or if it switches to a waste stream and is flushed out. This reduces the amount of waste in the event that the user does not want to deliver the fluid currently in the fluid addressing system 120 into the microphysiological devices 130. With the bypass selector 128 only the fluid in the fluid addressing system 120 and upstream thereof would need to be flushed and go to an effluent or waste stream, rather than also including the fluid in the microphysiological devices 130 as well. The binary addressing logic can be used to minimize the requirement for solenoid valves to create a microphysiological platform 100 for high-throughput screening or testing on a multitude (e.g., hundreds to tens of thousands) of microphysiological devices 130. The microphysiological platform 100 can be an organ-on-a-chip system that can include at least one organ-on-a-chip.

In some embodiments, the fluid addressing system 120 can route the flow of a fluid to a different layer of microphysiological platform 100. In some embodiments, multiple layers of microphysiological platform 100 can alternate between rounded-profile or domed-profile microfluidic channels, which can be fabricated by photoresist-reflow molding, and square-profile or rectangular-profile microfluidic channels, which can be fabricated by negative-photoresist molding. Each of the rounded-profile, domed-profile, square-profile, and rectangular profile microfluidic channels can be located on the same layer or on different layers of microphysiological platform 100. Such alternating between the microfluidic channels can permit compatibility between membrane valves operating in rounded-profile microfluidic channels and microphysiological devices 130 operating in rectangular-profile microfluidic channels. In some embodiments, microphysiological platform 100 can include rectangular-profile microfluidic channels used in conjunction with dome-shaped valves. In some embodiments, the rectangular fluid lines or microfluidic channels can be decoupled from any swelling of pneumatically driven select lines or hydraulically driven select lines. The swelling can subject the pneumatic or hydraulic select lines to cross-sectional distortion when higher pressure is used to enable more complete and/or rapid membrane valve actuation. In some embodiments, a fluid stream can be transferred from a first flow layer to a second discrete valving layer ("out-of-plane" or "off-layer" valving) and then returned to the first flow layer within the fluid addressing system. The out-of-plane or off-layer valving can allow pneumatic or hydraulic control valves to be placed anywhere on the footprint of microphysiological platform 100. For example, the pneumatic or hydraulic control valves can be placed without unintended interference or pressurized deflection of fluid flow layers at locations other than those intended for valving purposes.

In some embodiments, fluids can flow between layers through holes (e.g., "vias"), which can be contiguous between the microfluidic channels present in opposing layers of the device. The placement of vias can be utilized to allow a first fluid channel to cross at least one second fluid channel without fluid contact by routing the first fluid channel on a first layer vertically to a second layer, then running the first fluid channel laterally across the second fluid channel and then vertically back to the first layer to create an overpass or underpass. In some embodiments, the vias can be utilized to transport fluid between a microchannel with a rectangular cross-section to a microchannel with a rounded cross-section. Pneumatically or hydraulically controlled membrane valves can be placed within the layers with rounded cross-sections, such that the actuated membrane can form a more robust seal along the rounded contour of the valved microchannel.

As described above with reference to FIG. 1, microphysiological platform 100 can include one or more arrays of microphysiological devices 130. Each such microphysiological device 130 can contain microengineered environments designed to stimulate physiologically relevant tissue or organotypic development. In some embodiments, all of the microphysiological devices 130 in the array, and/or on the entire microphysiological platform, can share the same generic design. In other embodiments, microphysiological devices 130 can have multiple designs and be distributed over different positions in an array, or in multiple arrays on microphysiological platform 10).

Each microphysiological device 130 in microphysiological platform 100 can be configured to contain, and can include, any one or more of tissues, cells, bacteria, viruses, other living entities, biological scaffolds, or explanted tissues, and can replicate the structure and function of an organ, or part thereof. In some embodiments, one or more of the microphysiological devices 130 can start as a bare structure. Thus, in an initial state of a microphysiological platform 100, it may be devoid of any biologic material, and neurophysiological devices 130 are configured to receive such material, and then to culture or grow it. Therefore, in other states of a microphysiological platform 100, it may contain biologic material in one or more microphysiological devices 130, in any one or more stages of physiological development. Thus, in some embodiments, one or more of the microphysiological devices 130 can be seeded with tissue by introducing cells that can be fed culture medium to grow into tissue or organs. Such cells can be introduced into the microphysiological device by am one or more of several routes. In some embodiments, cells can be introduced directly into the microphysiological device, e.g. by fluid handler 195. Alternatively, or in addition, cells can be introduced into any one or more other portions of microphysiological platform 100 that are fluidically coupled (or coupleable) to a microphysiological device 130, such as into, or upstream of, the fluidic synthesizer 110, into, or upstream of, the fluid addressing system 120, etc.

In some embodiments, the substrate 101 can include functionalized sites. In some embodiments, functionalized sites on the substrate 101 can be functionalized such that the cells can grow more easily. In some embodiments, the functionalized sites can be formed on the substrate 101 before the substrate 101 is enclosed to form the microphysiological device 130. In some embodiments, the functionalized sites can be formed in the microphysiological device 130 while the substrate 101 is inside an enclosure or "hive." In some embodiments, functionalized sites on the substrate 101 can be formed in a monolithic structure. In some embodiments, functionalized sites on the substrate 101 can be disaggregated across multiple components or structures.

In some embodiments, the cells can include heart cells, bone cells, kidney cells, liver cells, gut cells, lung cells, or any combination thereof. In some embodiments, the microphysiological devices 130 can be structured to simulate heart tissue, bone tissue, kidney tissue, liver tissue, gut tissue, lung tissue, or any combination thereof.

Figure 5A:
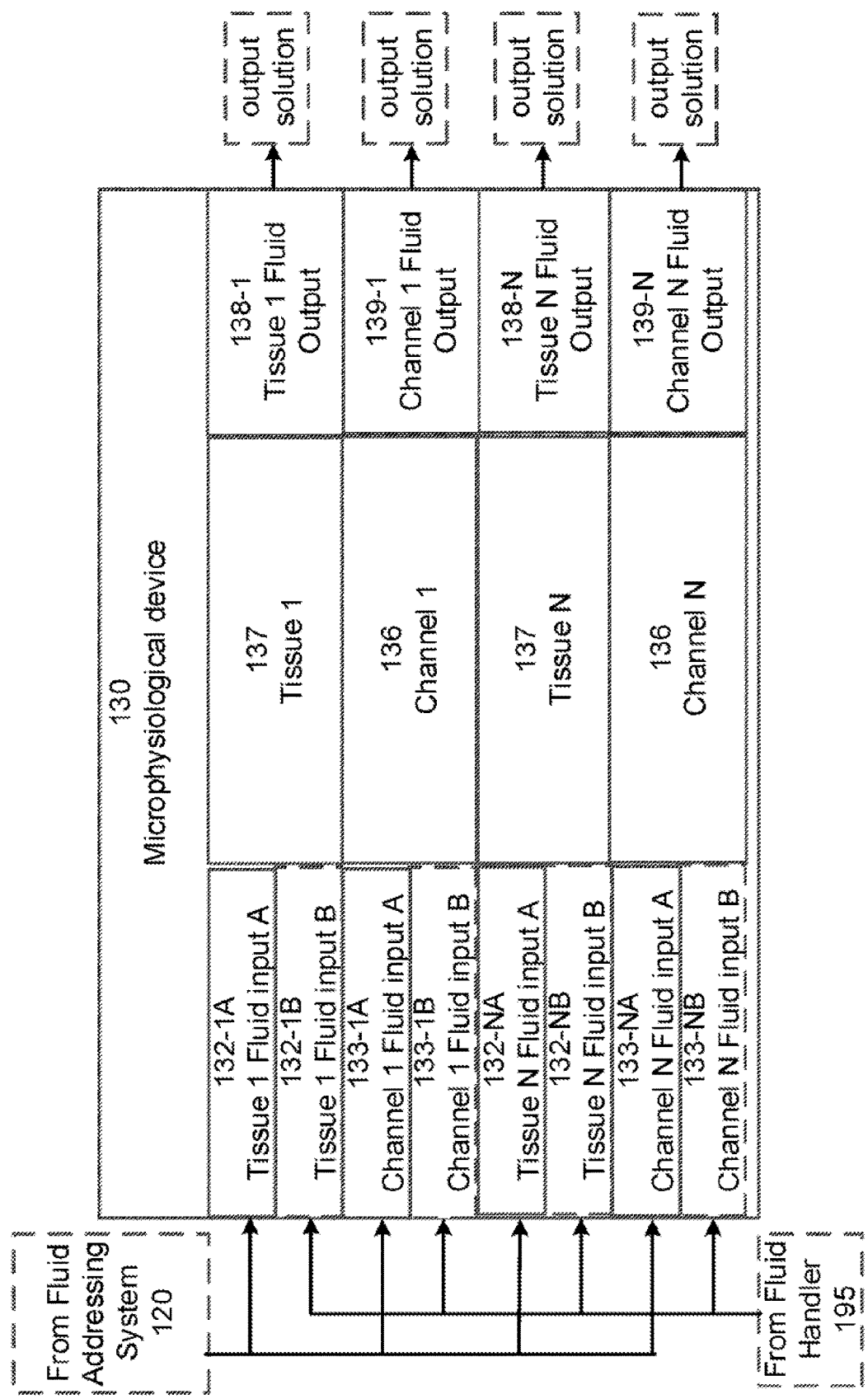

FIGS. 5A-SC are schematic illustrations of an embodiment of a microphysiological device 130 that may be included in the microphysiological platform 100 of FIG. 1. As shown, the microphysiological device 130 includes tissue chambers 137 interposed with channels 136. Each tissue chamber 137 can, in some states of microphysiological device 130 and microphysiological platform 100, contain cells, organ tissue cultures tissue, etc. (and thus tissue chamber 137 can also be referred to as tissue 137, as appropriate in the context). In some embodiments, the tissue chambers 137 can be in fluidic communication with the channels 136. In some embodiments, the tissue chambers 137 can include fluidic pathways, in which tissue cultures can grow. In some embodiments, fluid and/or nutrients can flow freely between the tissue chambers 137 and the channels 136. In some embodiments, the channels 136 can be used to deliver fluid to the tissue chambers 137 and/or tissue contained therein. In some embodiments, membranes can be placed between the tissue chambers 137 and the channels 136, or can be placed between two or more different tissue types within a tissue chamber 137. In some embodiments, the membranes can include semi-permeable membranes. In some embodiments, fluids in the tissues 137 and the channels 136 can be held in place by surface tension rather than membranes. In other words, there can be open fluidic communication between the channels 136 and the tissues 137.

As shown, the tissue chambers or tissues 137 include tissue chamber or tissue 1 up to tissue chamber or tissue N, while the channels 136 include channel 1 up to channel N, where N is an integer. In some embodiments, N can be 1, 2, 3, or more, up to any practical limit, and to meet the requirement for any desired organ-on-a-chip or other structure. In some embodiments, the microphysiological device 130 can include N tissues 137 and N−1 channels. In other words, the tissues 137 can be on the outer edges of the array of tissues 137 and channels 136 such that there is one less channel 136 than tissues 137. In some embodiments, the microphysiological device 130 can include N tissues 137 and N+1 channels 136. In other words, the channels 136 can be on the outer edges of the array of tissues 137 such that there is one less tissue 137 than channel 136.

As shown, tissue 1 includes tissue 1 fluid input A (132-4A) from the fluid addressing system 120 and optional tissue 1 fluid input B (132-1B) from the fluid handler 195, channel 1 includes channel 1 fluid input A (133-1A) from the fluid addressing system 120 and optional channel 1 fluid input B (133-1B) from the fluid handler 195, tissue N includes tissue N fluid input A (132-NA) from the fluid addressing system 120 and optional tissue N fluid input B (132-NB) from the fluid handler 195, and channel N includes channel N fluid input A (133-NA) from the fluid addressing system 120 and optional channel N fluid input B (133-NB) from channel N fluid input B. In some embodiments, the inputs (132-1A, 132-1B, 133-1A, 133-1B, 132-NA, 132-NB, 133-NA, 133-NB, collectively referred to herein after as inputs 132, 133) can include injection ports. In some embodiments, the inputs 132, 133 can include valves to regulate fluid flow.

As shown, tissue 1 includes tissue 1 fluid output 138-1, channel 1 includes channel 1 fluid output 139-1, tissue N includes tissue N fluid output 138-N, and channel N includes channel N fluid output 139-N. As shown each of the outputs (138-1, 139-1, 138-N, and 139-N, collectively referred to herein as outputs 138, 139), are configured to discharge an output solution, the composition of which is based on the composition of the fluid solution received from the fluid output of the fluidic synthesizer, via the fluid addressing system, at the respective fluid input to the channel, as may be affected, modified and/or supplemented by interaction of the fluid solution with any, tissue in the respective tissue chamber that is in fluidic communication with the respective channel. In some embodiments, the outputs 138, 139 can recycle the fluids exiting the tissues 137 and the channels 136. In some embodiments, the outputs 138, 139 can feed to waste streams. In some embodiments, the outputs 138, 139 can feed to further processing units. As described in more detail below, each tissue chamber 137 or channel 136 can include, or be fluidically coupled to, a separate sensor or set of sensors. FIG. 5B shows the tissue 137 and channels 136 oriented in a vertical configuration. In other words, the channels 136 are positioned above and below the tissue 137.

FIG. 5B includes axes, where the x-axis is horizontal and the z-axis is vertical. In FIG. 5B, fluid would flow horizontally through the tissue 137 and the channels 136. FIG. 5C shows the tissue 137 and the channels 136 oriented in a horizontal configuration. FIG. 5C includes axes, where the x-axis is horizontal and the z-axis is vertical. In FIG. 5C, fluid would flow vertically through the tissue 137 and the channels 136.

Each or any of the microphysiological devices 130 can be implemented as any of a non-limiting variety of organ-on-a-chip models, including an eye model (e.g., the model(s) disclosed in U.S. Pat. No. 10,360,819), a placenta model (e.g., the model(s) disclosed in U.S. Pat. No. 10,633,623), a lung model (e.g., the model(s) disclosed in U.S. Pat. Pub. Number 2018/0216058), an organ fibrosis model (e.g., the model(s) disclosed in U.S. Pat Pub. Number 2018/0230415), a cervix model (e.g., the model(s) disclosed in U.S. Pat. Pub. Number 2018-0312810), a vasculature model (e.g., the model(s) disclosed in WIPO Pub. Number 2019/191111), and/or a pulmonary airway model (e.g., the model(s) disclosed in WIPO Pub Number 2020/073043). Further, each or any of the microphysiological devices 130 can also include certain non-limiting features for organ-or-a-chip models, including a decellularized extracellular matrix (e.g., as disclosed in U S. Pat Pub. Number 2018/0126037), a heterobifunctional crosslinker (e.g., as disclosed in U.S. Pat Pub Number 2018/0223251), and/or a native extracellular matrix-derived membrane insert (e.g., as disclosed in U.S. Pat. Pub. Number 2020/0190456). The disclosure of each of the foregoing patents and published patent applications is incorporated herein by reference.

As described above with reference to FIG. 2, observations of the microphysiological devices 130, e.g., of the biological material, tissue, tissue structures, etc. contained therein, can be acquired by one or more imagers disposed in, associated with, and/or controlled by the control system. Imaging modalities or methods that may be implemented by such imagers can include optical microscopy, magnetic resonance imaging, or methods of computed tomography (CT) scanning. Correspondingly, the structure of each microphysiological device 130 from which image data is to be acquired should be configured to permit effective acquisition of images by the desired imaging modality. For example, optical microscopy requires that the structure of the microphysiological device 130, and any other structure of microphysiological platform 100 between the imager and the microphysiological device 130 be sufficiently transmissive of the light frequencies to be employed by the optical microscope, and that indices of refraction any different materials, and incident angles of light at interfaces thereof, enable adequate imaging. The data acquired from the use of one or a combination of said imaging methods on the contents of a microphysiological device 130 can be used for nonlimiting analytical purposes including one or a combination of the following: creating three-dimensional reconstructions of the biological entities in the microphysiological devices; applying computational measurement techniques to the acquired data to obtain phenotypic data about the biological specimen or entities: measuring the deviation of observed phenotype or physiology from the expected phenotype or physiology; or measuring dynamic behaviors of the observed biological entities over time, including, for purposes of illustration and not limitation, the rate of cell division, the formation of biological networks, or the development and function of biological tissues, organs, or functional subunits of organs.

Other sensor types can include an electronic sensor that monitors secondary or derived data (e.g., software reconstructions or models of biological or physical entities), or combinations thereof.

In addition to information gathered from sensors, such as the imagers described above, that are not part of the microphysiological platform 100, information about the contents of each microphysiological device 130 can also be gathered with one or more sensors coupled to or incorporated into microphysiological platform 100. Such sensors can be incorporated, in whole or in part, in the microphysiological device 130, and/or can be incorporated, in whole or in part, in one or more biosensors 140 that may be operatively. e.g., fluidically, coupled (continuously or selectively) with the fluid output 134 of the microphysiological device 13o. The sensor(s) can be placed locally to, downstream of, or upstream of each microphysiological device 130.

In some embodiments, microphysiological device 130 can include at least one integrated sensor, which can include a chemical sensor, a mechanical sensor, an optical sensor, or combinations thereof. In some embodiments, the integrated sensor can be incorporated in-line with one or more of the microphysiological devices 130. The at least one sensor can transduce one or a combination of signals. The signals can be originated from the microphysiological device, the periphery of the microphysiological device, an experimental factor or condition associated with the microphysiological device/platform, or combinations thereof.

In some embodiments in which the sensor is a chemical sensor, whether integrated with or placed downstream of microphysiological device 130, the sensor or sensors can transduce chemical signals. Such chemical signals can include the presence and concentration of biological secretions (e.g., hormones, paracrine factors, extracellular matrix components, metabolic byproducts), a biological consumption or uptake or modification of a chemical substrate (e.g., a consumption, uptake, or modification of nutrients, glucose, amino acids, biological therapeutics, drugs, drug products, toxins, gases, dissolved solids, dissolved chemical compounds, or aerosolized compounds), a fluid's pH, a fluid's osmolarity, a fluid's chemical composition (name and concentration of chemical constituents), multiplexed chemical sensing of a plurality of chemical targets (e.g., tens or hundreds of proteins by competitive binding against a dotted antibody microarray), environmental gas compositions, or combinations thereof. In non-limiting embodiments, the biological consumption or uptake or modification of a chemical substrate can be determined by measuring a downstream concentration of fluid effluent from a microphysiological device 130 against a concentration in fluid upstream of microphysiological device 130.

In some embodiments in which the sensor is a mechanical sensor, whether integrated with or placed downstream of microphysiological device 130, the sensor or sensors can transduce mechanical signals including an exertion of mechanical force or forces by microphysiological device 130 (e.g., a contraction of muscle tissue or pressure imposed by a modeled tumor's growth), application of mechanical force or forces onto microphysiological device 130 (e.g., closed-loop pressure control or closed-loop electromechanical actuation), ambient pressure, material properties (e.g., a modulus of elasticity, a shear modulus, and cyclic loading characteristics), or combinations thereof.

In some embodiments in which the sensor is an optical sensor, whether integrated with or placed downstream of microphysiological device 130, the sensor or sensors can transduce optical signals including images acquired by methods of light transmission microscopy, images acquired by fluorescent microscopy (e.g., confocal microscopy, light-sheet microscopy, and super-resolution microscopy), quantitative optical measurements (e.g., transmittance, luminescence, electrochemiluminescence, fluorescence, and fluorescence resonance energy transfer (FRET) techniques), phenotypic observations, observations of morphology and physiology in 3D computer reconstructions or reprojections, images of structural motifs (e.g., scaffold-tagged fluorescent markers, embedded quantum dots, and second harmonic generation (SHG) imaging) or combinations thereof.

In some embodiments, microphysiological device 130 can contain a combination of chemical sensors, mechanical sensors, optical sensors, and modality-specific sensing methods. In non-limiting embodiments, additional sensor modalities can be integrated or applied. The additional sensor modalities can include magnetic resonance. X-ray transmission, computed tomography, electronic monitoring of a software reconstruction, software reconstructions of a microphysiological device, or combinations thereof. In some embodiments, a microphysiological device can include one or a plurality of surface plasmon resonance (SPR) biosensors against one or a plurality of corresponding target analytes, alone or in conjunction with one or a combination of the sensors previously listed.

When any fluids can be delivered to microphysiological device 130, an equal volume of the existing fluids can be displaced over the sensor itself, over the area to which a sensor is sensitive, or into the volume to which a sensor is sensitive, which can lie downstream of microphysiological device 130, e.g., as part of a biosensor 140.

As shown schematically in FIG. 1, microphysiological platform 100 can include an array of biosensors 140, and the biosensors 140 can be fluidically coupled to microphysiological devices 130. The fluidic coupling arrangement can be implemented in different ways. For example, a microphysiological device 130 can have a single biosensor 140 with a dedicated fluidic coupling therebetween, i.e. the biosensor 140 can only sense properties of fluid output from the device 130. In some implementations, the relationship between microphysiological devices 130 and biosensor 140 can be one-to-many (multiple biosensors can be fluidically coupled, or coupleable, to a single microfluidic device 130), many-to-one (a single biosensor can be fluidically coupled, or coupleable, to multiple microfluidic devices 130), or many-to-many, using appropriate microfluidic couple, switching, multiplexing, demultiplexing, etc., arrangements, as represented schematically in FIG. 1 in the fluid paths between the array of microphysiological devices 130 and the array of biosensors 140. Any or all of these relationships between microphysiological devices 130 and biosensors 140 can be used on a single microphysiological platform 100. Correspondingly, microphysiological platform 100 can include multiple types of biosensors 140. For example, microphysiological platform 100 can include multiplexed biosensors, which can be electrochemical biosensors, optical biosensors, and/or fluorescence biosensors. The types of biosensors 140 patterned adjacent to microphysiological devices 130 in microphysiological platform 100 can differ. For example, a first microphysiological device 130 can be coupled with an optical fluorescence-based biosensor 140, a second microphysiological device 130 can be coupled with a pH sensor 140, and a third microphysiological device 130 can be coupled with a trans-epithelial electrical resistance (TEER) sensor 140. In some embodiments, a first microphysiological device 130 can have a first combination of sensor modalities that is different from a second combination of sensor modalities associated with a second microphysiological device 130. For example, the variability in combinations of sensor modalities or variability in sensor targets can exist between microphysiological devices 130 that are contained within the same microphysiological platform 100.

In some embodiments, a biosensor 140 can be implemented as, for example, a label-free microfluidic biosensor, and can be either co-localized with or located downstream of a microphysiological device 130. In some embodiments, a continuous acquisition from a plasmonic biosensor multiplexed for multiple biological target analytes can allow the real-time characterization of the microenvironment and secretome of the microphysiological device 130 with high temporal resolution and avoid the cost of label-based biosensors, whose cost of operation (primarily the consumption of labeled molecules) scales with operational duration. One example of such an implementation is microphysiological device 230 and biosensor 240 shown in FIGS. 6A to 6D. In this embodiment, a surface plasmon resonance (SPR)-based biosensor 240 is disposed in close proximity to microphysiological device 230 for continuous monitoring of target analytes in the fluid flowing through the organ-chip environment. In some embodiments, the biosensor 240 can be placed downstream of the microphysiological device 230. In some embodiments, the biosensor 240 can make measurements in-line with the microphysiological device 230. In some embodiments, the biosensor 240 can be integrated into the microphysiological device 230. In some embodiments, the biosensor 240 can include a colorimetric based sensor. In some embodiments, the biosensor 240 can include a fluorescence based sensor. In some embodiments, the biosensor 240 can be transduced by a microscope. In some embodiments, the biosensor 240 can be electric (e.g., cyclic voltammetry). In some embodiments, the biosensor 240 can be transduced by a potentiostat. In some embodiments, the microphysiological device 230 can include two inlets integrated into the microphysiological device 230. As described above with reference to FIG. 5B and FIG. 5C, the inlets can be oriented on top and on bottom of the microphysiological device 230. In some embodiments, the inlets can be oriented on either side of the microphysiological device 230.

In some embodiments, a multiplexed biosensor 140 can include a thin film and biorecognition molecules. The thin film can be deposited on the biosensor 140 through a physical vapor deposition technique. For example, physical vapor deposition of a gold thin-film can be used to generate the resonant plasmonic coupling with laser emission at a specific, tightly controlled wavelength and critical incident angle. The surface can be spotted with biorecognition molecules (e.g., antibodies. DNA, RNA, XNA, etc.) that can be selective to the biomolecules of interest in a solution. Binding of the molecules-of-interest to the biorecognition elements adsorbed to the gold surface can produce surface loading, the extent of which corresponds to a shift in the critical angle at which the resonant coupling can occur. By tracking this angle for each of the spots or by using a camera to image them all at once, the concentration of each analyte of interest in the solution can be measured without any additional labels being required. The biosensor 140 can be a label-free biosensor that can avoid the detrimental effects of the possible labeling-molecule toxicity to tissue culture. In some embodiments, biosensor 140 can include multiple biorecognition elements that can detect more than one target analyte at the same time.

In certain embodiments, the biosensor 140 can be integrated into at least one microphysiological device 130 to permit on-chip, real-time, and high content data acquisition with reduced sample volume requirements. The biosensor 140 can automatically sample a fluid content in microphysiological devices 130 and quantify target analytes in real-time. Similar to a barcode reader, for example, the biosensor 140 and an optical transducer can sample and quantify a fluid content using a laser beam reflection as it scans across the backside of the SPR spots. Accordingly, the biosensors 130 with the SPR can have more improved data-capture dimensionality than ELISA and microscopy analyses.

In certain embodiments, biochemical, electrochemical/electrochemiluminescent, mechanical, or/and optical biosensing schemes can be incorporated into microphysiological platform 100 through the modification of the components of biosensor 140 or their on-chip placement. For example, given that the multiplexed biosensor zones can utilize a patterned gold deposition on glass. Various biosensing schemes can be incorporated into the same gold pattern layer without additional fabrication processes. For example, a series of interdigitated microelectrode arrays for redox coupling-based electrochemical biosensing can be achieved through the disclosed technique.

In some embodiments, the measurements or readouts produced by a biosensor 140 can be used for chemical or biological characterization of the biological entities being cultured or experimented within a microphysiological device 130. This chemical or biological characterization can be based the appearance, disappearance, or change of a concentration of one or more compounds. For example, the compound can include chemical or biological compounds, chemical or biological moieties, dissolved compounds, biologically secreted compounds, metabolized or altered compounds, target analytes, or combinations thereof. In some embodiments, this characterization can be made as a comparison between the composition of a solution at a first location upstream of a microphysiological device 130 and the composition of the solution at a second location downstream of the microphysiological device 130. In some embodiments, this measurement can be used to infer, measure, or deduce one or a combination of characterizing observations or factors about the microphysiological device 130. For example, the observations can include (1) the uptake of compounds, chemicals, drugs, or biological agents from the solution into the biological entities in a microphysiological device 130; (2) the uptake of complex biological entities, including extracellular vesicles, exosomes, viral particles, constituents of an extracellular matrix, polymers, enzymes, nucleic acids, peptides, or proteins into the biological entities in a microphysiological device 130; (3) the secretion of compounds, chemicals, or biological agents from the biological entities in a microphysiological device 130 into the surrounding fluid solution; (4) the secretion of complex biological entities, including extracellular vesicles, exosomes, viral particles, constituents of an extracellular matrix, polymers, enzymes, nucleic acids, peptides, or proteins from the biological entities in a microphysiological device into the surrounding fluid solution; (5) the modification of compounds, chemicals, drugs, or biological agents in the solution by the biological entities in a microphysiological device 130, or (6) the modification of complex biological entities, including extracellular vesicles, exosomes, viral particles, constituents of an extracellular matrix, polymers, enzymes, nucleic acids, peptides, or proteins by the biological entities in a microphysiological device 130.

Figure 7A:
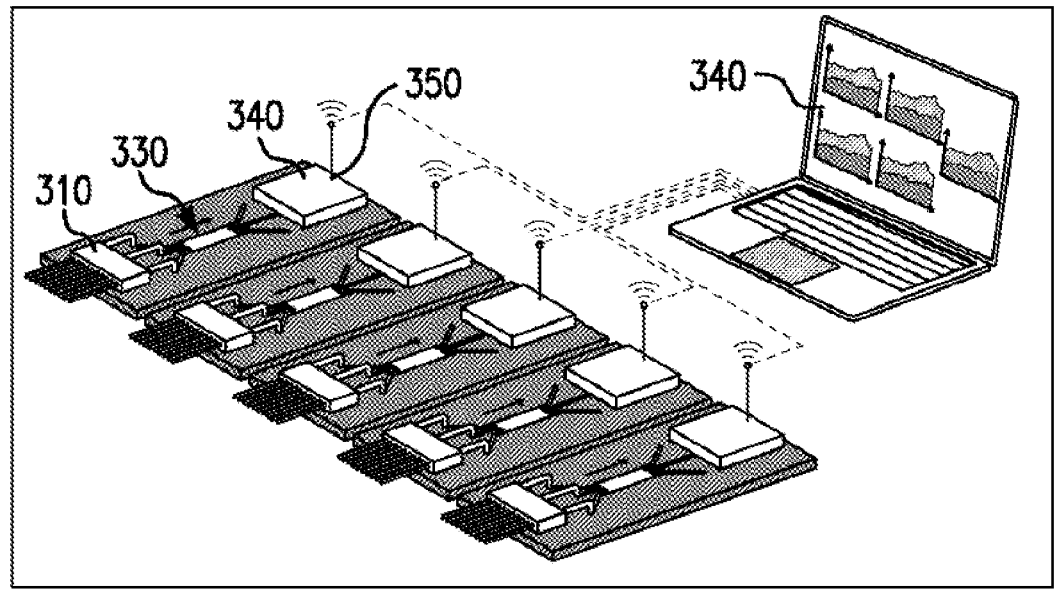
FIG. 7A is a schematic illustration of the augmentation of discrete microphysiological devices with on-chip fluidic synthesizers and FIG. 7B is a schematic illustration of discrete microphysiological devices with on-chip fluidic synthesizers integrated into a single monolithic microphysiological platform.
Figure 7B:
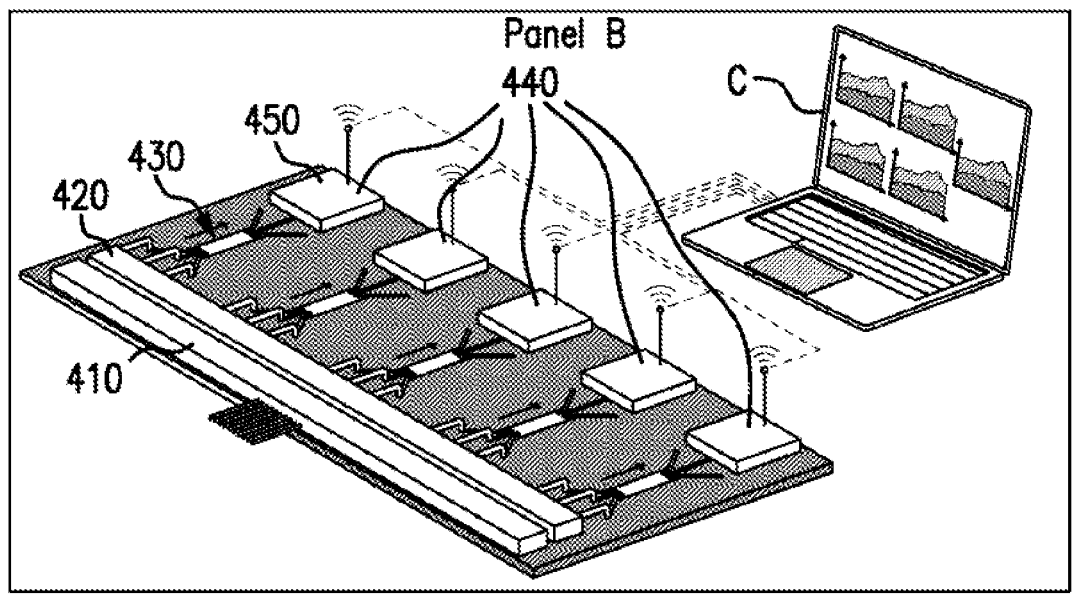

As shown schematically in FIGS. 1 and 2A-2B, in some embodiments, one or more sensor data transmitters 150 can be associated with one or more of the biosensors 140, to enable a measured datum or data from biosensor 140 to be transmitted to a device external to microphysiological platform 100, such as data receiver 181 that is part of a control system 170. This is also illustrated schematically in FIGS. 7A and 7B. FIG. 7A illustrates an exemplary diagram of the augmentation of discrete microphysiological devices 330, each integrated with an on-chip fluidic synthesizer 310. The microphysiological devices 330 further include chemical sensors or biosensors 340 located downstream of the microphysiological device 330. Digitally transduced data from one or a plurality of the sensors can be transmitted by sensor data transmitter 350 to an electronic device, such as computer C for continuous, automatic monitoring, and data processing. FIG. 7B shows an exemplary diagram of the integration of multiple discrete microphysiological devices 430 into a single monolithic microphysiological platform 400, in which the fluid output from a single fluidic synthesizer 410 can be addressed to one or a plurality of selected individual microphysiological devices 430 using a fluid addressing system 420. Downstream of the individual microphysiological devices 430 lie biosensors 440, which can allow transduction of the fluid's partial or whole chemical composition and subsequent transmission of said compositional measurement or measurements by sensor data transmitters 450 to an electronic device such as computer C for data monitoring, data processing, or data monitoring and processing.

Returning to FIGS. 1 and 2A-2B, in some embodiments, a biosensor 140 with a sensor data transmitter 150 can characterize the concentrations of a mixture of fluid constituents at certain given positions and transmit this information electronically to a fluidic synthesizer, such as fluidic synthesizer 110, at a different position. This different position can refer to a different position in the same microphysiological platform 100, to another microphysiological platform 100 engaged with the same control system, or to another microphysiological platform or other device altogether. Then, the fluidic synthesizer can dynamically resynthesize this same fluid mixture and outflow it. Since the connection can be electronic, the link between the sensor and the fluidic synthesizer can span just several millimeters on the same physical device (e.g., on the same microphysiological platform 100), or the link can span two or more of the disclosed microphysiological platforms located across the world from one another. This enables functionality described in more detail below.

The microphysiological platform 100 described above provides the capability for the fluidic synthesizer 110 to create a first fluid mixture to be delivered by fluid addressing system 120 to a first microphysiological device 130. Then, the fluidic synthesizer 110 can create a second fluid mixture that can subsequently be delivered by fluid addressing system 120 to a second microphysiological device 130. By this operation, microphysiological platform 100 can sequentially deliver at least one unique fluid mixtures to at least one microphysiological device 130 integrated into the microphysiological platform 100. In some embodiments, this operation can be cycled autonomously (e.g. wider the control of a main controller of control system) to create an automated microphysiological platform 100. In some embodiments, fluidic synthesizer 110 can produce multiple fluid mixtures sequentially, and fluid addressing system 120 can route the mixtures to the designated microphysiological devices 130. In some embodiments, each microphysiological device 130 can have its own fluidic synthesizer delivering a unique fluidic mixture. Alternatively, multiple fluidic synthesizers 110 incorporated into microphysiological platform 100 can operate simultaneously at multiple positions.

In some embodiments, microphysiological platform 100 can perform diagnostic procedures to attempt to detect a component failure, an impending component failure, or a component anomaly. Such diagnostic procedures can be performed at various time points. For example, a diagnostic procedure can be performed preemptively prior to the start of an experiment, at one or a plurality of discrete intervals during the course of an experiment, continuously during the course of an experiment, at the conclusion of an experiment, or a combination thereof. In some embodiments, such diagnostic procedures can include the characterization of fluids through components (e.g. microphysiological devices 130) in the microphysiological platform 100, the actuation of valves or flow controls in the microphysiological platform 100, the measurement of one or a plurality of sensor readings, the measurement of fluid flow rates, the measurement of electrical properties, automated or semi-automated optical inspection, or combinations thereof. In some embodiments, microphysiological platform 100 can passively monitor heuristics, performance measurements, performance metrics, or a combination thereof against expected or nominal values to monitor itself for component failures or component anomalies without actively performing diagnostic procedures.

Figure 8A:
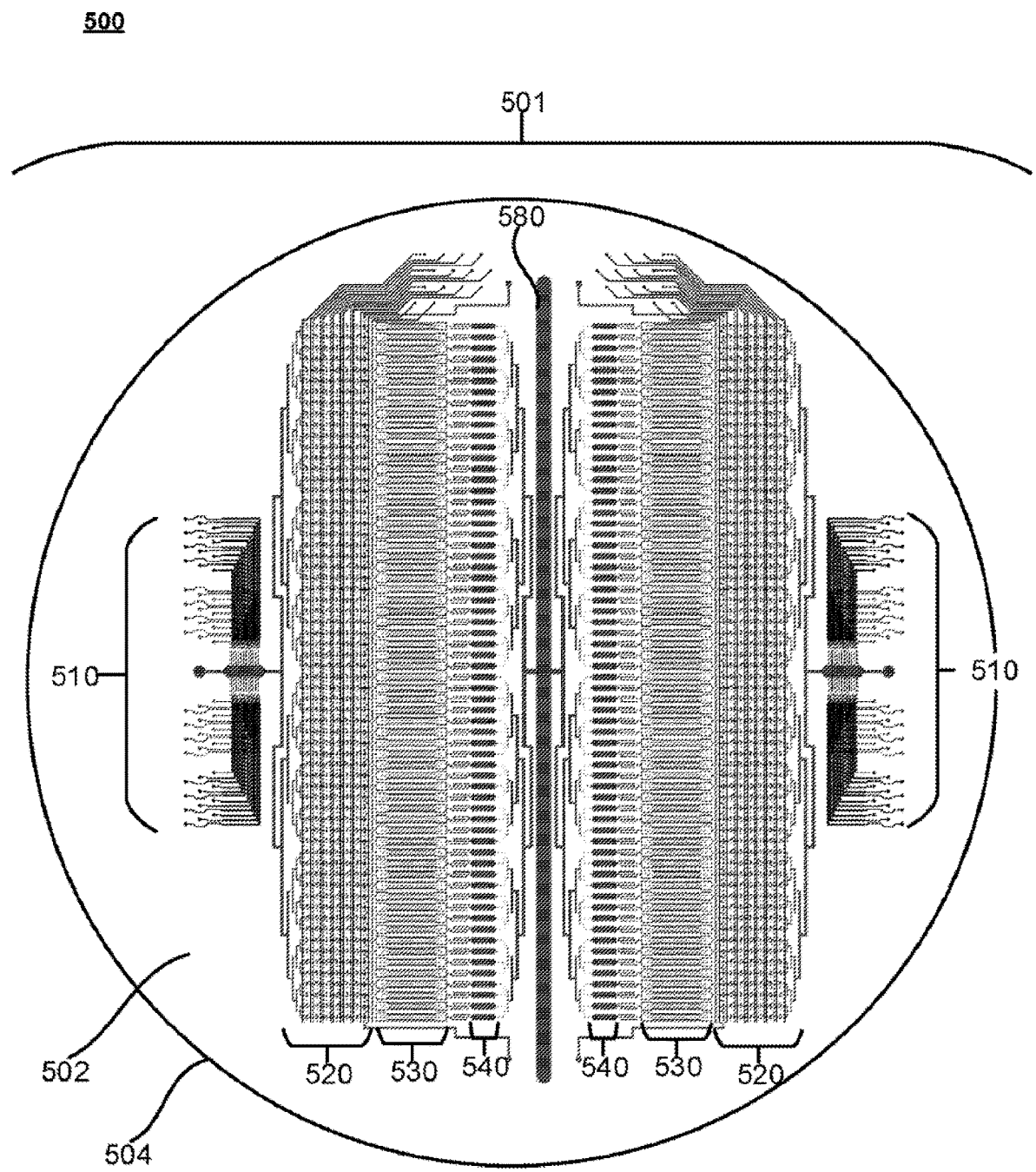
FIG. 8A shows an illustration of a microphysiological platform that integrates numerous individual microphysiological devices with associated sensors in a single multilayer microfluidic device, according to an embodiment.

One exemplary implementation of microphysiological platform 100 is shown in FIGS. 8A to 8D. FIG. 8A shows a plan view of a microphysiological platform 500. As shown in FIG. 8A, microphysiological platform 500 is implemented on a flat, circular substrate 501 with a peripheral edge 504. As shown in FIG. 8A, in this exemplary embodiment, the components of microphysiological platform 500 have a tiled or mirrored layout (which can be analogous to certain tiled instruction-executing cores of a multi-core microprocessor). That is, each half of microphysiological platform includes a fluidic synthesizer 510, a fluid addressing system 520, an array of microphysiological devices 530, and an array of biosensors 540. The two halves of the microphysiological platform share a common effluent channel 580.

Figure 8B:
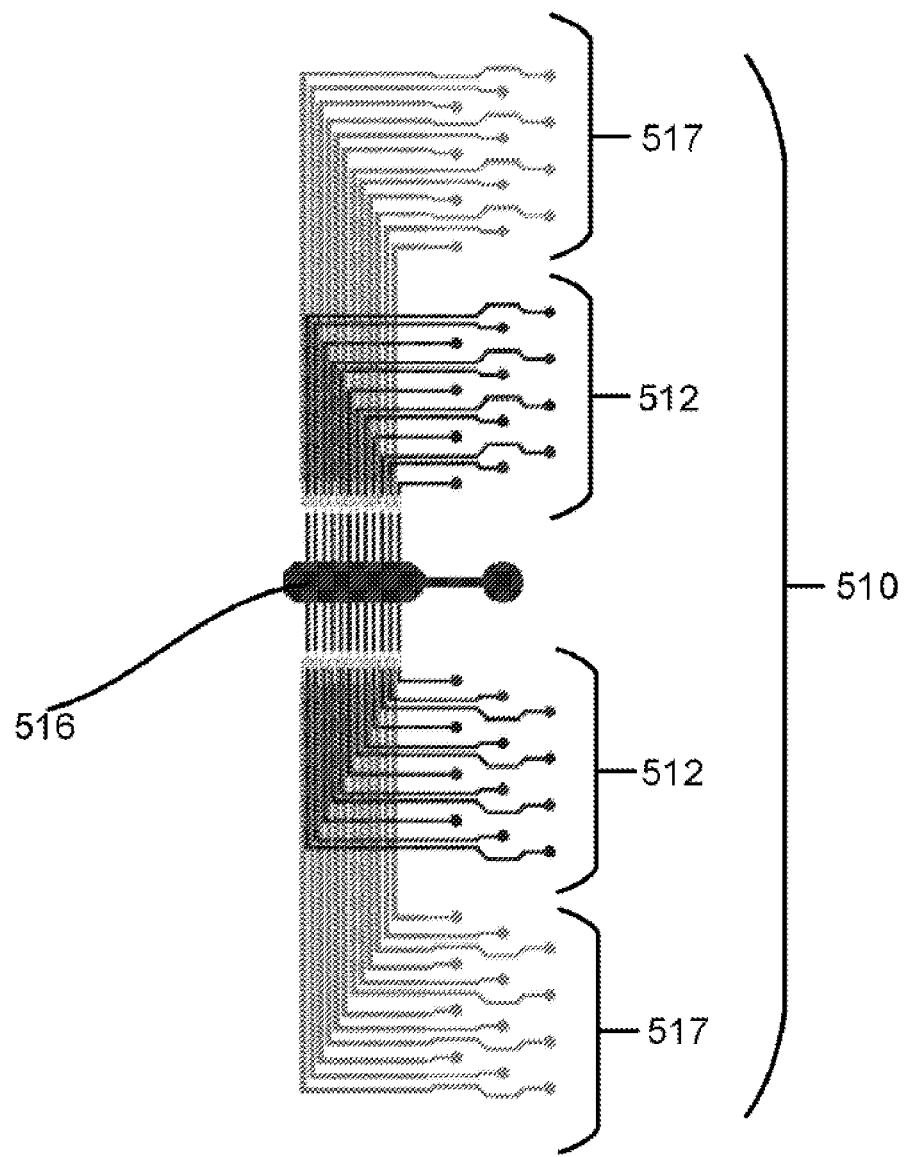
FIGS. 8B, 8C, and 8D show portions of the microphysiological platform.
Figure 8C:
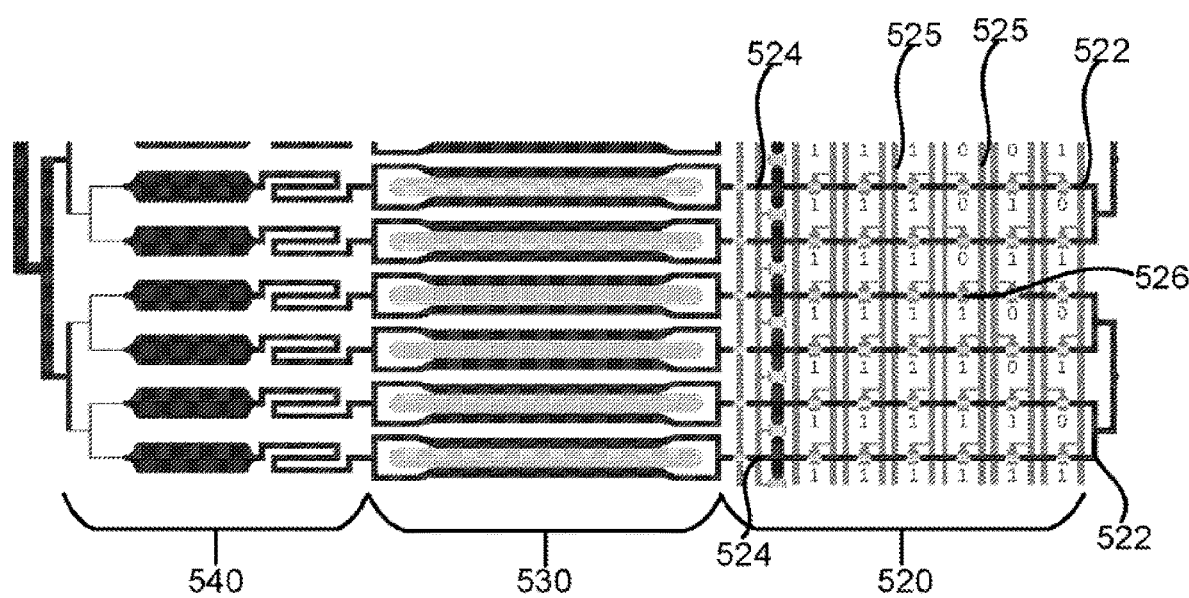

In this embodiment, each microphysiological device 530 is paired in a one-to-one relationship with a dedicated biosensor 540 (similar to the embodiment shown in FIGS. 6A to 6D). Each array of microphysiological devices 530 includes 64 devices, and correspondingly each array of biosensors 540 includes 64 biosensors. FIG. 8B shows a close-up view of the fluidic synthesizer 510. As shown, the fluidic synthesizer 510 includes fluid inlet ports 512, valve control ports 517, and mixing chamber 516. As shown, there is a 1:1 relationship between the fluid inlet ports 512 and the number of fluidic lines that go into the mixing chamber 516. FIG. 8C shows a close-up view of portions of the fluid addressing system 520, as well as portions of the array of microphysiological devices 530 and portions of the array of biosensors 540. As shown, the fluid addressing system 520 includes fluid inputs 522, fluid outputs 524, control lines 525, and valves 526. The fluid inlet ports 512 feed to the fluid inputs 522, while the valve control ports 517 and the control lines 525 control the valves. In some embodiments, the microphysiological devices 530 and the biosensors 540 can be the same or substantially similar to the microphysiological device 230 and the biosensors 240, as described above with reference to FIGS. 6A-6D. As shown, the biosensors 540 can be connected to the microphysiological devices 530 via a serpentine flow path.

Figure 8D:
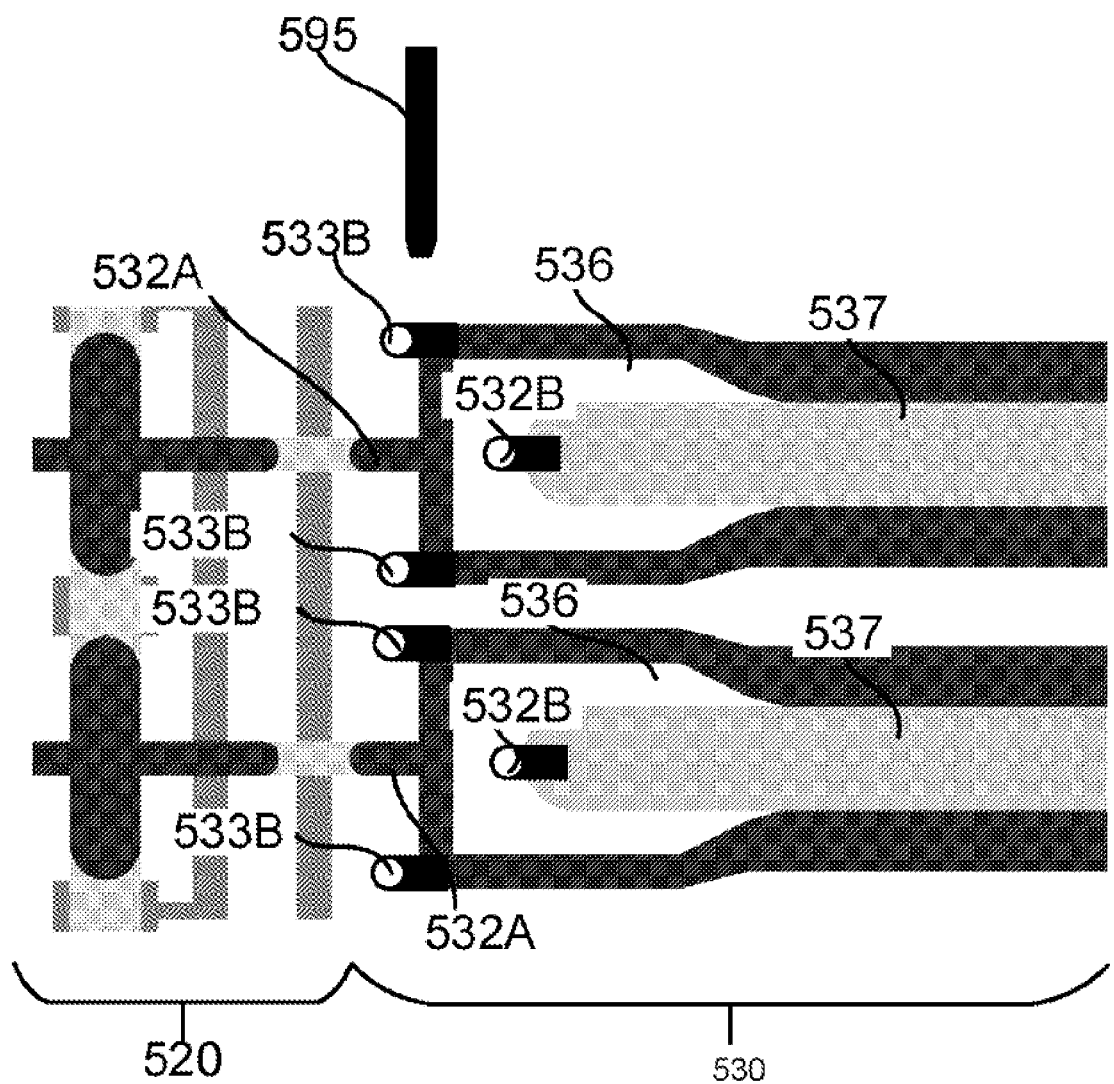

FIG. 8D shows a close-up view of an interface between the fluid addressing system 520 and the array of microphysiological devices 530. As shown, the microphysiological devices 530 include tissue chambers or tissues 537, channels 536, tissue input 532A, tissue input 532B, and channel input 533B. A fluid handler 595 is also shown. In some embodiments, the tissue input 532A can be the same or substantially similar to inputs 132-1A or 132-NA, as described above with reference to FIG. 5A. In other words, fluids can pass between the fluid addressing system 520 and the tissue chamber or tissue 537 via the tissue input 532A. In some embodiments, the tissue input 532B can be the same or substantially similar to inputs 132-1B or 132-NB, as described above with reference to FIG. 5A. In other words, fluids can pass between the fluid handler 595 and the tissue 537 via the tissue input 532B. In some embodiments, the channel input 533B can be the same or substantially similar to inputs 133-1B or inputs 133-NB, as described above with reference to FIG. 5A. In other words, fluids can pass between the fluid handler 595 and the channels 536 via the channel input 533B. In some embodiments, the microphysiological devices 530 can include inlets that create fluidic paths between the fluid addressing system 520 and the channels 536 (e.g., the same or substantially similar to the inputs 133-1A and 133-NA, as described above with reference to FIG. 5A). Any combination of the aforementioned fluidic couplings can be included in the microphysiological platform 500.

In some embodiments, such as that shown in FIGS. 8A to 8D, the two instances of the components (e.g., microphysiological devices 530 and/or sensors 540 associated with microphysiological devices 530) can be identical. This layout can allow one instance to function independently of one or a plurality of other instances for increasing operational throughput or operating in an identical-copy configuration for redundancy. For example, while biological replicates can be added to microphysiological devices 530 to improve statistical rigor or to increase reproducibility, mirroring several components of the entire system across both sides to create two instances of "cores" can permit fault tolerance for operational anomalies (e.g., inlet clogging, fluid leakage, valve puncture, component failure, or combinations thereof). In some embodiments, the mirrored or tiled components can be disabled without affecting other patterned instances. This redundancy can allow devices with manufacturing defects to be "binned" or operationally restricted to a lower capability or feature set. Such binned or restricted microphysiological platforms can be used for various purposes. For example, the binned or restricted microphysiological platforms can be sold or marketed at different tiers of technological capability. Such binned or restricted microphysiological platforms can operate or complete portions of an ongoing experiment following the partial failure of one or a plurality of components. Such binned or restricted microphysiological platforms can also serve as a substrate for a test, calibration, demonstration, or sampling procedures.

Although the microphysiological platform 500 shown in FIGS. 8A to 8D includes two instances of identical sets of components, in other embodiments more than two instances of components can be included, e.g. three, four, or more.

Fluid "Teleportation"

As noted above, the microphysiological platform architecture described herein provides for powerful capabilities. One important capability is "fluidic teleportation." "digital teleportation," or virtual fluidic coupling between components that are on the same microphysiological platform or distributed across multiple platforms that are physically/geographically separated (e.g. multiple microphysiological platforms engaged with the same control system, engaged with different control systems in the same room, facility, etc., or engaged with control systems spaced across the world). The fluidic teleportation can also provide virtual replicated or multiple fluidic coupling, e.g. a single device can be virtually fluidically connected to many "downstream" devices. Fluidic teleportation can also provide for temporally distributed virtual fluidic coupling (e.g. the time lapse between the detection of the composition of a fluid exiting a first device and the synthesis of a fluid with the same composition for delivery to a second device (or many second devices) that is not fluidically coupled to the first device, can be very short, or very long). More details, and exemplary implementations, of fluid teleportation are described below.

As noted above, fluidic teleportation can enable creation of a fluidic interconnection between at least two locations within a fluidic or microfluidic network without modifying the existing topology or arrangement of the network (e.g., without physically bridging or connecting said locations by physical means). For example, the fluidic interconnection can be established without connecting physical tubing or creating a physical interconnection between the locations that allow direct fluid flow. The interconnection can be established between at least two discrete, separate, or disconnected fluidic networks (e.g., chambers or components). The interconnection can be established between at least two sequential locations positioned opposite to the direction of a unidirectional fluid flow (e.g., the interconnection of a first location to a second location that is upstream of the first location). The interconnection can be established between at least two locations separated by a flow restrictor, one-way valve, a filter, a component that selectively disallows the physical passage of chemical constituents of the fluid, or combinations thereof.

Figure 9:
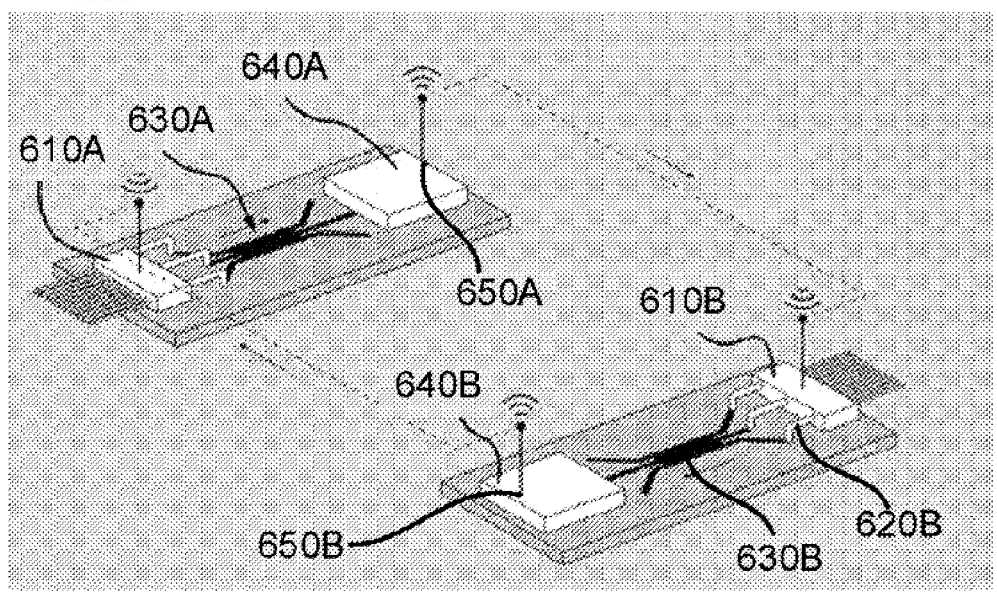
FIG. 9 is a schematic illustration of a fluidic teleportation system, according to an embodiment.

A simple implementation of a fluidic teleportation system 600 is illustrated schematically in FIG. 9. As shown, the fluidic teleportation system 600 includes a first fluidic synthesizer 610A, a first microphysiological device 630A, a first multi-analyte fluidic transducer/biosensor 640A, and a first sensor transmitter 650A integrated into a first device. As shown, the fluidic teleportation system 600 further includes a second fluidic synthesizer 610B, a second microphysiological device 630B, a second multi-analyte fluidic transducer/biosensor 640B, and a second sensor transmitter 650B integrated into a second device. As shown in FIG. 9, the outflow of the first microphysiological device 630A can be coupled to the inlet of the second microphysiological device 630B without a direct fluidic connection, by using a fluidic-to-digital signal transduction, a digital signal transmission, and then a digital-to-fluidic transduction, thus creating a virtual fluidic connection. As shown in FIG. 9, multi-analyte fluidic transducers/biosensors 640A located downstream of the microphysiological devices 630A can transduce the fluidic composition of the effluent of microphysiological device 630A into a digital signal that can be wirelessly transmitted by sensor transmitter 650A to the second fluidic synthesizer 610B located upstream of the coupled second microphysiological device 630B for reconstitution and subsequent perfusion.

Figure 10:
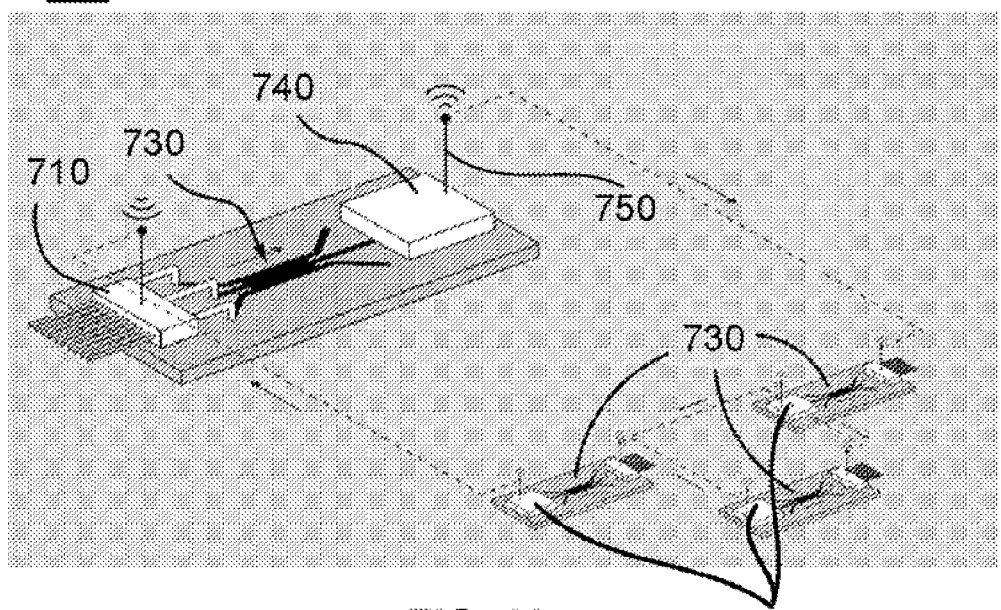
FIG. 10 is a schematic illustration of a fluidic teleportation system, according to an embodiment.

Another implementation of a fluidic teleportation system 700 is illustrated schematically in FIG. 10. In the implementation, multiple microphysiological devices 730 are dynamically coupled b connections between the devices' respective multi-analyte transducers/biosensors 740 and the sensor transmitters 750. Each of the microphysiological devices 730 is fed via a fluid synthesizer 710. Since the system can be connected through a fluidic-to-digital and subsequent digital-to-fluidic transduction, the devices can be arbitrarily distant from each other as long as digital communication is possible.

Figure 11A:
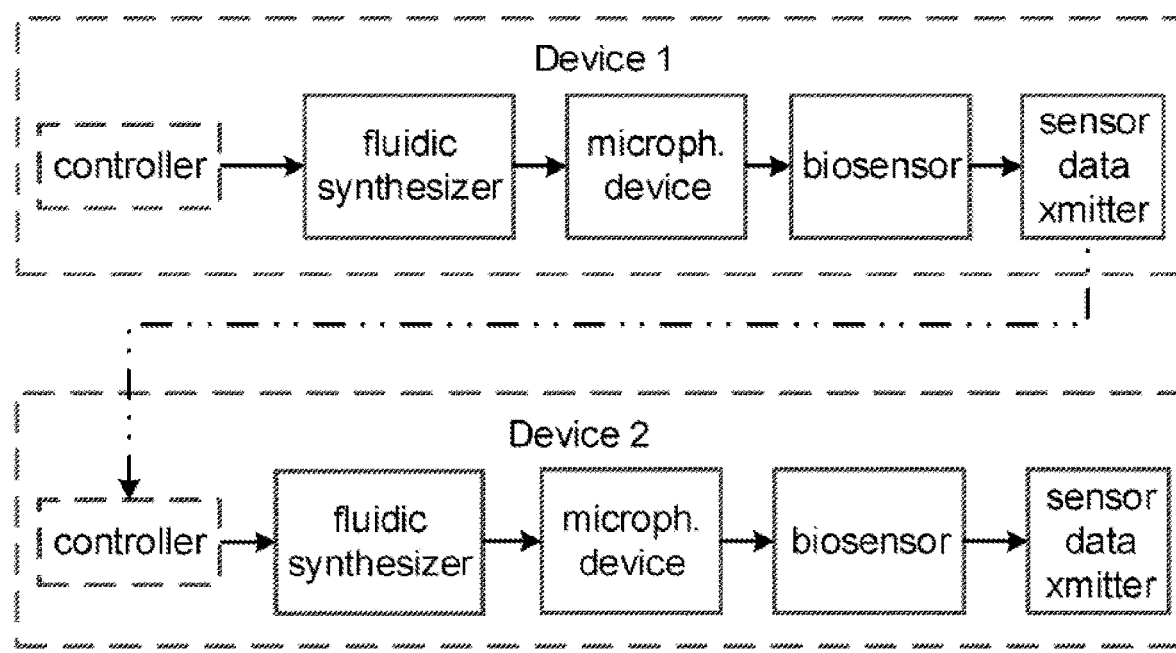
FIGS. 11A to 11D are schematic illustrations of different topologies of fluidic teleportation systems, according to various embodiments.
Figure 11B:
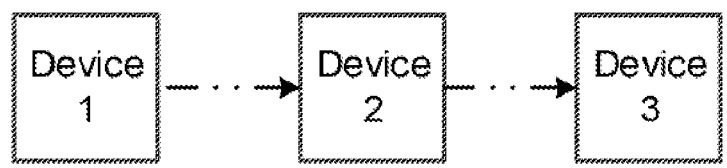
Figure 11C:
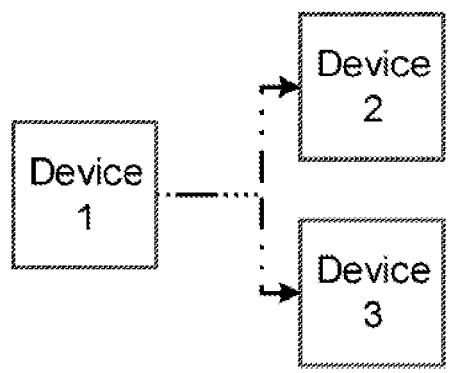
Figure 11D:
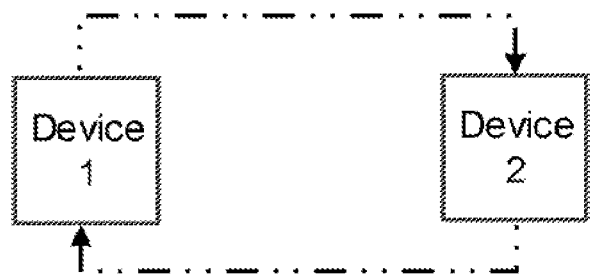
Figure 12:
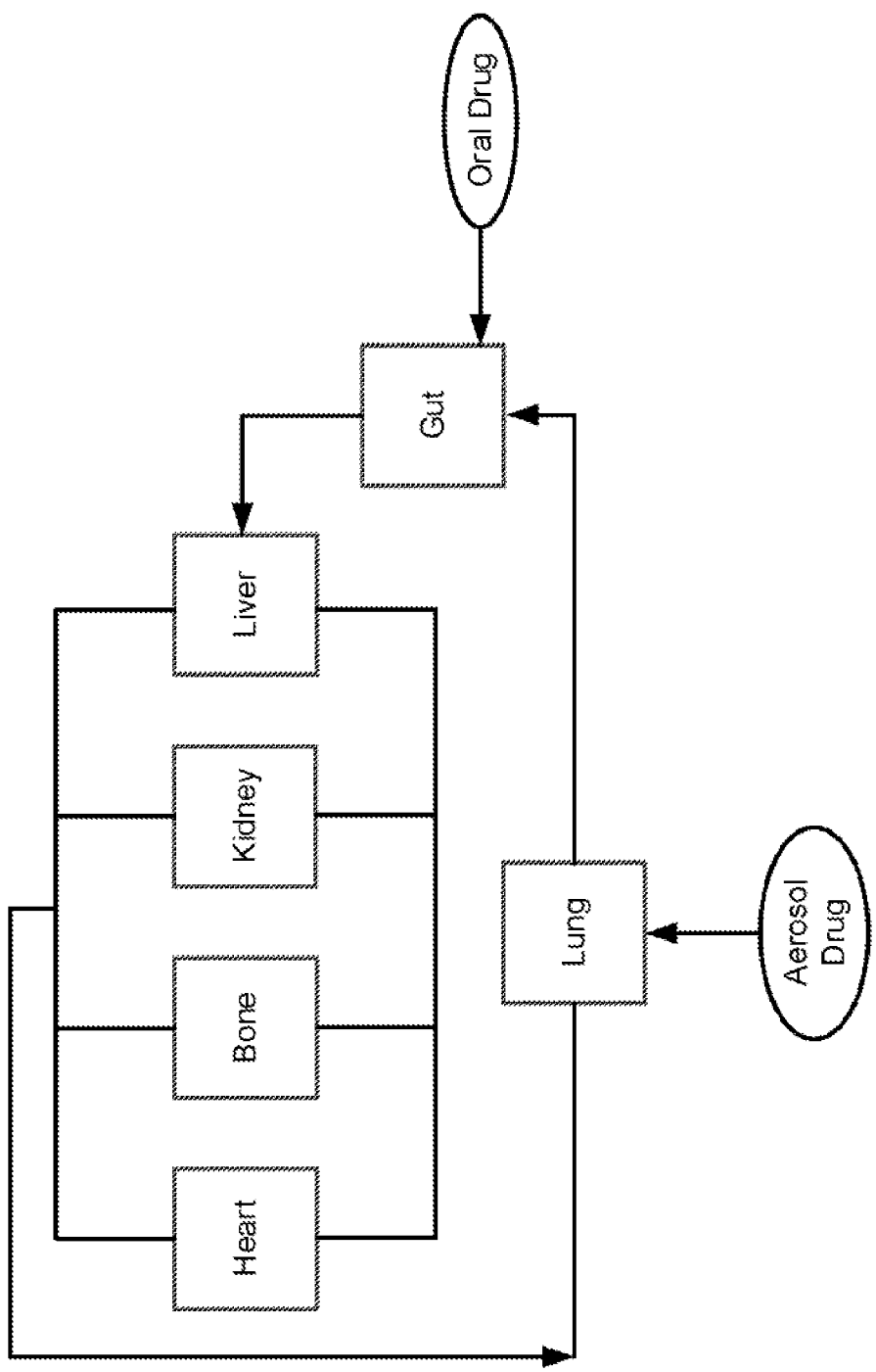
FIG. 12 is a schematic illustration of a human-body-on-a-chip model including multiple microphysiological devices that each recapitulate the physiology or function of a particular human tissue, organ, or system, each connected to one or more other devices by digital fluidic teleportation.

FIG. 11A to are schematic illustrations of different topologies of fluidic teleportation systems, according to various embodiments. As shown in FIG. 11A, movement of a signal can be from a first device to a second device. More specifically, the controller of Device 1 can control the fluidic synthesizer, the microphysiological device, and/or the biosensor and data from Device 1 can be transmitted from the sensor data transmitter of Device 1 to the controller of Device 2. Based on the data transmitted from to the controller of Device 2 from the sensor data transmitter of Device 1, the controller of Device 2 can modify its control of the fluidic synthesizer, the microphysiological device, and/or the biosensor of Device 2. As shown in FIG. 11B, devices can be arranged in a serial virtual connection. In other words, data from Device 1 can be applied to the controller of Device 2 to control the operation of Device 2 and data from Device 2 can be applied to the controller of Device 3 to control the operation of Device 3. As shown in FIG. 11C, data from a first device can be applied in controlling the operation of multiple additional devices in a multiplexed 1:2 (or 1:N) virtual connection. As shown in FIG. 11C, data from Device 1 is used in controlling the operation of Device 2 and Device 3. As shown in FIG. 11D, devices can be arranged in a feedback loop. In other words, output from a downstream device (e.g., Device 2) can be communicated to an input of an upstream device (e.g., Device 1). In some embodiments, any of the aforementioned topologies can be combined to create any desired teleportation device. An example of a complex arrangement of teleportation devices is shown in FIG. 12.

The dynamic coupling between multiple microphysiological devices can be used, for example, for the assembly of a human-body-on-a-chip model having a multitude of microphysiological devices that each recapitulate the physiology or function of a particular human tissue, organ, or system, each connected to one or more other devices by digital fluid teleportation. This is illustrated schematically in an example embodiment in FIG. 12. As shown in FIG. 12, a system of organ-on-a-chip microphysiological devices can include a gut device, a liver device, a kidney device, a bone device, a heart device, and a lung device. An oral drug can be administered (e.g. through a fluidic synthesizer and fluid addressing system, and/or directly to the device, e.g. by a fluid handler, as described above, to the gut device and an aerosol drug can similarly be administered to the lung device. As shown in FIG. 12, an oral drug can be simulated in an inlet to a gut device, and the gut device can communicate with a liver device, a kidney device, a bone device, and a heart device. Based on the data output from the gut device, the inputs to the liver device, the kidney device, the bone device, and the heart device can be controlled or manipulated. Based in data output from the liver device, the kidney device, the bone device, and the heart device, the controller of the lung device can manipulate the controller of the gut device. The operation and data derived form the lung device can also be affected by the aerosol drug administered to the lung device. In some embodiments, connections between the different organ devices can be virtual and/or physical. In some embodiments, the different organ-on-a-chip devices can be contained on a single microphysiological platform, or distributed across two or more microphysiological platforms. In some embodiments, a central control system can control each of the organ devices. In some embodiments, the central control system can be integrated into a single apparatus that includes each of the organ devices, on a single microphysiological platform or multiple microphysiological platforms. In some embodiments, one or more of the organ platforms can be implemented on removable disks.

In some embodiments, digital fluid teleportation implementations (e.g., from one organ platform to another organ platform) can include measuring the concentration or presence of at least one target analyte in a first fluid at a first location and synthesizing a second fluidic solution using a fluidic synthesizer. The second fluidic solution can include at least one target analyte at the measured concentration or at a concentration derived from mathematical adjustment or transformation of the measured concentration. The second fluid can be an identical, a partial, or a derivative mixture of the first fluid. In certain embodiments, the method can further include flowing the second fluidic solution from the fluidic synthesizer to a second location without transporting the first fluidic solution from the first location to the second location through a continuous fluid flow. For example, a whole or partial fluid composition characterized by at least one sensor at a first location can be "digitally teleported" to a second location by wholly or partially reconstituting the first fluid at the second location. These methods can be performed without requiring physically connecting the first fluid at the first location to the second location. In certain embodiments, this method of digital fluid teleportation can allow an identical, partial, or derivative mixture of the first fluid at the first location to be copied (by "digital fluid teleportation") across any distance to one or a plurality of additional locations, so long as a means of data communication or data transport exists between those at least two locations.

The method can include creating a first fluid mixture using a first fluidic synthesizer, incubating a first microphysiological device with the first fluid mixture to generate a second fluid mixture, incubating the first fluidic solution with a first microphysiological device at the first location to generate the second fluidic solution, measuring a concentration of one or a plurality of target analytes in the second fluid mixture using chemical sensors, and synthesizing a third fluid mixture by using the first fluidic synthesizer to reconstituting an identical, partial, or derivative mixture of the second fluid mixture. In non-limiting embodiments, the method can further include incubating with the third fluid mixture with the first microphysiological device, the second microphysiological device, at least two additional microphysiological devices, or combinations thereof to generate a fourth fluidic solution. In non-limiting embodiments, the method can further include measuring a concentration of the at least one target analyte in the fourth fluidic solution for subsequent perfusion.

In certain embodiments, the method for digital fluid teleportation can further include transmitting a measured concentration to at least one external receiver. The external receiver can include at least one of a computer, an electronic controller, an electronic control system, a network address, a network monitor, the first fluidic synthesizer, one or a plurality of fluidic synthesizers, and a control server. In non-limiting embodiments, the method for digital fluid teleportation can further include incubating a second tissue with the third fluidic mixture to generate a fourth fluidic mixture. In some embodiments, the method can further include measuring a concentration of the target analyte in the fourth fluidic mixture for subsequent perfusion. In certain embodiments, digital fluid teleportation can enable the fluidic interconnection of at least two microphysiological devices without requiring the preemptive placement of said devices in a physically connected manner or along a sequential fluid pathway. In certain embodiments, interconnections created by digital fluid teleportation can be dynamically or discretely enabled, disabled, rerouted, or a combination thereof, continuously or at one or a plurality of intervals.

In certain embodiments, the disclosed subject matter provides methods for digital fluid teleportation between at least two organ-on-a-chip devices. In certain embodiments, a fluidic chemical sensor or biosensor can perform a real-time acquisition and readout of the composition of a first fluid or fluid mixture at its location at a first organ-on-a-chip device. This readout can be transmitted digitally to be dynamically resynthesized and outflowed from a second location by a fluidic synthesizer. The outflowing resynthesized fluid can be directed to the second organ-on-a-chip device including a fluid addressing system. In certain embodiments, an identical, a partial, or a derivative constituent mixture of the first fluid can be delivered to the second organ-on-a-chip without the requirement that the first organ-on-a-chip be connected to the second organ-on-a-chip. In such a manner, by coupling one or more integrated fluidic biosensors with one or more fluidic synthesizers capable of recreating the identical, partial, or derivative constituent mixture of the first sensor-characterized fluid mixture at a second, different position on the chip, the first fluid can be "copied" from one position and "pasted" elsewhere on the same platform, or onto another platform which possesses a fluidic synthesizer with the appropriate inlet compounds.

In certain embodiments, the sensor signal used for digital fluid teleportation can be digitally transmitted wirelessly or through any transmission network or protocol capable of transferring digital data. In certain embodiments, a digital signal can be transmitted back to a fluidic synthesizer of the same organ-on-chip for modeling of feedback loops.

In certain embodiments, digital fluid teleportation allows a fluid composition to be digitally transported in a manner, or to a location or locations, that is incompatible with the limitations of physical fluid flow. For the purpose of illustration and not limitation, the transportation can include transport across an air gap or other obstacle blocking fluid flow (e.g., a flow restriction or one-way valve), transport across a distance at a rate faster than can be achieved through certain physical fluid conduit (because a sensor signal can be transmitted at the speed of light), transport that is routed between destinations at a rate that exceeds the capacity of physical multi-way valving, or combinations thereof.

In certain embodiments, two physically discrete organ models can be connected by the disclosed digital fluid teleportation method. As a non-limiting example, models of multi-organ systems can be formed between at least two microphysiological devices within the microphysiological platforms that are integrated without physical fluidic connections that link the microphysiological devices or organ models directly. In certain embodiments, the disclosed system can be operated without the unintended leakage of a fluidic biochemical microenvironment between said microphysiological devices or fluidic dilution of constituents between the said organ models or microphysiological devices.

In certain embodiments, to connect a first microphysiological device to a second microphysiological device, the disclosed system can read the fluid composition with a biosensor for at least one fluidic analyte or constituents at the outlet of the first microphysiological device, transmit the readouts to a fluidic synthesizer upstream of the second microphysiological device to synthesize a second fluid mixture with an identical, a partial, or a derivative constituent mixture of the first fluid, and then flow this composition onwards to the second microphysiological device. In non-limiting embodiments, a digital fluid teleportation method can be applied to transport one or a plurality of fluids between any one or a combination of microphysiological devices integrated into the microphysiological platform shown in FIGS. 1 and 2. The fluidic outflow of any microphysiological device can be sampled, reconstructed in the fluidic synthesizer, and addressed to any other microphysiological device by the fluid addressing system. This process can be performed sequentially to link multiple microphysiological devices. For example, a first microphysiological device's output can be reconstituted and be delivered to a second microphysiological device. The fluid outflow of the second microphysiological device can be reconstituted and delivered to a third microphysiological device, and so forth.

In certain embodiments, the connections established by digital fluid teleportation between two or more locations in the platform (e.g., between microphysiological devices) can be newly established, modified, or closed in real-time, or in an otherwise dynamic manner. Unlike an inflexible system formed solely from physical fluid conduits, the disclosed subject matter can allow coupling between microphysiological systems after a stable state, a target state, or a desired operational duration has been established. In non-limiting embodiments, the coupling can be disabled at predetermined time points. For example, the behavior of one microphysiological device can be evaluated in the temporary absence of the other. In certain embodiments, this dynamic establishment of fluid connections by digital fluid teleportation can allow organ-on-a-chip models to be cultured in isolation for some target duration (e.g., one day, or one week, or one month), after which they can be fluidically coupled to model organ-to-organ or tissue-to-tissue interactions. In certain embodiments, this dynamic establishment of fluid connections by digital fluid teleportation can allow two distinct microphysiological devices to be cultured in isolation for some target duration (e.g., one day, or one week, or one month). After the connection, microphysiological devices can be fluidically coupled to model dynamics (e.g., the exposure of a first biological entity to secretions or chemical compounds produced by a second biological entity, the biological feedback phenomena produced from such a unidirectional or bidirectional coupling, or the biological reactions of a chain reaction between more than two biological entities).

In certain embodiments, the fluid characterized by one biosensor can be fluidically resynthesized by digital fluid teleportation for transmission to multiple targets in order to produce dynamic fluidic duplications. For example, the fluid delivered to multiple microphysiological devices cultured as replicates (for purposes including, without limitation, statistical rigor or hypothesis testing) can be simultaneously coupled to the fluidic composition measured at the effluent of a single driving microphysiological device. The effluent can be characterized by a sensor placed at the outlet of said driving microphysiological device. Then, upon teleportation to a fluidic synthesizer, the fluidic synthesizer can reconstitute the mixture and flow an equal unit volume of the same mixture to each of the replicate microphysiological devices through a fluid addressing system. In certain embodiments, the replicates to which said fluid mixture is delivered can be biologically identical. In certain embodiments, the replicates to which said fluid mixture is delivered can be nominally biologically identical (e.g., they can be cultured with the same initial conditions for purposes of being identical replicates), for predetermined purposes (e.g., classification or quantification of their resultant variability). In certain embodiments, the intentional variability can include a source of tissues cultured in different microphysiological devices, a pathophysiological state of tissues cultured in said replicates, or the age of tissues cultured in said replicates. In certain embodiments, this technique can be used to analyze the different behaviors or responses exhibited by healthy versus diseased organ models in response to exposure to the same dynamic fluidic environment.

In certain embodiments, a fluid can be duplicated by digital fluid teleportation to two locations simultaneously, by the transmission of the sensor signal to two fluidic synthesizers. In certain embodiments, a fluid can be duplicated by digital fluid teleportation to two locations sequentially by teleportation to one fluid synthesizer whose output is addressed to a first location by a fluid addressing system. Then the fluid can be teleported to the same fluid synthesizer to address the same fluid mixture as an output to a second location by the said fluid addressing system. In certain embodiments, the desired fluid mixture can be duplicated to three or more locations.

In certain embodiments, digital fluid teleportation can transport greater or smaller volumes of a fluid composition to one or more secondary locations relative to the volume of said fluid that is sampled by a plurality of sensors at a first location. For purposes of illustration and not limitation, a sensor at a first location can sample a chamber containing 0.1 milliliters of fluid, and this measured fluid composition can be transported by digital fluid teleportation to a second location at which 1.0 ml of an identical fluid composition can be synthesized by a fluidic synthesizer.

In certain embodiments, a sampled fluidic composition can be transported by digital fluid teleportation not only spatially, but also through time, or temporally. In certain embodiments, temporal teleportation can be achieved by placing a delay between one or more sensors at a first location, and a fluidic synthesizer that recreates the mixture at a second location. For purposes of illustration and not limitation, this can be utilized to mimic natural phenomena. For example, the natural phenomena can include the transit time of a hormone or biological entity between tissues in the human body. When multiple microphysiological devices are interconnected by digital fluid teleportation, the sequential transport of a metabolite or biological entity between a plurality of tissues or organs in a timed sequence can be performed.

In certain embodiments, the one or more sensors can perform a discrete or continuous recording of a fluidic composition at a first location during a first time period. The sensors can also digitally store the sensor data that composes the recording. The recording can be reloaded to reproduce the recorded fluidic composition through a fluidic synthesizer. In certain embodiments, this method of loading a saved recording of a fluid composition can be used to recreate the fluid composition from said recording at a later date. In certain embodiments, this method of saving and then later loading a recording of a fluid composition can be used to archive particular behaviors or dynamics that are observed in an experiment in a microphysiological platform. The behaviors or dynamics can be recreated at a later date on a different microphysiological system. In certain embodiments, the sensor readings from the duration of an entire experiment can be saved, such that they can be accessed later for various purposes. The purpose can be a playback of said recording in whole or in part through the real-time re-synthesis of said recorded fluid compositions at a fluidic synthesizer. In certain embodiments, the technique of saving sensor data that characterizes a discrete or continuous fluid composition can increase the experimental reproducibility of multi-organ coupled systems for investigating rare phenomena.

Figure 13:
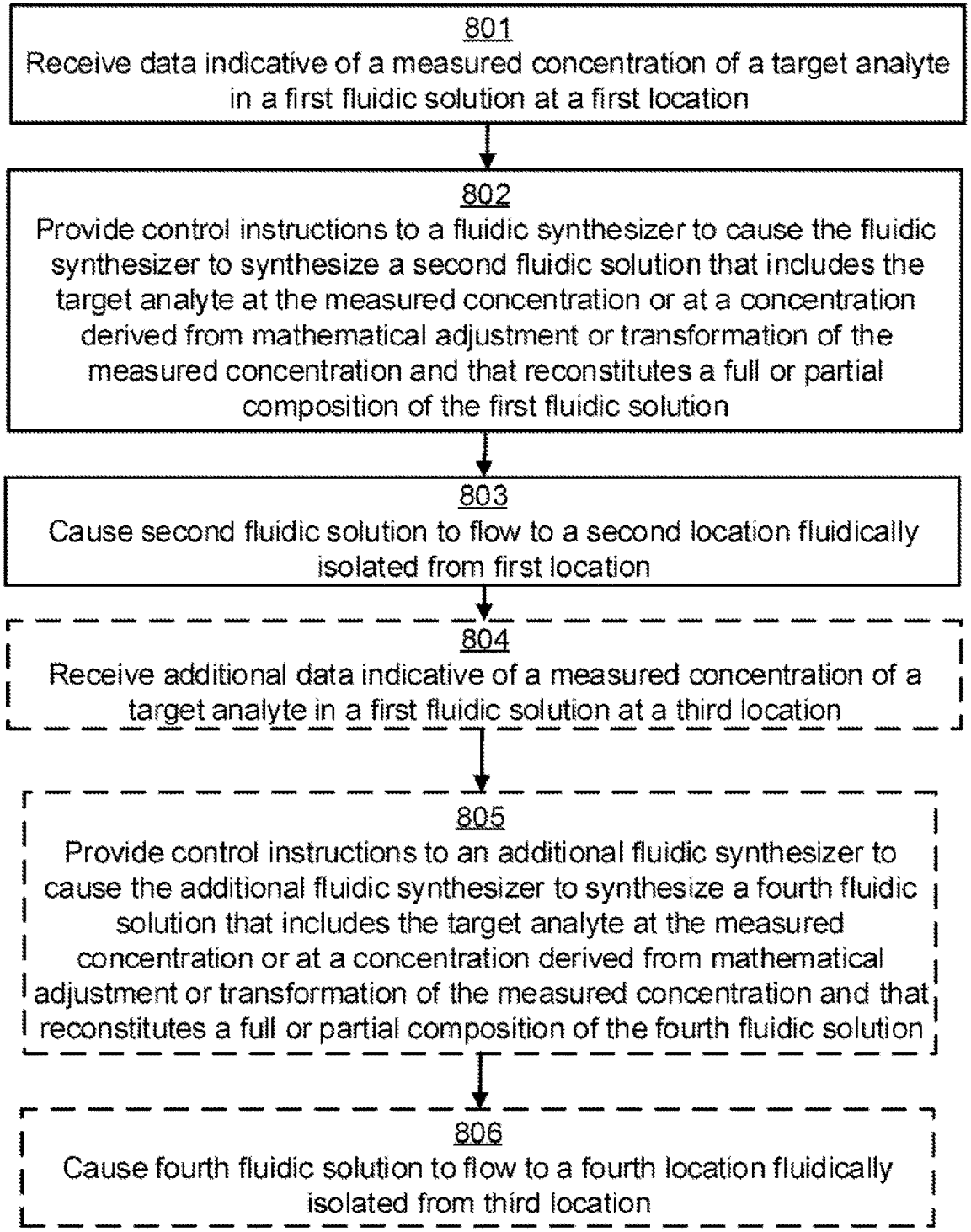
FIG. 13 is a flow diagram illustrating a method of fluidic teleportation, according to an embodiment.

FIG. 13 shows a flow chart of a nonlimiting example of a method 800 of digital fluid teleportation. The method 800 includes receiving data indicative of a measured concentration of a target analyte in a first fluidic solution at a first location as shown in 801. In some embodiments, the first location can be an organ-on-a-chip model. The method 800 further includes providing control instructions to a fluidic synthesizer to cause the fluidic synthesizer to synthesize a second fluidic solution that includes the target analyte at the measured concentration or at a concentration derived from mathematical adjustment or transformation of the measured concentration and that reconstitutes a full or partial composition of the first fluidic solution as shown in 802. In some embodiments, the second location can be on an organ-on-a-chip model. The method 800 further includes causing the second fluidic solution to flow to a second location that is fluidically isolated from the first location, shown in 803.

In some embodiments, the method 809) can include causing the second solution to flow to an additional location (i.e., different from the second location), the additional location fluidically isolated from the first location. In some embodiments, the first location and the second location can be on a single microphysiological platform. In some embodiments, the first location can be on a first microphysiological platform and the second location can be on a second microphysiological platform. In some embodiments, the first physiological platform and the second physiological platform can be engaged with a single control system. In some embodiments, the control system can receive the data, provide the control instructions, and cause the second fluidic solution to flow. In some embodiments, the first microphysiological platform can be engaged with a first control system and the second microphysiological platform can be engaged with a second control system. In some embodiments, the method 800 can further include receiving second data indicative of a measured concentration of the second target analyte in a third fluidic solution resulting from passage of the second fluidic solution through the second microphysiological device, shown in 804. In some embodiments, the method 800 can further include providing second control instructions to a second fluidic synthesizer to cause the second fluidic synthesizer to synthesize a fourth fluidic solution that includes the second target analyte at the measured concentration of the second target analyte or at a concentration derived from mathematical adjustment or transformation of the measured concentration of the second target analyte and that reconstitutes a full or partial composition of the third fluidic solution, shown in 805. In some embodiments, the method 800 can further include causing the fourth fluidic solution to flow to a third microphysiological device at a third location fluidically isolated from the first location and the second location, shown in 806.

In some embodiments, a method of fluid teleportation can include measuring the constituent concentrations of dissolved chemical elements and solutes in a fluid by utilizing a sensor specific to a first location. Optionally mathematical transformations can be applied to the measured concentrations. The mathematical transformations can include, for purposes of illustration and not limitation, doubling or halving the measured concentration of a solute during the production of a fluid at a fluid synthesizer, adding together two or more signals, constituent concentrations, or sets of constituents and their concentrations, adding one or more constant values to one or more constituent concentrations or signals, or combinations thereof. The concentration can be transmitted to a control system or a remote system. A fluid mixture with equivalent chemical or solute concentrations can be synthesized by mixing undiluted stock solutions together at a second location. In some embodiments, the mixture of the stock solutions can include an identical, a partial, or a derivative constituent mixture of the first fluid's measured concentration. The fluid mixture can be delivered to a third location. In some embodiments, the third location can be discrete or physically separated from the first location. In some embodiments, the third location can be discrete or physically separated from the second location. In some embodiments, teleporting the solution contents from the second location to the third location can be without a continuous fluidic connection between the second location and the third location.

In non-limiting embodiments, the microphysiological platform can record a rare stimulus in a microphysiological device through a plurality of sensor modalities or targets, record said stimulus, and replicate in real-time or at a later time on command. A plurality of such recordings can be replicated through multiple fluidic synthesizers, which can be located remotely from each other. In non-limiting embodiments, the sampled fluidic composition can be modified and teleported in real-time or at a later time to a fluidic synthesizer. For example, the concentrations of a plurality of constituent belonging to a measured fluid composition that is being transported by digital fluid teleportation can be modified from the concentration or concentrations measured in the fluidic recording. This technique can allow a characterized outflow of a dynamic environment at a first microphysiological device to be reconstituted at a second microphysiological device without requiring the physical presence of the first microphysiological device in proximity and in fluid communication with the second microphysiological device. In certain embodiments, the fluidic environment generated by a first microphysiological device can be resynthesized at a second microphysiological device at one or more later time points without requiring the first microphysiological device to be physically recreate said measured environment local to the first microphysiological device. Accordingly, this technique can decrease cost, material requirements, and processing time.

In certain embodiments, the transduced digital signal of a chemical or biosensor can be manipulated and adjusted before it is resynthesized as a part of digital fluid teleportation. In certain embodiments, a first fluid composition can be resynthesized as a second fluid by a fluidic synthesizer such that this second fluid is a partial or derivative mixture of the first fluid. In certain embodiments, the partial or derivative mixture of the first fluid can contain at least one constituent at concentrations measured in the first fluid. The partial or derivative mixture of the first fluid can be resynthesized in the second fluid at a different concentration from the measured concentration. The different concentrations can result from manipulation of the measured concentration by processes including algorithmic transformation, mathematical transformation, or transformation by signal processing techniques. For example, the disclosed techniques can allow characterizing a subset of constituents measured in the first fluid (e.g., determined by the stock solutions available to the fluidic synthesizer or by the linear combinations of stock solutions available to the fluidic synthesizer), a subset of constituents measured in the first fluid (e.g., determined by experimental requirements such as the incompatibility or toxicity of certain compounds at one location with the biological entities in the culture at a second location), a superset of constituents composed of a partial or whole mixture of the constituents in the first fluid mixture, additional constituents not present or not measured in the first fluid mixture, or combinations thereof.

In certain embodiments, digital fluid teleportation of a partial or derivative subset of a first sampled fluid at a first location to create a second fluid at a second location can prevent the bulk transport of certain undesired dissolved compounds in the first fluid by bulk fluid flow to the second location. In certain embodiments, such digital fluid teleportation of a partial or derivative subset of a first sampled fluid can prevent the bulk transport of certain undesired dissolved compounds without requiring a physical mechanism for selectively filtering said undesired compounds from the bulk fluid mixture.

In certain embodiments, the microphysiological platform including a plurality of individual microphysiological devices to culture organ-on-a-chip models can utilize digital fluid teleportation capability to selectively transport only a partial or derivative subset of the constituents in a first sampled fluid at a first organ-on-a-chip model to a second location corresponding to a second organ-on-a-chip model. In certain embodiments, the capability can be utilized to prevent the unintended transport of dissolved compounds (e.g., growth factors, biological secretions, drugs, or chemical compounds) from a first organ-on-a-chip to a second organ-on-a-chip model. In some embodiments, this allows multiple organ-on-a-chip models to be combined into a "human body on a chip" configuration that features multiple tissue types cultured in discrete organ-on-a-chip models (each housed in a microphysiological device, within a microphysiological platform) that are fluidically interconnected by digital fluid teleportation. In such embodiments for multi-organ or "human body on a chip" configurations, the capacity to selectively transport only a partial or derivative subset of the constituents in a sampled fluid can be utilized to transport only particular class chemical compounds (e.g., biologically secreted compounds, hormones, paracrine factors, endocrine factors, signaling molecules, or combinations thereof) without transporting undesired compounds (e.g., growth factors intended for the culture of only one tissue type, metabolic waste products, undesired signaling molecules, biological entities including viruses and bacteria, extracellular vesicles, or combinations thereof). In certain embodiments, the disclosed microphysiological platform can prevent the bulk leakage or transport of a biochemical microenvironment characteristic from a first microphysiological device or organ-on-a-chip model to a second microphysiological device or organ-on-a-chip model. The disclosed microphysiological platform prevents the bulk leakage by fluidically synthesizing a mixture that includes the concentrations of only a targeted set of compounds in the fluidic effluent of a first microphysiological device before introducing it to a second microphysiological device or a sequence of microphysiological devices. Such selectivity over constituents transported in a fluid is not possible in an alternative system that is configured to employ a direct fluid connection in which whole fluid (or a volumetric subset of said fluid) physically proceeds in bulk by pumping or directional flow in a sequential manner between a plurality of biological cultures connected in series.

In the devices, which possess direct fluid connections between two or more sequential biological cultures, any dissolved constituents in the sequentially propagating fluid mixture including cannot be isolated or removed without additional complex processes (e.g., chromatographic elution). Thus, the undesired constituents can flow sequentially through all of the biological cultures. Such bulk, the non-selective flow of fluid prevents the mimicry or reconstitution of physiological processes (e.g., the sequestration in the natural human body of certain local organ-specific biochemical microenvironments, biochemical signaling pathways, growth factors, morphogens, paracrine signaling compounds, or other biochemical constituents to just one tissue or a spatial subset of tissues in parallel with larger-scale or body-wide propagation of compounds such as endocrine or hormonal signaling mechanisms).

In certain embodiments, fluidic interconnects that are formed by digital fluid teleportation between a plurality of microphysiological devices permit the separation of short-range biological signaling or developmental cues within one tissue from the biological signals inherent to, secreted by, expected by, or required by other tissues, while still permitting selected signals to propagate by digital fluid teleportation, thereby overcoming limitations inherent to requiring one single "universal cell culture medium" that is compatible with all biological tissues cultured in a microphysiological platform or system.

In certain embodiments, the microphysiological devices can constitute biological entities. The microphysiological devices can include organ-on-a-chip models, a different growth medium used for each tissue or organ-on-a-chip model while superimposing the chemical signatures of compounds suspected of being involved in physiologically relevant organ-to-organ signaling. For example, for purposes of illustration and not limitation, a microphysiological platform can use the fluid addressing system to perfuse a "pancreas-on-a-chip" first microphysiological device with a first specific media formulation. The platform can sample the concentration of the insulin biologically secreted into the effluent of said media formulation by the first pancreas-on-a-chip microphysiological device and reconstitute said insulin concentration into a second media formulation with a fluidic synthesizer, and subsequently deliver this second media formulation to a "fat-on-a-chip" second microphysiological device in certain embodiments, this process of selectively transporting a subset of chemical constituents allows the effects of coupling specific biological compounds to be studied without the rest of the fluidic environment also leaking between the organs. In certain embodiments, the concentration of the constituent or constituents in a fluid transported by digital fluid teleportation can be derived from one or more of the following: a physical measurement, an algorithmic manipulation of physical measurement, a predicted value, or an arbitrary value.

In certain embodiments, the disclosed system can amplify the concentrate on of a plurality of constituents in a measured signal to overcome proportionality limitations between accurate relative sizing of cultured biological tissues. For example, when the physical volume or cellular quantity of a biological tissue cultured in a first microphysiological device is insufficient to recapitulate the physiological or desired concentration profiles of a specific chemical entity resulting from biological secretion, biochemical modification, absorption, metabolism, or other biological dynamic process affecting the concentration of the dissolved chemical compounds, the measured quantities of secreted or absorbed product by the microphysiological device can be mathematically transformed or scaled up or down, linearly or nonlinearly or with a lookup table, during the operation of the fluidic synthesizer to comply with or mimic a physiological range or the desired target range. For example, individual pancreatic beta cells can release the same quantities of insulin in a microphysiological device as they can in the human body. However, there can be a circumstance in which a smaller quantity of pancreatic islet beta cells in a pancreas-on-a-chip microphysiological device cannot secrete the same physiologically relevant quantity of insulin in response to increased glucose concentrations in the media as the concentration produced in the human pancreas. A fat-on-a-chip microphysiological device coupled directly or by digital fluid teleportation to the pancreas-on-a-chip device and exposed to said insulin cannot induce sufficient glucose uptake to cause a significant change in the glucose content of the media. In this example, by amplifying both the detected concentration of secreted insulin and the corresponding decrease in glucose in the media when instructing the fluidic synthesizer, the two organ-on-a-chip microphysiological devices can be coupled in a physiologically relevant manner despite limitations to their size in certain embodiments of a microphysiological device.

In certain embodiments, the disclosed system can recreate a specific continuous fluidic composition including a plurality of chemical compounds and their target concentrations as a function of time, at one or more specified locations, and synthesize said fluidic composition simultaneously or sequentially to said locations. In certain embodiments, by leveraging digital fluid teleportation to pass fluidic composition data over communications networks including the internet, the disclosed system can facilitate the collaborative investigation of multi-tissue dynamics using resources and microphysiological platforms (and the microphysiological devices therein) that are housed in different facilities. In certain embodiments, multi-laboratory, multi-institutional, or even multi-national collaborative efforts can be achieved through the transduction and subsequent digital fluid teleportation of effluent composition from a microphysiological device into a digital signal, the transmission of that signal to a plurality of microphysiological platforms, and transduction of that signal to a fluid mixture using a fluidic synthesizer. Teams of experts in the distinct organ or tissue systems can digitally interconnect their tissue models together to form a human body model that spans the globe. For purposes of illustration and not limitation, a beating heart-on-a-chip in France can branch to perfuse a lung-on-a-chip model in Pennsylvania and a kidney-on-a-chip at a laboratory in California, which can, in turn, be coupled to a liver model in Australia, and so forth.

Example System

As described above with references to FIGS. 2A and 2B, the disclosed subject matter provides hardware-level components for operating and controlling the microphysiological platform and its components including (without limitation) microphysiological devices. These described components can be replaced, rearranged, modified, and re-engineered to accommodate any possible variations of the system.

Figure 14:
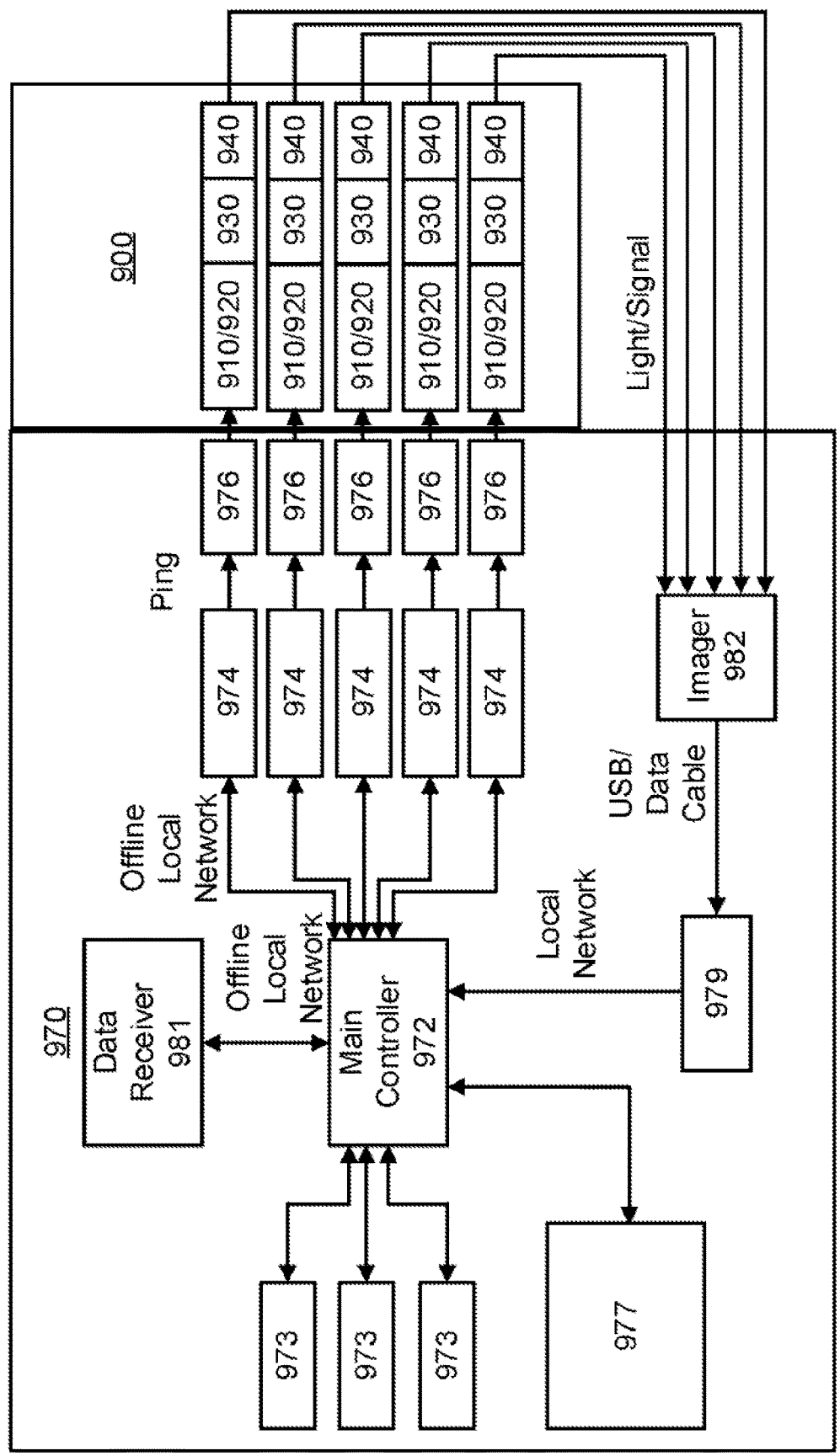
FIG. 14 is an illustration of an exemplary system hardware architecture of a microphysiological system including multiple microphysiological platforms, according to an embodiment.

FIG. 14 illustrates an exemplary system hardware architecture of an embodiment of a control system 970 operating with multiple microphysiological platforms 900 and various external devices and system. As shown, the control system 970 includes a main controller 972, web clients 973, a fluid synthesizer controller 974, an addressing system controller 976, biolines servers 977, a networked PC 979, a data receiver 981, and an imager 982. As shown, the microphysiological platforms 900 include fluidic synthesizers 910, fluid addressing systems 920, microphysiological devices 930, and biosensors 940. Main controller 972 can run fault-tolerant control system software that can, in certain embodiments, synchronize one or more of the following, digital fluid teleportation, fluid coupling, data acquisition, fluidic control, pneumatic control, system monitoring, environmental monitoring, experimental feedback, user interaction, automatic responses to nominal or fault states, environmental climate control, data transmission, web server operation, communication with additional microphysiological platforms, and synchronization with additional microphysiological platforms. In certain embodiments, the main controller 972 can serve a web browser-based user interface to local users' computers, laptops, and/or portable devices. In certain embodiments, the user interface to the microphysiological platform's control system can run in a web browser in order to be compatible with a variety of platforms, be they mobile or traditional desktops, as long as they have a web browser. In certain embodiments, a web-based user interface can remove the bottleneck of requiring multiple users to share a single physical computer (e.g., a master control system itself). In some embodiments, the core software can run on the main controller 972, and users can use or log in to lightweight user interfaces or user clients on their own devices (e.g., via the web client 973). In certain embodiments and without limitation, users can utilize the user interface to do one or more of the following: design new experiments, implement or sequence the methods required in new experiments, define microphysiological device experiments, modify existing experiments, monitor acquired data, export data, export graphical elements or analyses including plots of data, and manage digital fluid teleportation connections.

In some embodiments, fluidic synthesizer controllers 974 and/or addressing system controllers 976 can include shift registers for port expansion that can be used for the real-time control of the pneumatic valves on the microphysiological devices 930. The fluidic synthesizer controllers 974 and/or addressing system controllers 976 can include industrial microcontrollers that can drive the relays for valve actuation and motion control (e.g., the imager 982) in response to higher-level control commands from the main controller 972. In some embodiments, the imager 982 can include an SPR imaging camera. In some embodiments, the imager 982 can include a laser scanner. For example, each microphysiological platform 900 can have 14 valves (each 4-port, 2-position) for the fluid addressing systems 920 (7 on each side) and 48 valves (each 3-port, 2-position) for the fluidic synthesizers 910 (1-24 on each side). In non-limiting embodiments, each microphysiological platform 900 can have 124-way/2-position valves plus 4 3-way/2-position valves; or 28 3-way/2-position valves. The latter configuration can allow the entire fluid addressing system 920 to be depressurized, which can allow all connected microphysiological devices 930 to be washed simultaneously. To drive the fluidic synthesizer 910, the microphysiological platform 900 can have as many 3-way/2-position valves as there can be connected mixture compounds. The connected compounds can be mixed at different ratios, or mixed at the same ratio. In some embodiments, two inlet solutions to the fluidic synthesizer 910 that can be mixed at the same ratio can be driven by one valve. In some embodiments, the fluidic synthesizers 910 can be expanded to accommodate more than 25 distinct mixture inputs per side. Since the required number of valves increases accordingly, latching shift registers can be chained to create a parallel array of control pins for the pneumatic valves.

In certain embodiments, the biosensors 940 at each organ-sensor unit can be transduced to a digital signal by the imager 982. The imager 982 can be connected to the networked PC 979, whose purpose is to transmit this transduced data to the main controller 972. In some embodiments, the networked PC 979 can include a small computer. In some embodiments, the networked PC 979 can include a laptop. The main controller 972 can read the output directly from the imager 982 when the additional real-time data processing requirements do not cause any slowdown or interference. A connection from the local main controller 972 to software servers (e.g., biolines servers 977) connected to the internet, cloud, or software-as-a-service (SaaS) system can be established for software license management, access to virtual tissue libraries, and real-time digital interfacing with off-site organ devices. Multiple microphysiological platforms 900 can be operated locally by a single main controller 972. When interfacing with off-site microphysiological platforms 900 and microphysiological devices 930 (platforms and devices operated by separate master control servers), data transmission can be mediated by the internet or cloud software servers. These technologies can allow improved-quality and easy-to-establish connections that can be maintained and monitored for events including, without limitation, connection dropouts or to predict bandwidth requirements, load balancing considerations, and data traffic routing optimization.

The disclosed subject matter provides software applications and technologies for operating the microphysiological platform 900. The disclosed biological virtualization technologies for statistical data processing and modeling virtual tissues and virtual organs can be integrated into a main controller 972 and be made configurable in a user client. As a nonlimiting example, the disclosed system can have a main controller 972 which can provide a fault-tolerant software for synchronizing and managing all operations of the microphysiological platform 900 in real-time. The software of the main controller 972 can determine pulse-width modulation (PWM) biases in fluidic synthesizers 910 based on user settings and transduced signals from the biosensors 940. As a nonlimiting example, the open-close cycling of valves for flow metering in a manner controlled by pulse width modulation can allow proportional control over flow rates through microfluidic valves (e.g., in the fluid addressing system 920 or the fluidic synthesizer 910). In certain embodiments, the PWM can be applied at a certain frequency to permit full opening and closing cycles in a valve. For example, where 0% pulse width can correspond to an always-closed valve and 100% pulse width can correspond to an always-open valve, a valve with a 60% pulse width can remain open for twice longer in each pulse cycle than a valve with a 30% pulse width. The rate of fluid flow can be controlled by adjusting the opening period. In certain embodiments, the PWM can be applied at a certain frequency to preclude the full actuation (closing or opening) of a valve between the signal-high and signal-low portions of a pulse. For example, a sufficiently high PWM frequency can permit such an elastomeric valve to flutter or undulate closely about a steady-state position, whereby a valve with a 60% pulse width can maintain a steady-state position that allows twice the flow of a valve with a 30% pulse width. In certain embodiments, the fluid-filled fluid control lines can be integrated into the microfluidic valving of the microphysiological platform 900 and driven using syringe pumps or peristaltic pumps.

The software of the main controller 972 can control the microphysiological platform 900 by transmitting commands to microcontrollers (e.g., the fluidic synthesizer controller 974 and/or the addressing system controller 976) to activate specific microphysiological device 930 addresses in the fluid addressing system 920 for monitoring flow rates, fluid levels, and pneumatic line pressures. In certain embodiments, the software of the main controller 972 can control the microphysiological platform 900 to perform data processing, host a local web server for web client logins, package data for transmission to local web clients (e.g., a data receiver 981, a local data repository, and local data servers), and maintain a connection to any one or more of data and control servers. In certain embodiments, National Instruments LabView can be used for control software implementation. In certain embodiments, other programming languages can be used for control software implementation, including one or a combination of the following without limitation: C++, C#, P thon, Java.

In certain embodiments, the control system 970 can detect leaks, clogging, or a combination of leaks and clogging of the microphysiological platform 900 by polling the data on an outlet flow meter and alert users by email, text message, or other direct or indirect communications method. In certain embodiments, upon detecting leaks or clogging events, the immediate response of the control system 970 can be configurable (e.g., suspend flow into the clogged microphysiological device 930, suspend flow across the entire device 930, pause the experiment, or continue as normal).

In certain embodiments, the control system 970 can provide user client software. For example, users of the control system 970 can design, monitor, and process experiments on a software client that can be served by the main controller 972 or by an internet server and run in their web browser. In certain embodiments, the user client software can run as a local application on a computer (e.g., the networked PC 979) or as a distributed application among a plurality of computers. In certain embodiments, the software can present aspects of the ongoing experiments (including, without limitation, portions of measured data) alongside a heads-up display of the current status of the fluid addressing system 920 on the device, shown alongside the two columns of microphysiological devices 930. In certain embodiments, users can click on individual microphysiological devices 930 to expand a settings box. In certain embodiments, each microphysiological device 930 can be customized (e.g., named, given a distinctive icon, visual feature, visual characteristic, or a combination thereof). In certain embodiments, each microphysiological device 930 can have all of its sensor 940 and flow properties specified in the user interface. In certain embodiments, real-time data can be visualized in graphical form on a subpanel of the interface, allowing an at-a-glance summary of a microphysiological device's status. In certain embodiments, said user interface can allow accessory data to be imported and associated with a plurality of aspects of existing data, including timestamps or sensor recordings.

In certain embodiments and for purposes of illustration and not limitation, in response to seeing unexpected sensor readings, a user can image a microphysiological device 930 in question, and then associate that image as an accessory data file to the corresponding time points of recorded sensor or platform operation for later analysis. In non-limiting embodiments, real-time data subpanel can be minimized. In certain embodiments, a digital fluid teleportation outline view can provide a visualization of connections between microphysiological devices 930 on a plurality of microphysiological platforms 900. In certain embodiments, the design of the interface can improve the functionality and the clarity of the obtained data by providing a visual aesthetic in the form of bold colors. In certain embodiments, the visual style of the user interface can complement the clarity of any presented data. Software produced by the disclosed subject matter can support alternative-colors as well as improved-contrast schemes to permit accessibility to colorblind or visually impaired users. In some embodiments, microphysiological devices 930 can be shown in a user interface as movable blocks, and synthesized fluidic connections can be established by dragging and dropping visual links or ties between the movable blocks. In certain embodiments, experiments can be designed in a user interface using graphical elements including blocks, lines, or curves. In certain embodiments, experiments can be designed by interaction with the microphysiological platform and platform software through a command-line interface (CLI).

In certain embodiments, the disclosed subject matter provides the internet-accessible software which can run on centralized software servers. In certain embodiments, the accessible internet software can manage communications between multiple microphysiological platform installations, client licensing and accounts, and provides access to a standard library of templates, optimized protocols, and virtual tissues as part of a subscription service. In certain embodiments, the disclosed system can operate across decentralized cloud platforms (e.g., Amazon's AWS and/or Microsoft Azure).

Screen Forward Implementation

Figure 15A:
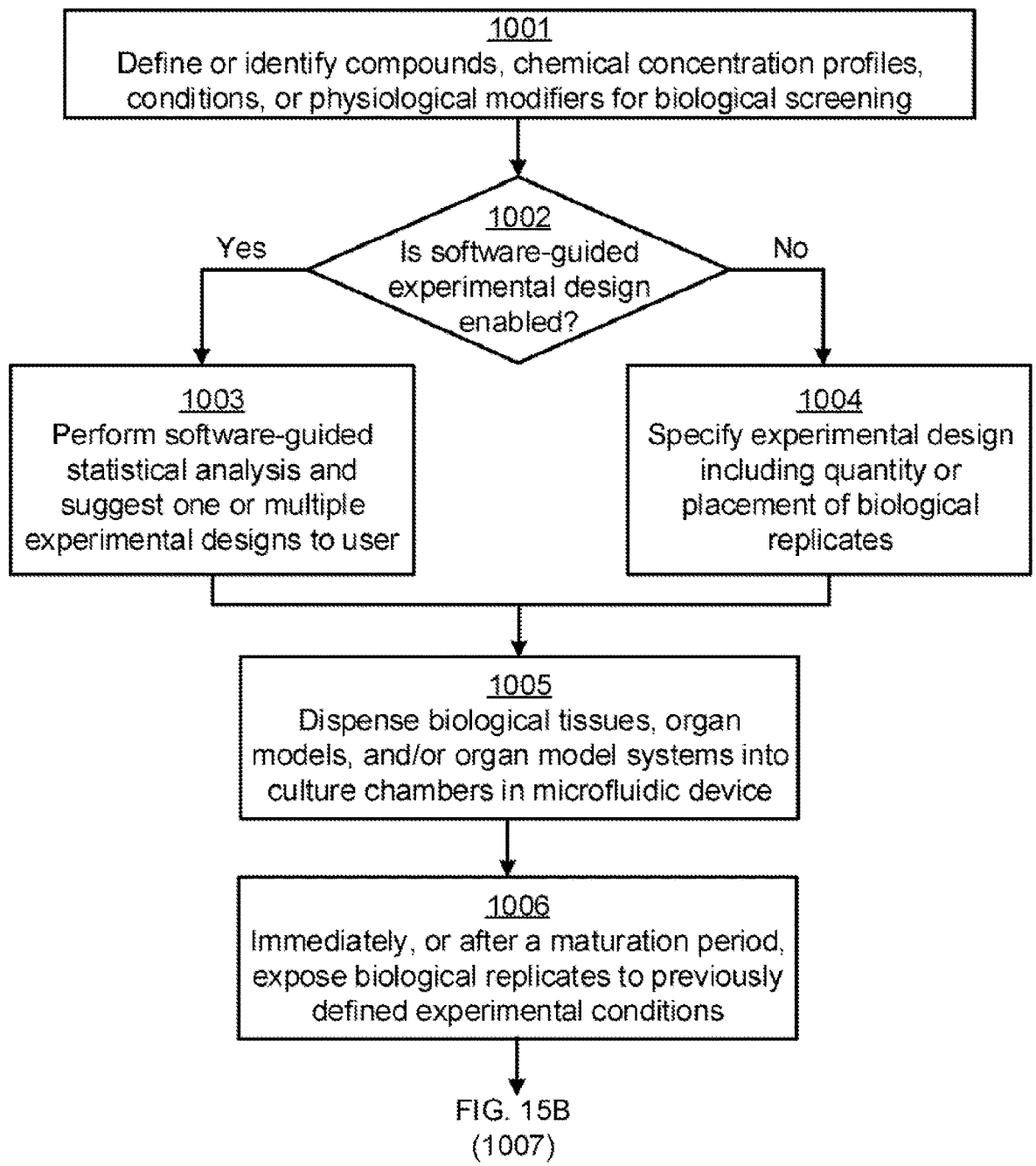
FIGS. 15A and 15B are flow diagrams illustrating a method of a screen-forward mode of fluid teleportation, according to an embodiment
Figure 15B:
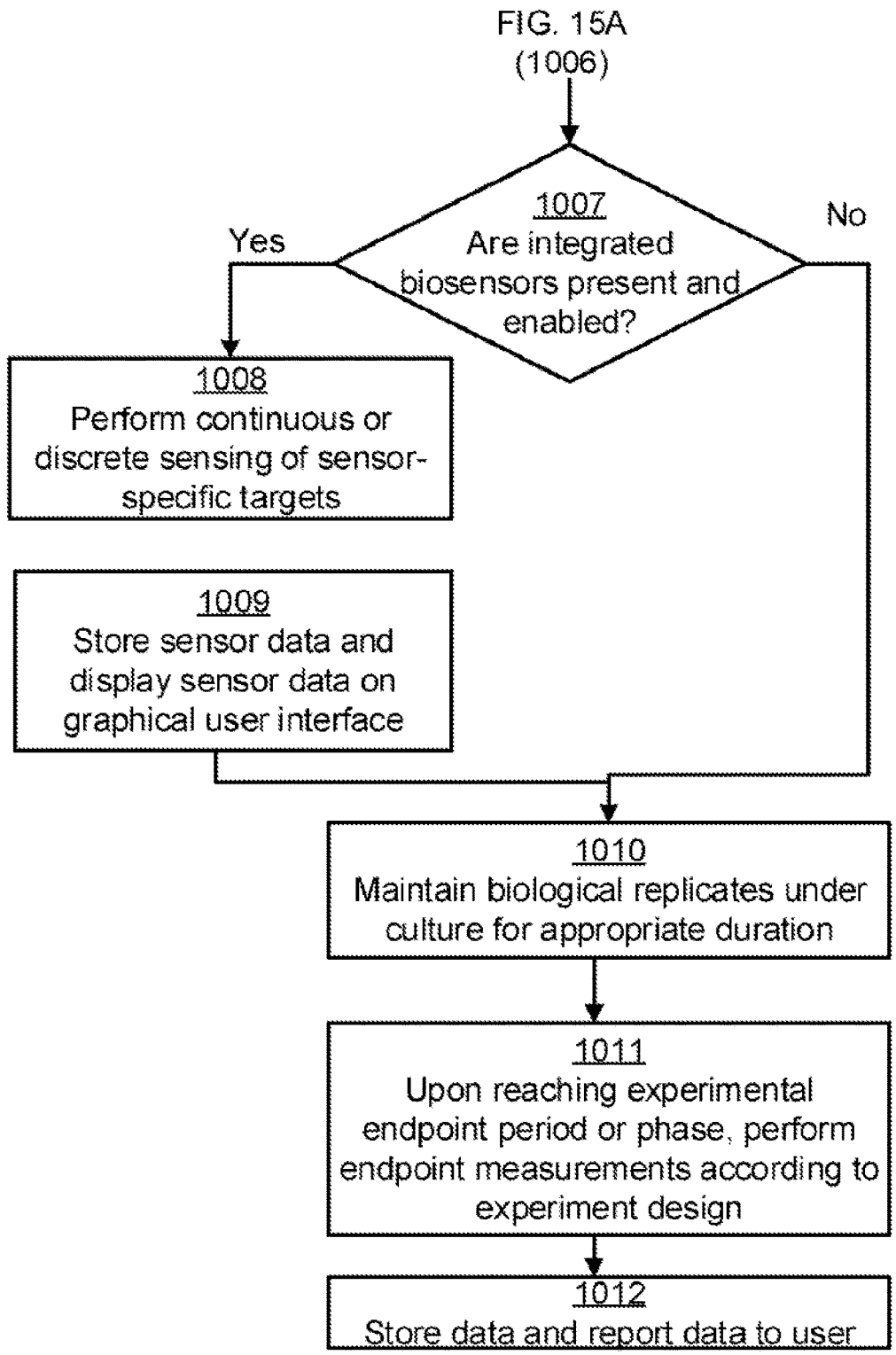
Figure 16A:
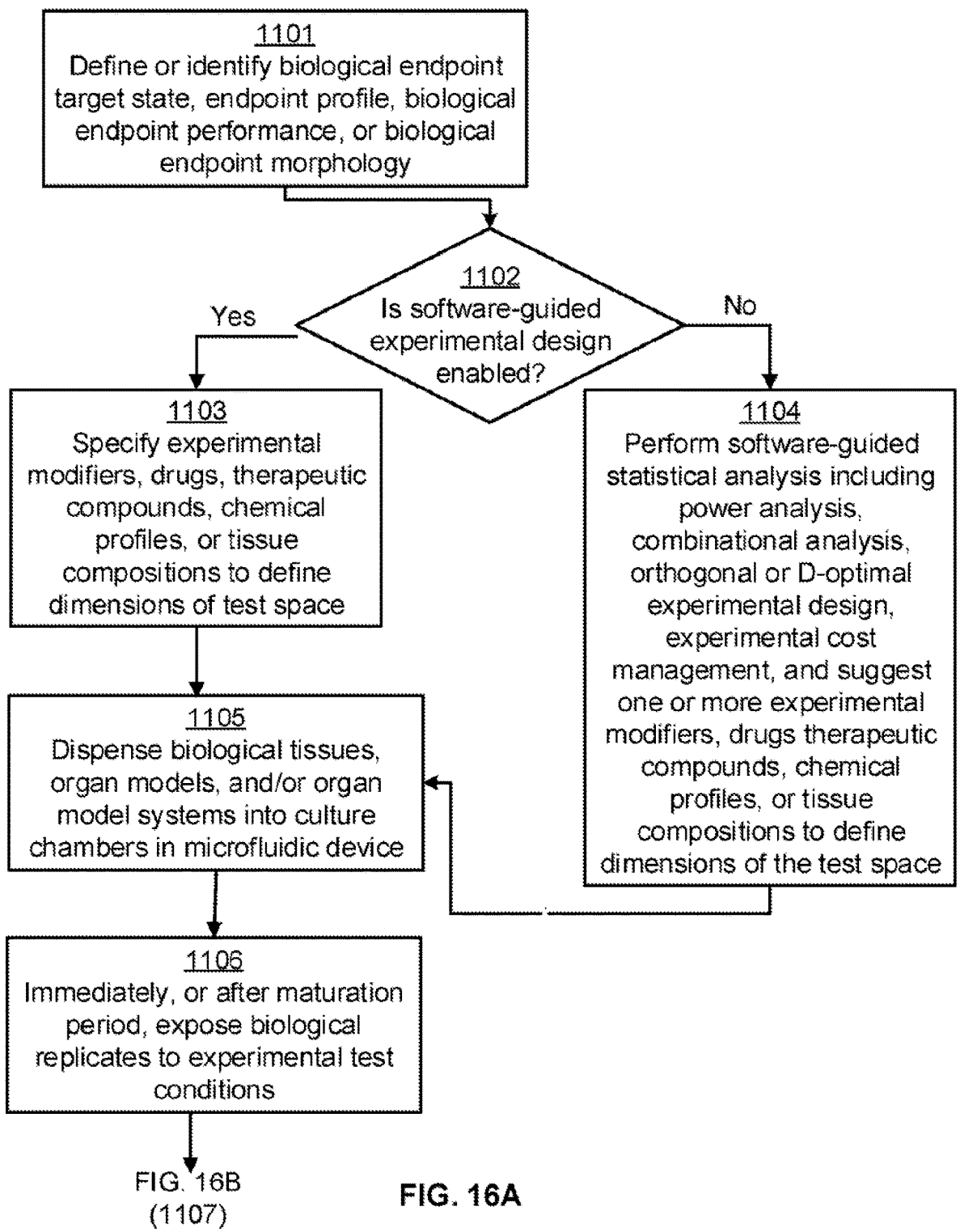
Figure 16C:
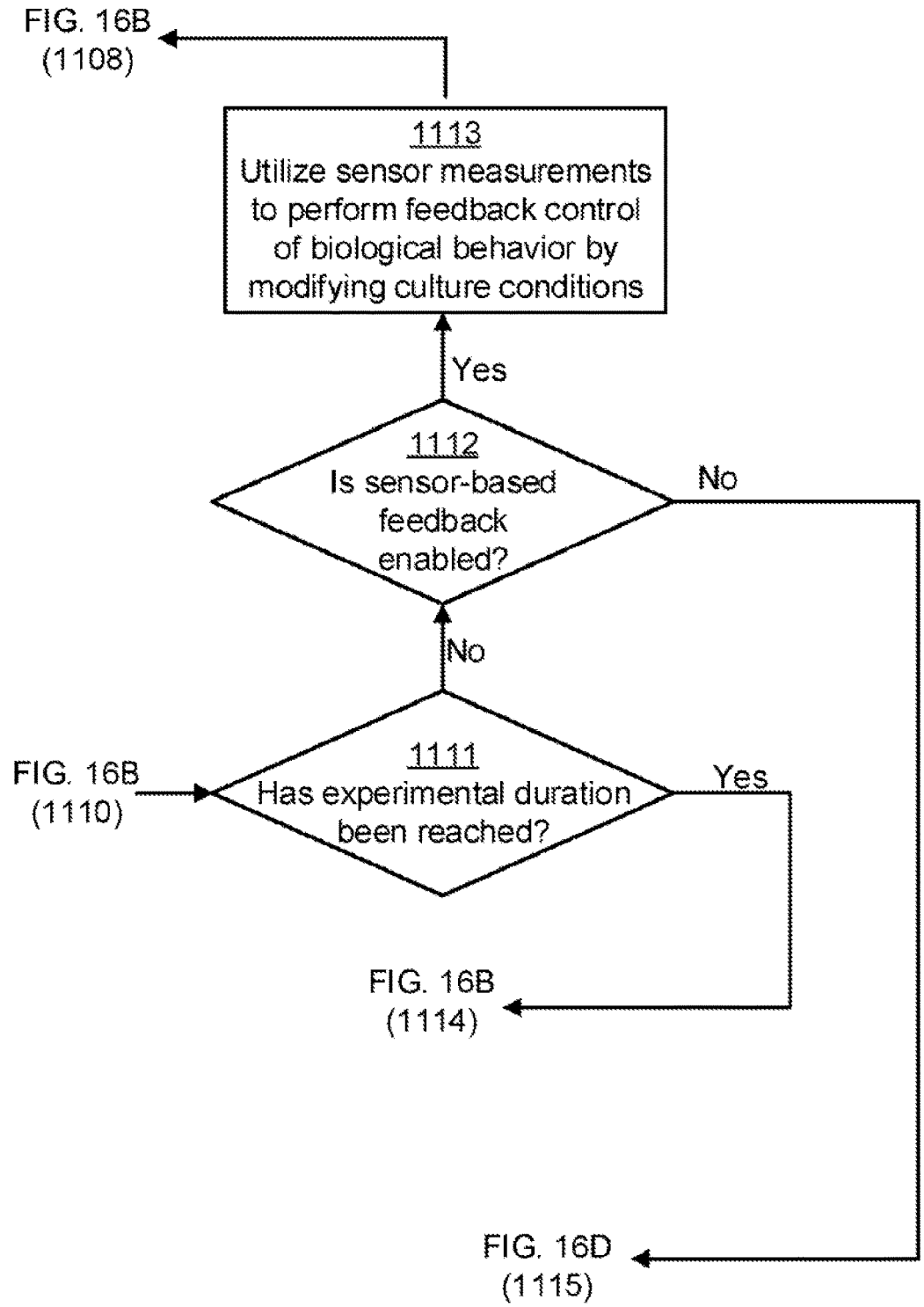
Figure 16D:
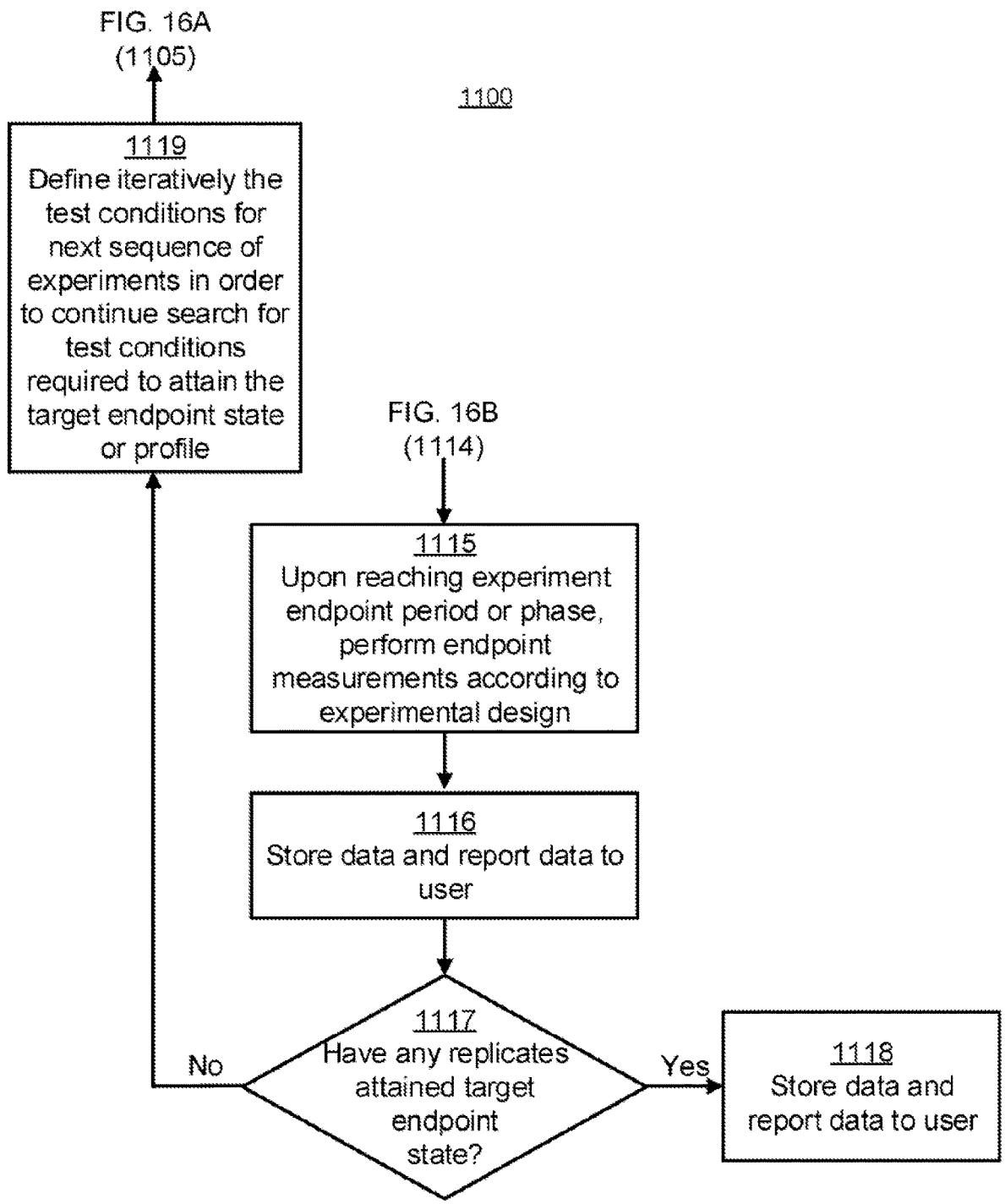

In some embodiments, the microphysiological platform and control system architectures described above can function collectively as a high-throughput screening system. The screening system can define one or more target conditions (e.g., chemical compounds, therapeutic drugs, treatments, and/or fluidic compositions) and identify responses of cultured tissues in microphysiological devices (e.g., the time-dependent responses and/or endpoint responses) which can result from the defined conditions. The screening process can be started from know-n conditions or externally applied condition profiles (e.g., a drug concentration profile that mimics dosing with meals) to identify the endpoints that result from each such condition (e.g., a "screen-forward" approach). An example of such a screen forward approach is illustrated in the flow chart of FIGS. 15A and 15B, depicting method 1000. For example, as shown in FIGS. 15A and 15B, compounds, chemical concentration profiles, conditions, and/or physiological modifiers can be defined for biological screening, shown in 1001. If an exemplary system includes a software-guided experiment design as determined in 1002, software-guided statistical analyses (e.g., power anal sis, combinatorial or factorial analysis, orthogonal experiment design. D-optimal experiment design, and/or experiment cost management) can be performed, shown in 1003. Certain experimental designs (e.g., quantity or placement of biological replicates in microphysiological devices) can be determined without the software-guided experiment design, shown in 1004. Then, based on the experimental design, biological replicates (e.g., tissues, organ models, organ model systems, or a combination thereof) can be dispensed into microphysiological devices of the exemplary microfluidic system, shown in 1005. The biological replicates can be, immediately or after a maturation period, exposed to the pre-defined experimental conditions (e.g., certain concentrations of nutrients, drugs, bacteria, viruses, gene editing agents, or a combination thereof), shown in 1006. Integrated biosensors, if present and enabled, as determined in 1007 of the exemplary system can perform continuous or discrete sensing of targets (e.g., DNA, RNA, proteins, growth factors, hormones), shown in 1008. The detected results and data can be stored and displayed on the graphical user interface, shown in 1009. The biological replicates can be cultured for the pre-determined period, shown in 1010. If integrated biosensors are not determined to be present and enabled in 1007, 1004 and 1009 are skipped and the method 100 proceeds to 1010. Upon reaching the experiment endpoint period, endpoint measurements can be performed according to the experiment design, shown in 1011. For purposes of illustration and not limitation, said endpoint measurements can include one or a combination of the following: staining by immunohistochemistry (IHC), immunocytochemistry (ICC), tissue extraction, microscopy, RNA or DNA isolation, transcriptomics, proteomics, and cell isolation. The measured endpoint data can be stored and reported to a user, shown in 1012.

In non-limiting embodiments, the disclosed system can screen multiple conditions. Various dynamic and continuous conditions (e.g., a drug concentration profile, and/or a pre-determined drug concentration based on drug partition models) can be formulated in real-time by the disclosed fluidic synthesizer. In certain embodiments, the disclosed system can test one or a combination of dynamic and continuous conditions for screening. As a nonlimiting example, the disclosed system can determine the effects of different concentrations of a vascular endothelial growth factor (VEGF) receptor inhibitor on tumor angiogenesis, the effects of dosing a VEGF inhibitor at different frequencies or concentrations on tumor angiogenesis, or the effects of dosing said VEGF inhibitor at a dynamic concentration profile that mimics metabolism and/or transport in a human body.

Screen Backward Implementation

In certain embodiments, the disclosed system can perform a screening study or screening experiment by identifying known endpoints and finding causative conditions that generate or produce said endpoints. The disclosed system can define a target endpoint state and search a plurality of initial conditions or condition profiles that can produce the target endpoint state through one or a succession of iterative refinements (i.e., a "screen-backward" approach). For example, FIGS. 16A-16D depict a method 1100, in which the target biological endpoint target state, profile, performance, and/or morphology can be defined, shown in 1101. If an exemplary system can include a software-guided experiment design as determined in 1102, software-guided statistical analyses (e.g., power analysis, combinational analysis, orthogonal experiment design, D-optimal experiment design, experiment cost management, experimental modifiers, drugs, therapeutic compounds, chemical profiles, and tissue compositions to define dimensions of the test space) can be performed, shown in 1103. Certain experimental designs (e.g., experimental modifiers, drugs, therapeutic compounds, chemical profiles, and/or tissue compositions) can be determined without the software-guided experiment design, shown in 1104. Then, based on the experimental design, biological replicates (e.g., tissues, organ models, organ model systems, or a combination thereof) can be dispensed into microphysiological devices of the exemplary microfluidic system, shown in 1105. The dispensed biological replicates can be, immediately or after a maturation period, exposed to the pre-defined experimental conditions (e.g., nutrients, drugs, bacteria, viruses, and/or gene editing agents at one or a range of concentrations), shown in 1106. If integrated biosensors are present and enabled, as determined in 1107, the method 1100 can include performing continuous or discrete sensing of targets (e.g., DNA, RNA, proteins, growth factors, hormones) at 1108. The detected results and data can be stored and displayed on the graphical user interface, shown in 1109. As shown in 1110, 1111, and 1112, the method of a screen-backward mode includes determinations of whether integrated biosensors are present and enabled, whether the experimental duration has been reached if defined), and if sensor-based feedback is enabled, respectively. If both sensor-based feedback and integrated biosensors are enabled, and the experimental duration has not been reached, the method 1100 includes utilizing sensor measurements to perform feedback control of biological behavior by modifying culture conditions, shown in 1113. This loop continues until the experimental duration is reached. In non-limiting embodiments, the biosensors can provide real-time feedback based on the detected data regarding experiment duration and/or biological behavior. The detected data can be used to modify the culture conditions, shown in 1112. The biological replicates in microphysiological devices can be cultured for the pre-determined period, shown in 1114. The method 1114 can occur once the experimental duration has been reached or if integrated biosensors are not present and enabled. Upon reaching the experiment endpoint period or phase, endpoint measurements can be performed according to the experiment design, shown in 1115. The measured endpoint data can be stored and reported to a user, shown in 1116. If any replicates can attain target endpoint state, shown in 1116, the test conditions required to attain the target endpoint state can be presented to the user, shown in 1118. Otherwise, the disclosed system can repeat the screen-backward procedure in a sequential or iterative manner until the target endpoint state can be attained via 1119, looping back to 1105. As a nonlimiting example, various test conditions can be iteratively defined for the next sequence of experiments. The test conditions can be defined automatically or semi-automatically with the software guidance, or by one or more manual inputs, requirements, and/or constraints.

In non-limiting embodiments, the disclosed system can define a state with limited tumor angiogenesis and limited cell death from systemic toxicity, and then screen for the time-dependent dosing condition of VEGF inhibitor that results in this intended endpoint. In non-limiting embodiments, the disclosed system can be used for biological screening procedures. For example, the system can be employed on tissues cultured from a reporter cell line of human pancreatic beta cells that expresses fluorescent protein during insulin secretion. The target endpoint state can be defined as a specific time-dependent fluorescent intensity profile (which can correlate to a time-dependent insulin release profile) in response to the exposure to increased glucose concentration in the fluid mixture. The disclosed system can iteratively screen for the combination and time-dependent profile of culture conditions (e.g., from a set of growth factors, glucose, and drug compound precursor solutions) that can produce this target endpoint response.

In certain embodiments, the disclosed screen-forward and/or screen-backward modes can be selected for the multi-device or multi-tissue models defined in microphysiological devices on one microphysiological platform or a plurality of connected microphysiological platforms. In the screen-forward or screen-backward modes, the target states or target conditions can be defined for multiple systems. For example, the screen-forward or screen-backward conditions or constraints can be applied for one tissue or for multiple tissues. The conditions or constraints can be defined as an ideal target range for some biological behaviors or biochemical reactions. In non-limiting embodiments, the conditions or constraints can be optimized as a cost function relating to the health of one tissue in terms of the other as a ranking of priority. For example, a target end-state that can prevent the behavior in one tissue while minimizing effects of drug toxicity in another tissue can be defined for the screen-forward and/or screen-backward modes.

Figure 17A:
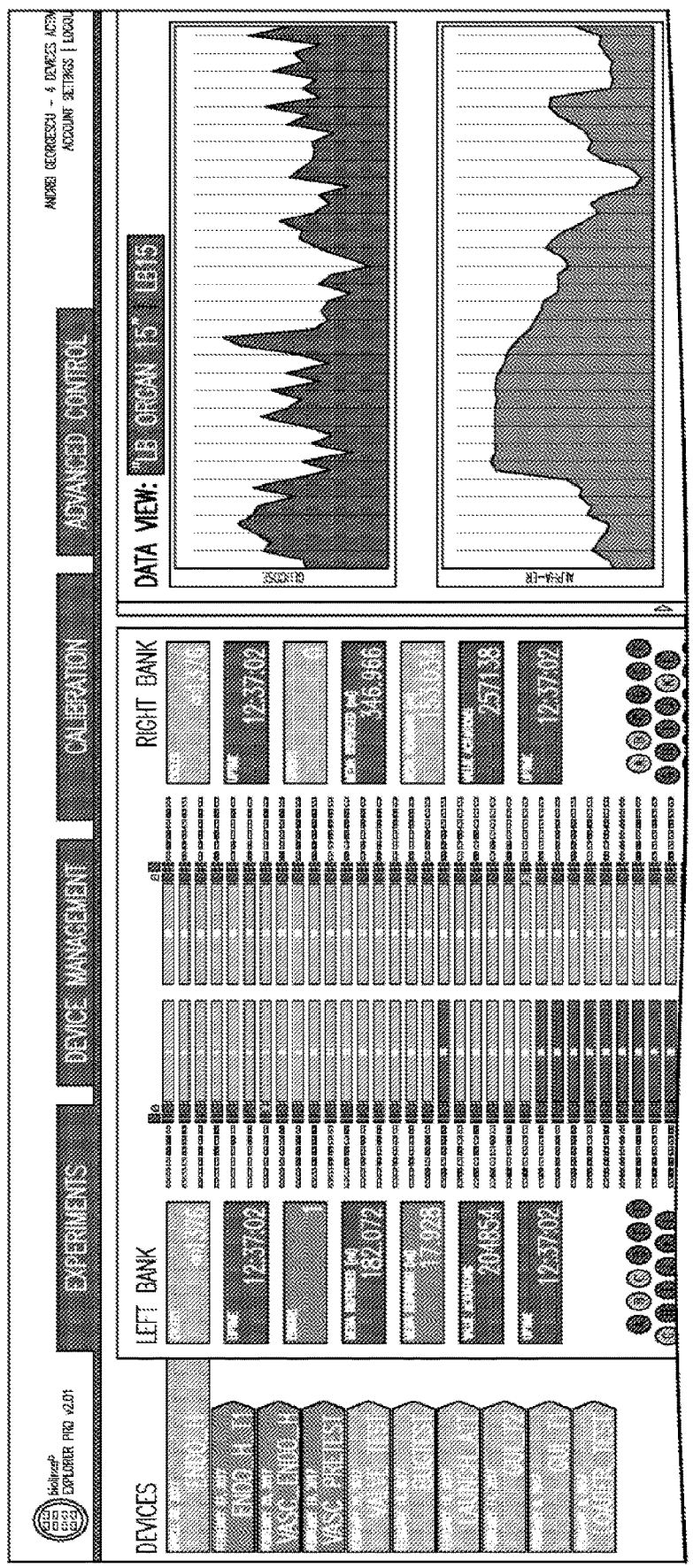
FIG. 17A is an illustration of an exemplary user interface view of system software.
Figure 17A:
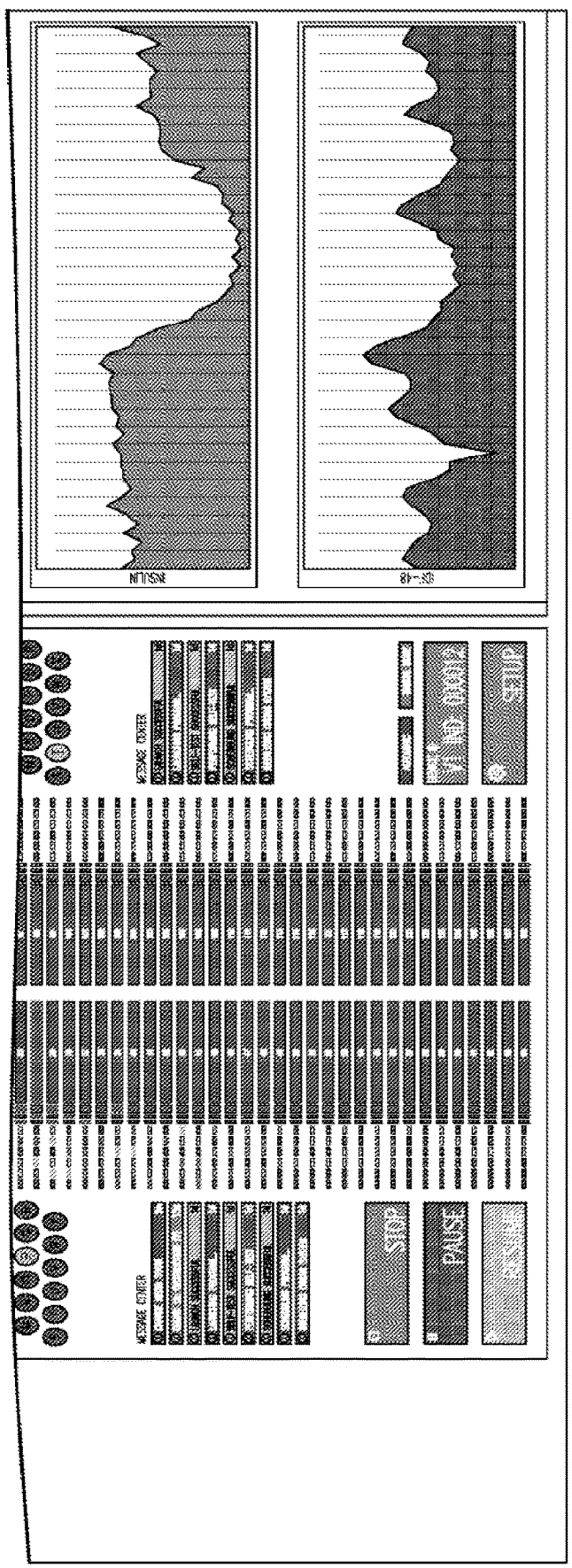
Figure 17B:
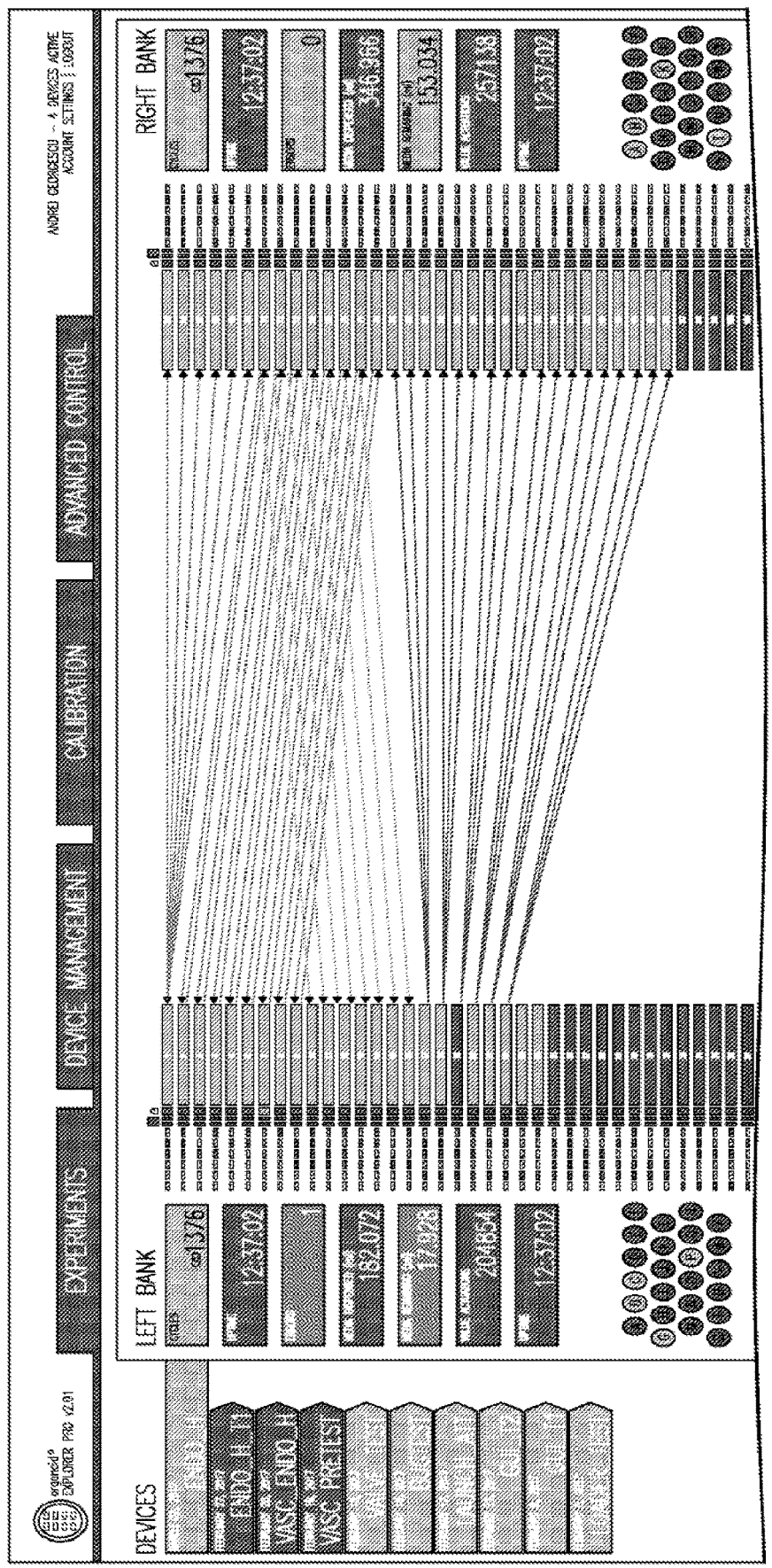
FIG. 17B is an illustration of exemplary microphysiological device interconnection visualization, used in this exemplary embodiment to illustrate active fluid teleportation connections, according to an embodiment.
Figure 17B:
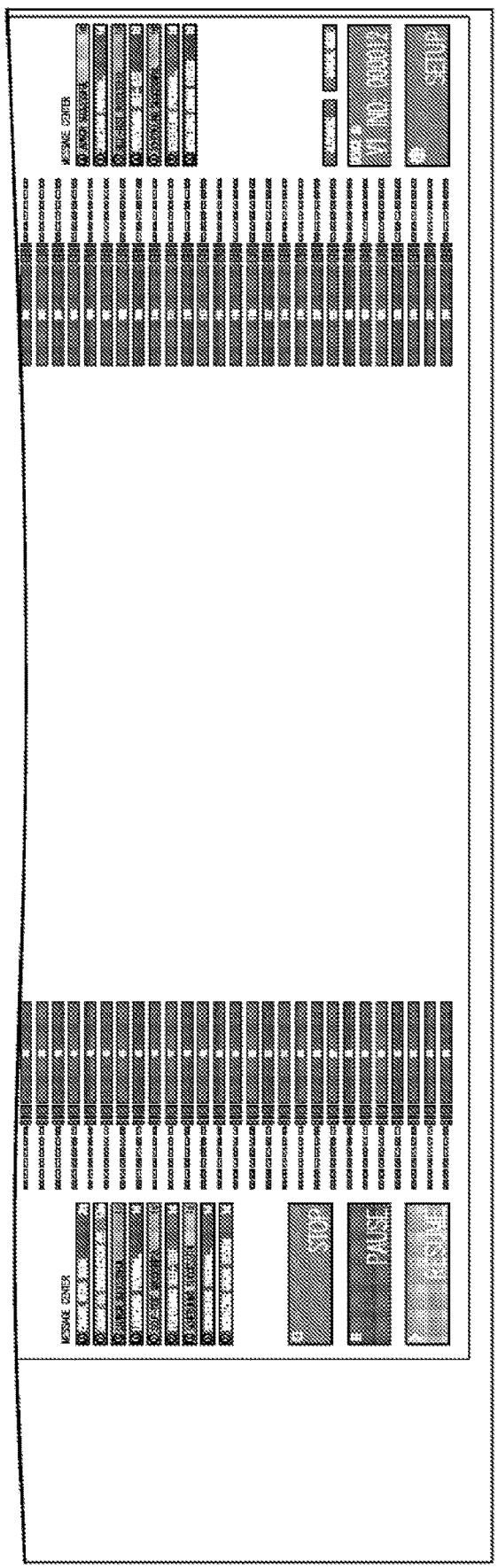

In certain embodiments, a user interface can be designed as shown for purposes of illustration and not limitation in FIG. 17A and in FIG. 17B. In certain embodiments, the operational mode of the microphysiological platform can influence the elements, layout, and functionality of the user interface Virtual Tissues The disclosed subject matter provides systems and methods for developing and integrating "virtual tissues" in certain embodiments. When the responses of a microphysiological device (e.g., microphysiological device 130, as described above with reference to FIG. 1, a particular biological entity or biological tissue) to a given input space of possible combinations of stimuli can be characterized, a physical embodiment of that particular microphysiological device can be replaced with a virtualized, simulated representation based upon predicted or pre-established behaviors or responses. For example, any of the devices described above with reference to FIGS. 11A to 11D and FIG. 12 can include virtual or simulated devices (e.g., virtual tissue representations). In certain embodiments, this virtual device (e.g., virtual tissue) is simulated computationally by making predictions or statistical models for expected behavior based on data collected from observations of physical embodiments of the device being simulated (within microphysiological devices, in animals, in humans, as gathered from the scientific literature, or a combination thereof). In certain embodiments, this virtual device is simulated computationally based on heuristics, rules, or datasets. In certain embodiments, this virtual device is simulated based on speculative predictions. The virtual device's digital outputs can be similar or identical to the outputs measured in sensors from the corresponding physical version for which the virtual device was substituted. Accordingly, such a virtual device can be coupled to one or a plurality of additional physical microphysiological devices or additional virtual devices, and the responses, absorptions/secretions, and behaviors of the first virtual device can be modeled computationally.

In certain embodiments, biological behavior of a target tissue can be predicted by using a virtual tissue, including by creating a statistical predictive model of a target tissue based on physical observations of the target tissue and applying the statistical predictive model to predict a modification of a first fluidic solution. The modification can comprise a chemical or a biological change that is induced when the first fluidic solution is incubated with the target tissue to produce the second fluidic solution. In non-limiting embodiments, the first fluidic solution can be an input of the virtual tissue, and the second fluidic solution can be an output of the virtual tissue. In some embodiments, a first continuous mathematical function or continuous measurement can be used as the input to the virtual tissue and a second continuous mathematical function can be generated as a corresponding output. For example, a continuous mathematical function can be a continuous relationship with time. For purposes of illustration and not limitation, a continuous input function to a virtual tissue for a compound "A" whose concentration increases linearly as a function of time can be written as $A(t)=A_0 t$, where "A" is a constant defining the rate of accumulation, if said virtual tissue secretes a compound "B" such that compound "B" is always maintained at twice the concentration of "A" then the virtual tissue's continuous output function over for compound "B" would be $B(t)=2 A(t)$, which can also be written as $B(t)=2 A_0 t$. In certain embodiments, symbolically linking the input and outputs of the virtual tissues in this manner allows these equations to be calculated rapidly though numeric or analytical solvers, to produce a simulated outcome. In certain embodiments, the output data can be generated by utilizing an optional mathematical transformation of numerical values produced by the virtual tissue output.

In certain embodiments, predicting a biological behavior of a target tissue using a virtual tissue can further include coupling at least two virtual tissues by connecting the output of a first virtual tissue to the input of a subsequent virtual tissue. In non-limiting embodiments, a network of at least three virtual tissues can be established. Each virtual tissue can receive at least one input and generate at least one output. Each of the at least one output can be connected to zero or at least one virtual tissue inputs. In non-limiting embodiments, each of the at least one input and output can be mathematically transformed before or after connecting to a virtual tissue. The at least one input and output data for each virtual tissue can be recorded, either discretely or continuously over some duration of time within the scope of the experiment.

In certain embodiments, predicting a biological behavior of a target tissue using a virtual tissue can further include identifying constituents of the second fluidic solution calculated by the virtual tissue output and synthesizing a fluidic solution based on the identified constituents using a fluidic synthesizer.

In certain embodiments, the responses, absorptions/secretions, and behaviors of multiple virtual tissues can also be modeled computationally in said fashion. In certain embodiments, the observations can be derived from existing data in the scientific or medical literature. In certain embodiments, the observations can be derived from measurements taken in a microphysiological platform. The observations can be used to predict the behavior of a biological entity (that, in certain embodiments, can be cultured in a microphysiological device), and allow for the biological entity to be simulated as a virtual tissue rather than physically deployed within a microphysiological device. These models can range from being computationally simple (e.g., a virtual tissue can be embodied by a lookup table that maps the concentration of a single input factor or chemical concentration to a corresponding quantity of a second compound to secrete) to being computationally complex models based on statistical algorithms used in machine learning (see FIG. 18). In certain embodiments, for purposes of illustration and not limitation, the virtual tissue can be simulated by a neural network, by a decision tree, by an ensemble method of a plurality of machine learning methods, or by statistical inference. The transduced digital signal from a biosensor associated with a real biological entity being cultured in a microphysiological device can be the virtual tissue's input or a subset of the virtual tissue's inputs, and the virtual tissue's output can, in turn, be used as the digital input to the fluidic synthesizer that delivers the media mixture (containing the secretions of the virtual tissue) to the tissue being physically cultured. In certain embodiments, a plurality of virtual tissues can be coupled or linked to a plurality of virtual tissues.

Figure 18:
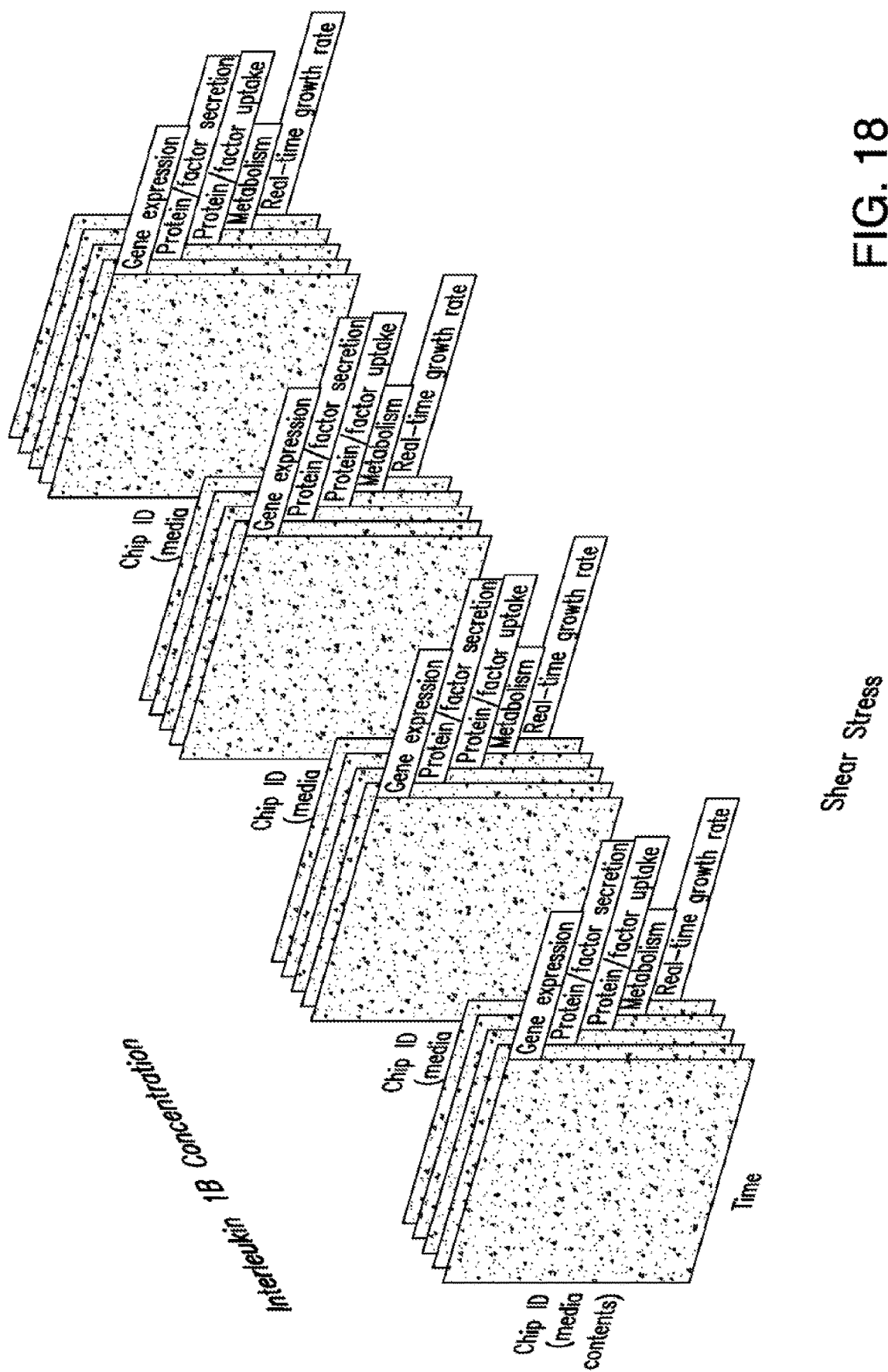
FIG. 18 is an illustration of exemplary data collection using a virtual tissue in accordance with the present disclosure.
Figure 18:
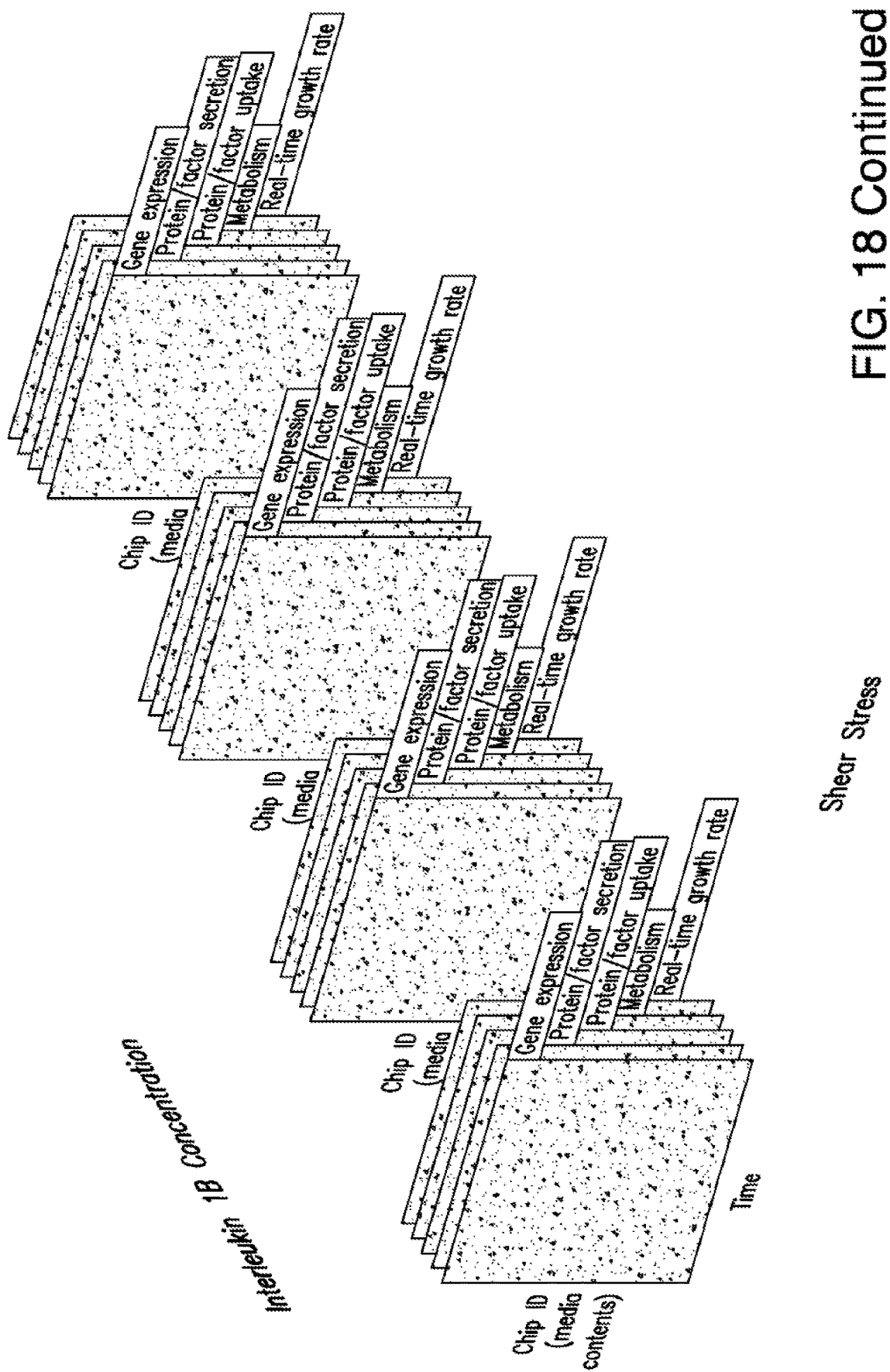
Figure 18:
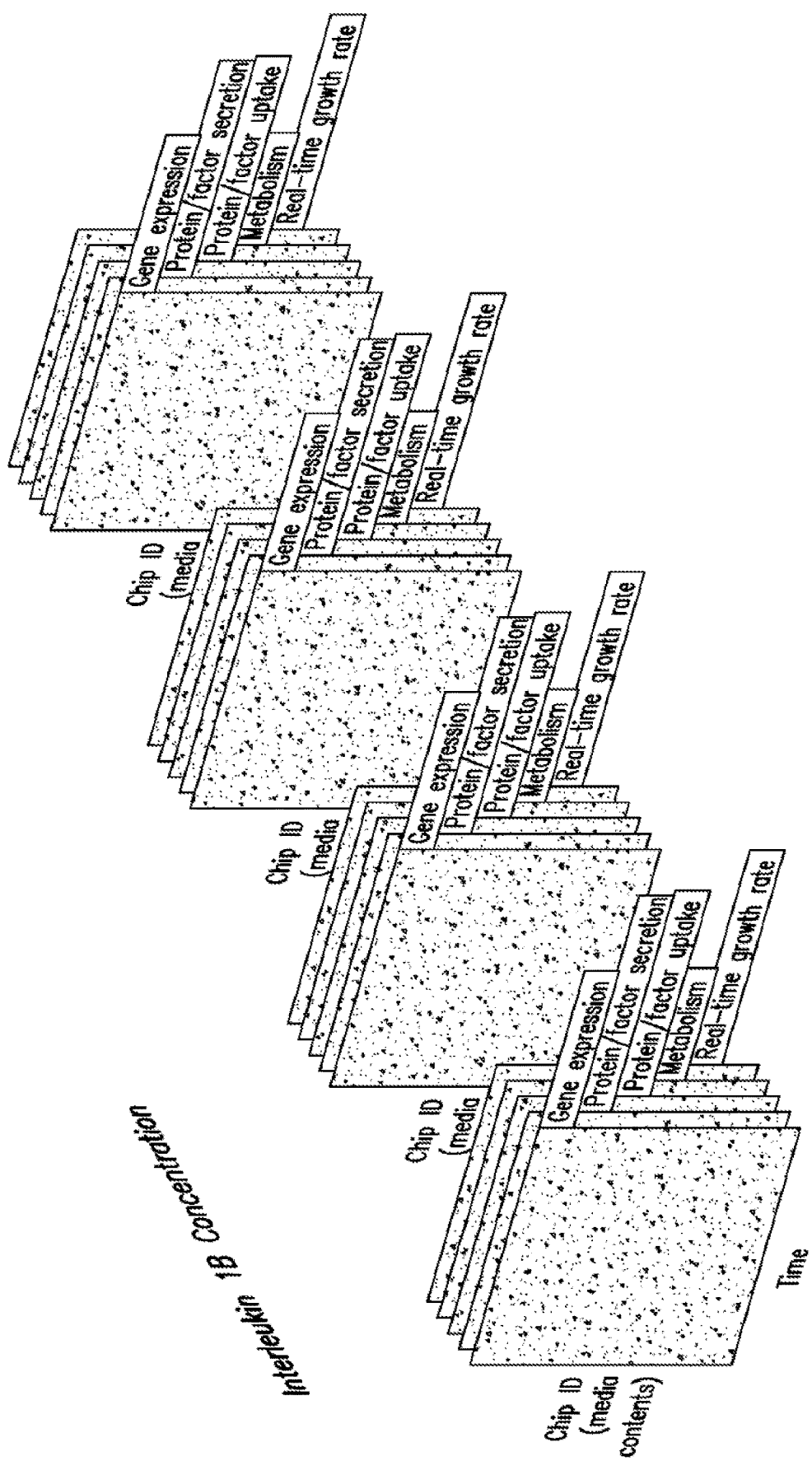

For example, as shown in FIG. 18, an organ-on-a-chip model cultured in a microphysiological device can be characterized by obtaining substantial amounts of data through the utilization of a microphysiological platform under a wide variety of culture conditions. Subsequently, based upon the collected data that maps input conditions to phenotype, behavior, and secreted factors and compounds, the dynamic responses of the cultured tissue in a given condition can be computationally predicted. In certain embodiments, the prediction method can use the interpolation of existing data to generate a prediction. In certain embodiments, machine learning or statistical learning techniques can be employed to generate a prediction. By replacing real tissue with a virtual tissue and digitally interfacing it to the fluidic inputs of real tissues' fluidic synthesizers or other virtual tissues' digital inputs, tissue virtualization can be realized. Accordingly, the disclosed virtual tissue techniques can allow the expansion or augmentation of microphysiological devices with additional virtual tissues in order to permit a full body-on-a-chip analysis for every real tissue in culture (e.g., by simulating all other tissues or organs in a full-body model).

In certain embodiments, the disclosed virtual tissue system can statistically model real microphysiological devices based on measured sensor or imaging data in real-time as they are running. In certain embodiments, the virtual tissue system can use said measured sensor or imaging data to display predictive extrapolations of their behavior to users. In certain embodiments, when local microphysiological devices are engaged in digital fluid teleportation connections to off-site microphysiological devices in multi-facility collaborations, continuous statistical modeling, and machine learning algorithms can be used to provide transient virtual tissues as stand-ins during temporary dropouts of a data connection.

In certain embodiments, the method for predicting a biological behavior of a target tissue or a target multi-tissue interaction using a virtual tissue can further comprise coupling the virtual tissue to a microphysiological device by delivering the composition of the virtual tissue's output solution as a synthesized fluidic solution to the microphysiological device. In certain embodiments, a measured partial or full composition of fluid outflowing from a microphysiological device can be used as the data input to a virtual tissue. In non-limiting embodiments, at least one virtual tissue can be coupled with at least one microphysiological device by delivering the synthesized fluidic solution to the at least one microphysiological device through a fluid addressing system. In some embodiments, the method can further include creating a mixed network of microphysiological devices and virtual tissues by the coupling at least one virtual tissue with at least one microphysiological device. For example, multiple virtual tissues and/or multiple real tissues in microphysiological devices within a microphysiological system can be coupled by digital fluid teleportation, where "fluid" teleported to or from the virtual tissue is processed solely as a digital signal (as a result of there being no physical tissue at which a fluid analog can be delivered for interaction). When multiple varieties of tissue cultures in a microphysiological platform can be characterized to the same extent, multiple virtual tissues and/or multiple real tissue units can be coupled in the same manner previously described for systems comprising solely physical ("real") microphysiological device cultures.

Figure 19A:
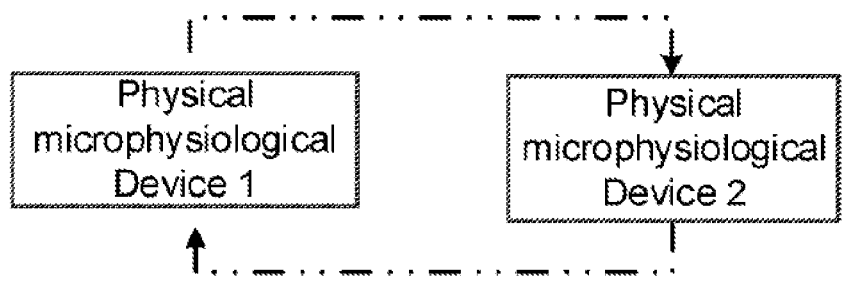
FIG. 19A is an illustration of an exemplary coupling of a microphysiological device—containing a fluidic synthesizer, a biological culture chamber, and a biosensor—with another microphysiological device.
Figure 19B:
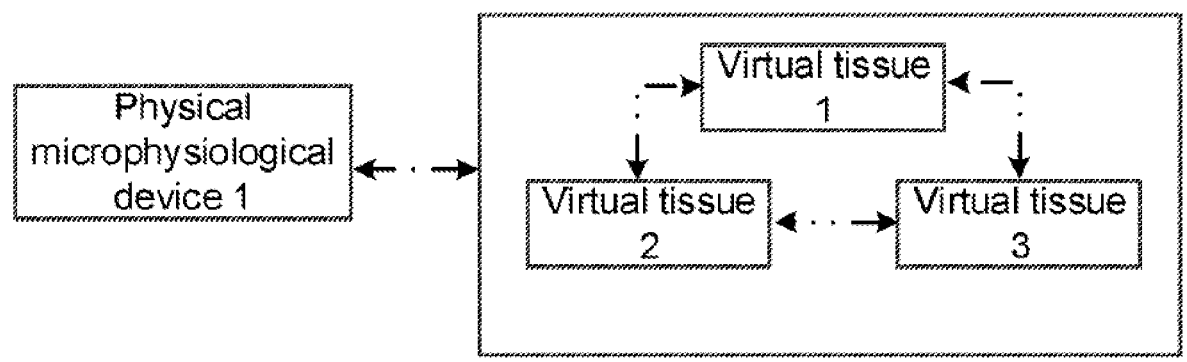
FIG. 19B is an illustration of an exemplary coupling of a single microphysiological device to a dynamic system of multiple virtual tissues, using an exemplary embodiment of digital fluid teleportation as an interconnect in accordance with the present disclosure.
Figure 19C:
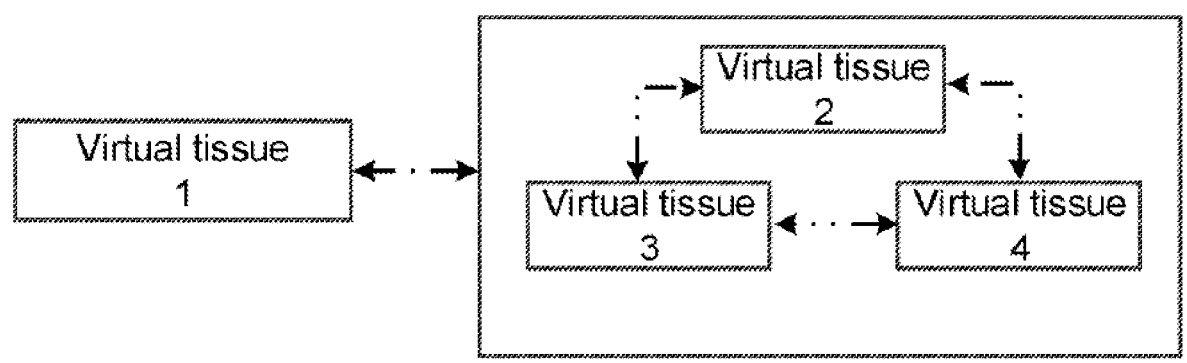
FIG. 19C is an illustration of an exemplary interface of multiple virtual tissues together by an exemplary usage of digital fluid teleportation to form a fully virtual, according to various embodiments.

FIG. 19A illustrates an exemplary coupling of physical microphysiological devices via digital transmission. FIG. 19B depicts an exemplary coupling of a single physical microphysiological device to a dynamic system of multiple virtual tissues. The virtual tissue can receive the digitally transduced contents of fluid effluent from the real microphysiological device, and process the data according to the characterized behavior of the biological entity that it is virtualizing. Then, the virtual tissue can transmit the corresponding effluent's digital-fluidic output to the fluidic synthesizer of the real tissue, where it can be reconstituted into a physical mixture. In non-limiting embodiments, as shown in FIG. 19C, a fully virtual system can be established by interfacing two or more virtual tissues together. In certain embodiments, the screen-forward and screen-backward operational modes can be used for virtual tissue models to substitute certain physical models in the disclosed system. In certain embodiments, a screen-forward or screen-backward approach consisting exclusively of virtual tissues can be used to identify the most promising conditions or predicted outcomes of a set of experiments. In certain embodiments, said identified predictions can be used to select physical experiments to be conducted on real microphysiological devices.

In certain embodiments, the method for predicting a biological behavior of a target tissue using a virtual tissue can further include generating behavioral data or observational data from the at least one microphysiological device. The behavioral or observational data can be used for improving the statistical predictive modeling. In non-limiting embodiments, the target tissue can be incubated with the at least one microphysiological device in a predetermined condition to provide the behavioral or observational data for improving the statistical predictive model. In some embodiments, at least one component of behavioral or observational data can be provided to train the statistical predictive model. In certain embodiments, at least one virtual tissue can be used for predicting the biological behavior of the target tissue.

In certain embodiments, the feedback data can be obtained using the disclosed biosensors (e.g., the biosensors 140, as described above with reference to FIG. 1). In some embodiments, the biosensors can be integrated on-chip (i.e., on a substrate, such as substrate 101, as described above with reference to FIG. 1). In some embodiments, the biosensors can be detachable. For example, the disclosed system can fully function without biosensors. An exemplary system that does not possess any biosensors can still utilize the fluidic synthesizer to formulate, in real-time, a fluid or a fluid mixture from one or more fluid reagents connected to the system. For example, there can be multiple precursor fluid inlet connections from which a composite solution can be formulated. The quantity of the connections can be expanded based on necessity. An exemplary system without biosensors can deliver this fluid formulation to a target culture chamber by utilizing the fluid addressing system to select the target chamber as the intended destination for the fluid. The fluidic synthesizer can modify the composition of this fluid in real-time to create a dynamic fluid formulation. In some embodiments, output data from the devices can be delivered to a sensor external to the substrate (e.g., an "off-chip" sensor). In some embodiments, the output data can be sent to a vial effluent line and/or a fluid handling system to sample fluid downstream of the devices and deliver the fluid to the biosensor.

In certain embodiments, an exemplary system without integrated biosensors can generate microliter quantities of a specified fluidic mixture to perform conditional or combinatorial screening on selected culture chambers. Instead of using an integrated biosensor, an effluent fluid can be sampled from the system's outlet ports, and the endpoints used to quantify the results of the screened conditions can be measured from the sampled fluid. For example, the endpoints measurements can include measurements of biochemical secretion, metabolism, biochemical processes, brightfield imaging of the contents of the culture chambers, fluorescent imaging of the contents of the culture chambers, electrophysiological measurements (e.g., transepithelial electrical resistance (TEER) measurements), genomic/transcriptomic/proteomic quantification of the cells or subsets of cells in the culture chambers, retrieval of the cells for subsequent processing (e.g., paraffin sectioning or processing for electron microscopy), or a combination thereof.

In certain embodiments, an exemplary system without biosensors can record a fluidic composition on an external biosensor platform and digitally teleport the recorded fluidic composition to a fluidic synthesizer. For purposes of illustration and not limitation, the secretions of tissue can be sampled into multiple discrete collections over the course of a time series, and the concentrations of the secretions can be measured using conventional assay techniques (e.g., by ELISA). Following the measurement of these samples, the resultant concentration profile can be used as a fluidic composition, and thus such a recording can be replicated through at least one fluidic synthesizer, which can be located remotely from each other. In non-limiting embodiments, the sampled fluidic composition can be modified and teleported to a fluidic synthesizer. As a nonlimiting example, the concentration of the teleported fluidic composition can be modified from the concentration measured in the fluidic recording.

In certain embodiments, an exemplary system without biosensors can perform the screen-forward and/or screen-backward screenings. The initial conditions (whether fixed in screen-forward or heuristically/iteratively generated in screen-backward approaches) can be formulated by the fluidic synthesizer and do not require sensor feedback. Similarly, the endpoints for either mode can be chosen such that quantification can be produced off-chip. In non-limiting embodiments, the biosensors can be integrated into the disclosed system for collecting more data related to biological characterization and/or strengthening of associated virtual tissue models.

In certain embodiments, the virtual tissue can reduce the physical complexity of the microphysiological platform (relative to the use of an equivalent real/physical model) in exchange for increased computational complexity. By incorporating virtual tissues as substitutes for microphysiological devices, a scientific experiment or investigation conducted with the subject matter can be less expensive and time-consuming. For example, the virtual tissues can be free from biological contamination risks, and the virtual tissues do not require biological supplementation with culture media or growth factors. Furthermore, statistical models of virtual tissues can be deterministically repeatable. In some embodiments, the virtual tissue can operate in a training mode. In such a training mode, the microphysiological platform can utilize physical microphysiological devices to challenge one or more tissues in real-time as dictated by the statistical uncertainty of the virtual tissue, with the goal being to improve the predictive efficacy of the virtual tissue in regimes or circumstances where its existing predictive capacity is weakest or most prone to error In certain embodiments, these regimes or circumstances can include without limitation a set of multiple previously-unencountered fluid compositions in order to measure the response of the real tissues and thereby populate any lacking areas of its statistical observation space. The disclosed training mode can subject real tissues to edge cases and contrive useful circumstances in order to strengthen the virtual model through machine learning approaches. The disclosed training mode can ensure that the virtual tissue does not interpolate too far from physically derived data during real experiments, so as to maximize its predictive power and minimize error.

In certain embodiments, an experiment conducted by the disclosed subject matter can consist entirely of virtual tissues for predictive modeling. As a nonlimiting example, the application of the disclosed biological virtualization can be used for both screen-forward and screen-backward computational solvers. In certain embodiments, the disclosed virtual tissue system can answer exemplary predictive questions including without limitation: "given these initial conditions, what tissue dynamics can be predicted to be observed over four weeks?" or "given these desired dynamical properties of a tissue, what formulation of initial conditions can be predicted to produce said properties?" In certain embodiments, the disclosed computational technology can be utilized in pharmaceutical development for both drug candidate screening (forward-computation of drug effects, as a nonlimiting example, "how will the influence of this drug change tissue behavior?") as well as drug candidate identification (back-computation of desired drug targets, as a nonlimiting example, "given that a progression to a healthy state over four weeks is dependent on these initial computed changes in cell behavior, what type of drug would cause these changes?").

In certain embodiments, the disclosed subject matter provides a browsable virtual tissue library which can be accessible from the user software client during configuration. The virtual tissue library can provide access to various virtual tissue modules. Furthermore, the virtual tissue library can offer an interface to real tissues that can be cultured in microphysiological devices, which can be seeded and cultured at a central location and interfaced with a client's local tissue culture by off-site fluidic teleportation with client-configurable seeding dates. Accordingly, the virtual library can be a cheaper alternative to a user than continuously incubating their own large library of cells or tissues in tissue cultures and managing the cost of flasks, growth media, cell-line orders, and so forth.

In certain embodiments, the disclosed subject matter provides methods for connecting a microphysiological device to a virtual tissue. An example method can include characterizing a fluidic solution by measuring a concentration of at least one target analyte with a sensor at a microphysiological device, generating an input to the virtual tissue based on the measurement, and providing the input to the virtual tissue.

Tissue Culturing Use Cases

In certain embodiments, the disclosed subject matter can provide a system for creating large quantities of functional tissues. Microphysiological platforms (e.g., microphysiological platform 100, as described above with reference to FIG. 1) described herein can be used for therapeutic tissue engineering by creating targeted quantities of tissue for transplantation. Microphysiological platforms can create the tissues at a scale that produces sufficient tissue mass for culturing functional tissues. For example, a fluidic synthesizer (e.g., the fluidic synthesizer 110, as described above with reference to FIG. 1) can control the biochemical environment of multiple devices (e.g., tissue culture chambers) producing tissues with low morphological variability. Fluid addressing systems (e.g., fluid addressing systems 120, as described above with reference to FIG. 1) can utilize fluid inputs to support a large quantity of microphysiological devices (e.g., hundreds, thousands, or more) at consistent flow rates, for consistent flow durations, and with consistent fluid composition. Microphysiological platforms described herein can allow functional tissues to be cultured at an improved scale relative to traditional tissue culture methods involving manual pipetting or deployment of tissue culture in the limited footprints of well plate systems.

In certain embodiments, the disclosed subject matter can provide a system for differentiating and maturing tissues. For example, a microphysiological platform can be formulated such that the entire differentiation process of organoid tissues can be automated by the fluidic synthesizer and fluid addressing system. The fluidic synthesizer and fluid addressing system can produce and deliver the required solutions for differentiation to the target devices. The required solutions can be a biological growth medium that can include various compounds for tissue differentiation (e.g., growth factors, transcription inhibitors, and/or nutrients). In non-limiting embodiments, the disclosed screen-forward and screen-backward operational modes can be used to optimize organoid growth, differentiation, and biological function. In some embodiments, the integrated biosensors (e.g., the biosensors 140, as described above with reference to FIG. 1) can provide continuous feedback regarding the state of the organoid. The integrated biosensors can allow a feedback-based differentiation protocol that can dynamically modify the culturing conditions. In some embodiments, the disclosed system also can provide a fixed condition for developing organoid tissues.

Other Use Case

In certain embodiments, the disclosed system can be used to evaluate the effects of genetic modifications on tissues. As a nonlimiting example, the fluidic synthesizer and the fluid addressing system can be used to produce a culture medium with agents that can modify, introduce, or knock out certain genes of cells. The gene editing agents can include various components that can be used in various gene-editing techniques (e.g., CRISPR-Cas9, TALEN, Meganucleases, Zinc finger, and/or gene therapies). In non-limiting embodiments, the disclosed system can be used to assay the effects of genetic modifications at the tissue scale. In certain embodiments, the disclosed system can deliver agents that can perform genetic modification to a targeted subset or subpopulation of cells. The integrated biosensors can monitor the status of the tissues and provide feedback in real-time.

In certain embodiments, the disclosed system can be used to deliver cells or bacteria to the tissues in culture chambers. The fluidic synthesizer can add living entities to the fluid mixture, which can be delivered by the fluid addressing system. The disclosed system with living entities in the fluid mixture can be used to screen biological tissues. For example, the effect of bacterial infection on lung tissues can be screened by delivering one or multiple types of bacteria to one or more target tissues cultured within the device. In non-limiting embodiments, the disclosed system can be used to screen immunotherapies. As a nonlimiting example, certain modified human cells including T-cells augmented with a chimeric antigen receptor (i.e., CAR-T cells) can flow to one or more tissues in culture chambers on the device. Binding efficacy of different CAR-T cells to certain tissues, cancers, cells, drugs, and/or living entities can be assessed. In some embodiments, certain cancer tissues can be cultured in the microphysiological devices, and immunotherapies including CAR-T cell therapies can be screened for efficacy in targeting the cancer tissues, using either the screen-forward or screen-backward operational modes.

In certain embodiments, the disclosed system can deliver viruses to the tissues cultured therein in microphysiological devices. The fluidic synthesizer can add certain viruses to the fluid mixture, which can be delivered by the fluid addressing system. The disclosed system with certain viruses can be used to assay the susceptibility of the cultured tissues to the viruses. In non-limiting embodiments, the system can include vaccines and be used to assay the efficacy of vaccines or other preventative agents against viral infection.

In certain embodiments, the disclosed system can deliver certain gases to cultured tissues in microphysiological devices through the fluid addressing system. The disclosed system with gases delivered to the tissues can be used to model embolism and/or human airway tissues. In non-limiting embodiments, certain gases can be included in a fluid mixture and be delivered to one or more microphysiological devices. In some embodiments, gas compositions can be designed to mimic hypoxic or hyperoxic conditions. In certain embodiments, a lung model can be subjected to hypoxic hyperoxic conditions, and its resultant behavior can be examined by the disclosed system. In non-limiting embodiments, certain toxic gases can be delivered to tissues cultured in the culture chambers for assessing their effects on, or damage to, the tissue.

The disclosed subject matter provides systems and methods for physically modeling, computationally modeling, or a combination thereof to form a microphysiological platform. The multiple microphysiological devices can be interconnected. In certain embodiments, the biological tissues, organisms, or systems being interconnected can span numerous scales of biological and population-level entities. For example, the multiple interconnected biological tissues or systems can model the interaction of different cell types, different biological organs, different biological organisms (e.g., to model disease transmission between two humans), different species (e.g., to model infection of human tissue by a culture of bacteria); different biological scales (e.g., to model effects of metabolite secretion from a culture of one cell type on cultures of tissues from a population of human donors) or combinations thereof.

In certain embodiments, the disclosed microphysiological devices can be spatially patterned to connect to at least one microfluidic channel or fluidic connection to form a microphysiological platform or a subset of a microphysiological platform. In certain embodiments, the at least one microfluidic channels can be used to deliver fluids to at least one microphysiological device spatially patterned within said microfluidic channel or microfluidic channel network. For example, the fluids can include cell culture media, nutrients, glucose, amino acids, biological therapeutics, drugs, drug products, toxins, gases, dissolved solids, dissolved chemical compounds, aerosolized compounds, biologically acting chemical fixatives, or combinations thereof. In non-limiting embodiments, the fluids can be delivered in a plurality of discrete periods. In certain embodiments, the fluids in a predetermined range of doses can be delivered doses to the microphysiological device. In certain alternative embodiments, the fluids can be delivered continuously to the microphysiological device.

In certain embodiments, chemical compositions of a fluid delivered to the microphysiological platform can require a modification. The modification can be made based on biological experimentation (e.g., to maintain homeostasis, or in response to sensor readings). In certain embodiments, the modification to the fluid's chemical composition can be dynamic and continuous. In non-limiting embodiments, the modification can be discrete or can be performed stepwise.

In certain embodiments, the disclosed fluidic synthesizer can be included in a microphysiological platform to synthesize fluid of a desired chemical composition. The desired chemical composition can be synthesized by mixing or combining a predetermined concentration of discrete ingredients, partitioned fluids, inlet solutions, reagents, or a combination thereof corresponding to the desired composition. In non-limiting embodiments, the synthesized fluid mixture can be delivered to a plurality of microphysiological devices/platforms using a delivery mechanism (e.g., a microfluidic channel or a fluid conduit).

The disclosed subject matter provides systems and methods for producing a "body-on-a-chip" system or a system composed of multiple interconnected "organ-on-chip" models using a plurality of microphysiological devices that are not in physical fluid communication or are not physically fluidically accessible. In certain embodiments, digital fluid teleportation can fluidically interconnect microphysiological devices or microphysiological platforms between different laboratories, different institutions, or scientists with different experimental capabilities.

It will be understood that the foregoing is only illustrative of the principles of the present disclosure, and that various modifications can be made by those skilled in the art without departing from the scope and spirit of the present disclosure.

What is claimed is:

1. A microphysiological platform, comprising:
   a fluidic synthesizer having a first fluid input selectively coupleable to a source of a first input fluid solution and a second fluid input selectively coupleable to a source of a second input fluid solution, and a fluid output, the fluidic synthesizer operable to create an output solution by mixing first input fluid solution received from the first fluid input and second input fluid solution received from the second fluid input and to discharge the output solution from the fluid output;
   a fluid addressing system having a fluid input fluidically coupled to the fluidic synthesizer fluid output, a first fluid output and a second fluid output, the fluid addressing system operable to convey output solution from the fluid addressing system fluid input to a selected one, or both, of the first fluid output and the second fluid output; and
   a first microphysiological device having a fluid input fluidically coupled to the first fluid output of the fluid addressing system and a second microphysiological device having a fluid input fluidically coupled to the second fluid output of the fluid addressing system, each of the first microphysiological device and the second microphysiological device configured to culture biological tissue and to perfuse the biological tissue with the output solution from the fluidic synthesizer received at the fluid input of the respective microphysiological device via the fluid addressing system.

2. The microphysiological platform of claim 1, wherein the fluidic synthesizer has at least a third fluid input selectively coupleable to at least a source of at least a third input fluid solution and is further operable to create the output solution by mixing one or both of the first input fluid solution received from the first fluid input and the second input fluid solution received from the second fluid input with the at least a third input fluid solution received at the at least a third fluid input.

3. The microphysiological platform of claim 1, wherein the fluidic synthesizer includes a mixing chamber fluidically coupled to the fluid inputs and to the fluid output of the fluidic synthesizer and configured to mix the input fluid solutions to create the output solution.

4. The microphysiological platform of claim 1, wherein the fluidic synthesizer for each fluid input includes a valve fluidically coupled to the fluid input, and a control input coupled to each valve operable to selectively open or close the valve to selectively permit or prevent the fluid of the respective input fluid solution from the respective fluid input to the fluid output of the fluidic synthesizer.

5. The microphysiological platform of claim 1, wherein the first microphysiological device includes a fluid channel fluidically coupled to the fluid input of the first microphysiological device and a tissue chamber fluidically coupled to the fluid channel.

6. The microphysiological platform of claim 5, wherein the first microphysiological device includes a fluid output fluidically coupled to the fluid channel of the first microphysiological device and is configured to discharge an output solution.

7. The microphysiological platform of claim 6, further comprising a biological tissue disposed in the tissue chamber of the first microphysiological device, wherein the output solution has a composition that is affected by interaction of the output solution of the fluidic synthesizer received in the fluid channel via the fluid addressing system and the biological tissue.

8. The microphysiological platform of claim 7, wherein the biological tissue includes one or more of a lung tissue, a bone marrow tissue, a bone tissue, a pancreatic tissue, an endocrine islet tissue, a liver tissue, a kidney tissue, a placenta tissue, an eye tissue, an intestinal tissue, a bladder tissue, a brain tissue, a mouth tissue, a tongue tissue, a tooth tissue, a nose tissue, a thymus tissue, a lymph node tissue, a lymphatic system tissue, a throat tissue, a specific human tissue, a specific human tissue undergoing a specific routine behavior, a lung tissue that is cyclically breathing, a specific human tissue undergoing an atypical condition, a lung tissue undergoing an asthma attack, a specific human tissue undergoing a specific interaction with an outside agent, a lung tissue being infected with bacteria, a lung tissue exposed to environmental factors, a lung tissue exposed to pollution, a lung tissue exposed to corrosive gas, a specific human tissue undergoing a specific interaction with an outside agent that is intended for use as a therapeutic, a specific human tissue undergoing a specific interaction with a drug, a specific human tissue undergoing a specific interaction with a biological antibody, a specific human tissue undergoing a specific interaction with a cellular therapy, or a lung tissue undergoing an asthma attack while being monitored for its interaction with a bronchodilator as therapy for asthma.

9. The microphysiological platform of claim 7, wherein the tissue chamber of the first microphysiological device includes a tissue chamber fluid input through which the biological tissue can be introduced into the tissue chamber.

10. The microphysiological platform of claim 7, wherein the first microphysiological device is an organ-on-a-chip model.

11. The microphysiological platform of claim 10, wherein the second microphysiological device is an organ-on-a-chip model, different than the organ-on-a-chip model of the first microphysiological device.

12. The microphysiological platform of claim 6, further comprising a biosensor fluidically coupled to the fluid output of the first microphysiological device and configured to detect a target analyte in the output solution discharged from the fluid output of the first first microphysiological device.

13. The microphysiological platform of claim 12, wherein the biosensor includes:
a chemical reaction or bioreaction recognition element configured to interact with the target analyte to produce a measurement of quantity or concentration of the target analyte; and
a recording system configured to record the measurement and an activity of the first microphysiological device.

14. The microphysiological platform of claim 13, further comprising a sensor data transmitter operatively coupled to the biosensor and operable to transmit the measurement to an external data receiver.

15. A microphysiological system including the microphysiological platform according to claim 13 and a control system operatively engageable with the microphysiological platform, the control system including:
the source of the first input fluid solution selectively coupleable to the first fluid input of the fluidic synthesizer and the source of the second input fluid solution selectively coupleable the second fluid input of the fluidic synthesizer, the second input fluid solution including the target analyte;
a fluidic synthesizer controller operably coupleable to the fluidic synthesizer to cause the fluidic synthesizer to create the output solution by including at least the second input fluid solution;
an addressing system controller operably coupleable to the fluid addressing system to cause the fluid addressing system to convey the output solution from the fluid addressing system fluid input to the second fluid output;
a data receiver operable to receive data indicative of a concentration of the target analyte; and
a main controller operable to control the operation of the fluidic synthesizer controller to create the output solution with the target analyte and to control the operation of the addressing system controller to cause the addressing system to convey the output solution with the target analyte to the fluid input of the second microphysiological device, thereby creating a virtual fluidic connection between the fluid output of the first microphysiological device and the second microphysiological device.

16. A microphysiological system including a first microphysiological platform according to claim 13, a second microphysiological platform according to claim 12, and a control system operatively engageable with the first microphysiological platform and the second microphysiological platform, the control system including:
the source of the first input fluid solution selectively coupleable to the first fluid input of the fluidic synthesizer of the second microphysiological platform and the source of the second input fluid solution selectively coupleable the second fluid input of the fluidic synthesizer of the second microphysiological platform, the second input fluid solution including the target analyte;
a fluidic synthesizer controller operably coupleable to the fluidic synthesizer of the second microphysiological platform to cause the fluidic synthesizer of the second microphysiological platform to create the output solution by including at least the second input fluid solution;
an addressing system controller operably coupleable to the fluid addressing system of the second microphysiological platform to cause the fluid addressing system of the second microphysiological platform to convey the output solution from the fluid addressing system input to a selected one, or both, of the first fluid output and the second fluid output;
a data receiver operable to receive data indicative of a concentration of the target analyte detected by the biosensor of the first microphysiological platform in the output solution discharged from the fluid output of the first microphysiological device of the first microphysiological platform; and
a main controller operable to control the operation of the fluidic synthesizer controller of the second microphysiological platform to create the output solution with the target analyte and to control the operation of the addressing system controller to cause the addressing system of the second microphysiological platform to convey the output solution with the target analyte to at least one of the fluid input of the first microphysiological device of the second microphysiological platform and the fluid input of the second microphysiological device of the second microphysiological platform, thereby creating a virtual fluidic connection between the fluid output of the first microphysiological device of the first microphysiological platform and at least one of the first microphysiological device of the second microphysiological platform and the second microphysiological device of the second microphysiological platform.

17. The microphysiological platform of claim 6, further comprising a biosensor selectively fluidically coupleable to the fluid output of the first microphysiological device and to the fluid output of the second microphysiological device and configured to detect a target analyte in the output solution discharged from each of the fluid output of the first microphysiological device and the fluid output of the second microphysiological device.

18. The microphysiological platform of claim 6, further comprising a first biosensor and a second biosensor, each of the biosensors being selectively fluidically coupleable to the fluid output of the first microphysiological device and configured to detect a target analyte in the output solution discharged from the fluid output of the first microphysiological device.

19. The microphysiological platform of claim 1, wherein the fluid addressing system includes a plurality of control lines, each control line operable to control the operation of one or more valves, each valve disposed in a fluidic path between the fluid input of the fluid addressing system and at least one of the first fluid output and second fluid output of the fluid addressing system, the valves collectively operable to permit or prevent output solution from the fluid addressing system fluid input to the selected one, or both, of the first fluid output and the second fluid output.

20. The microphysiological platform of claim 1, wherein the microphysiological platform is implemented on a single substrate.

21. The microphysiological platform of claim 1, further comprising an effluent channel having a fluid output selectively fluidically coupleable to an effluent, the effluent channel also being fluidically coupled, directly or indirectly, to the fluid output of the first microphysiological device and the fluid output of the second microphysiological device.

22. A microphysiological system including the microphysiological platform of claim 1 and a control system operatively engageable with the microphysiological platform, the control system including:
the source of the first input fluid solution selectively coupleable to the first fluid input of the fluidic synthesizer and the source of the second input fluid solution selectively coupleable the second fluid input of the fluidic synthesizer;

a fluidic synthesizer controller operably coupleable to the fluidic synthesizer to cause the fluidic synthesizer to create the output solution by mixing the first input fluid solution and the second input fluid solution; and an addressing system controller operably coupleable to the fluid addressing system to cause the fluid addressing system to convey output solution from the fluid addressing system fluid input to a selected one, or both, of the first fluid output and the second fluid output.

23. The microphysiological system of claim 22, wherein the control system includes an imager operable to collect image information from at least one of the first microphysiological device and the second microphysiological device.

24. The microphysiological system of claim 22, wherein the control system includes a mechanical support selectively engageable with the microphysiological platform to support the microphysiological platform in operative relationship with the sources of input fluid solutions, fluid synthesizer controller, and addressing system controller.

25. The microphysiological system of claim 22, wherein the microphysiological system is operable to perform a screen-forward operation and/or a screen-backward operation.

26. The microphysiological system of claim 22, wherein the control system includes a fluid handler operable to selectively fluidically communicate with one or more of the first microphysiological device, the second microphysiological device, the fluid addressing system, the fluidic synthesizer, and fluidic channels therebetween and to perform one or more of delivering fluid thereto and withdrawing fluid therefrom.

27. A method for fluidic teleportation comprising:
receiving data indicative of a measured concentration of a target analyte in a first fluidic solution at a first location;
providing control instructions to a fluidic synthesizer to cause the fluidic synthesizer to synthesize a second fluidic solution that includes the target analyte at the measured concentration or at a concentration derived from mathematical adjustment or transformation of the measured concentration and that reconstitutes a full or partial composition of the first fluidic solution; and
causing the second fluidic solution to flow to a second location that is fluidically isolated from the first location.

28. A method for predicting a biological behavior of a target tissue using a virtual tissue, comprising:
creating a statistical predictive model of a target tissue based on physical observations of the target tissue; and
applying the statistical predictive model to predict a modification of a first fluidic solution, wherein the modification comprises a chemical or a biological change that is induced when the first fluidic solution is incubated with the target tissue to produce a second fluidic solution, wherein the first fluidic solution is an input of the virtual tissue, and the second fluidic solution is an output of the virtual tissue.

29. A method of connecting a microphysiological device to a simulated virtual tissue, comprising:
characterizing a fluidic solution by measuring a concentration of at least one target analyte with the microphysiological device;
generating an input to the simulated virtual tissue based on the characterization; and
providing the input to the simulated virtual tissue.

* * * * *

UNITED STATES PATENT AND TRADEMARK OFFICE
CERTIFICATE OF CORRECTION

PATENT NO. : 11,732,226 B2
APPLICATION NO. : 18/048987
DATED : August 22, 2023
INVENTOR(S) : Dongeun Huh et al.

It is certified that error appears in the above-identified patent and that said Letters Patent is hereby corrected as shown below:

In the Specification

Under Column No. 2, Line no. 41, Replace:
"control system and"
With:
--control system, and--

Under Column No. 3, Line no. 29, Replace:
"according to an embodiment"
With:
--according to an embodiment.--

Under Column No. 4, Line no. 41, Replace:
"in the arm of"
With:
--in the array of--

Under Column No. 5, Line no. 2, Replace:
"neurophysiological platform"
With:
--microphysiological platform--

Under Column No. 5, Line no. 9, Replace:
"devices 130 in some"
With:
--devices 130. In some--

Under Column No. 5, Line nos. 55-56, Replace:
"or an combination"

Signed and Sealed this
Fourteenth Day of November, 2023

Katherine Kelly Vidal
*Director of the United States Patent and Trademark Office*

With:
--or any combination--

Under Column No. 6, Line no. 28, Replace:
"(e.g. name"
With:
--(e.g., name--

Under Column No. 7, Line nos. 23-24, Replace:
"one or more micro injectors"
With:
--one or more microinjectors--

Under Column No. 7, Line no. 49, Replace:
"devices 130 in"
With:
--devices 130. In--

Under Column No. 8, Line no. 9, Replace:
"110 in some"
With:
--110. In some--

Under Column No. 8, Line no. 11, Replace:
"110 in some"
With:
--110. In some--

Under Column No. 8, Line no. 16, Replace:
"neurophysiological devices"
With:
--microphysiological devices--

Under Column No. 9, Line no. 54, Replace:
"e.g., through"
With:
--e.g. through--

Under Column No. 9, Line no. 57, Replace:
"e.g., through"
With:
--e.g. through--

Under Column No. 10, Line no. 15, Replace:
"read-only memory (ROM)."

With:
--read-only memory (ROM),--

Under Column No. 10, Line no. 38, Replace:
"and magnetic tape,"
With:
--and magnetic tape;--

Under Column No. 10, Line no. 44, Replace:
"signal processing modules, and"
With:
--signal processing modules; and--

Under Column No. 10, Line nos. 47-48, Replace:
"Programmable Logic Devices (PLDs)."
With:
--Programmable Logic Devices (PLDs),--

Under Column No. 11, Line nos. 10-11, Replace:
"multiple bonded lavers,"
With:
--multiple bonded layers,--

Under Column No. 11, Line nos. 13-14, Replace:
"two or more lay ers"
With:
--two or more layers--

Under Column No. 11, Line no. 32, Replace:
"followings, selectively"
With:
--followings: selectively--

Under Column No. 11, Line no. 47, Replace:
"platform 10"
With:
--platform 100--

Under Column No. 12, Line no. 30, Replace:
"solution mixing chamber"
With:
--solution. Mixing chamber--

Under Column No. 12, Line no. 34, Replace:
"component(s), e.g., to"

CERTIFICATE OF CORRECTION (continued)
U.S. Pat. No. 11,732,226 B2

With:
--component(s), e.g. to--

Under Column No. 13, Line no. 16, Replace:
"fluid (e.g., the"
With:
--fluid (e.g. the--

Under Column No. 13, Line no. 21, Replace:
"126A, 126B. 126C. 126D,"
With:
--126A, 126B, 126C, 126D,--

Under Column No. 14, Line no. 15, Replace:
"(e.g., $2^{14}$=16.384"
With:
--(e.g., $2^{14}$=16,384--

Under Column No. 16, Line no. 7, Replace:
"platform 10)."
With:
--platform 100.--

Under Column No. 16, Line no. 17, Replace:
"neurophysiological devices 130"
With:
--microphysiological devices 130--

Under Column No. 16, Line no. 26, Replace:
"by am one or more"
With:
--by any one or more--

Under Column No. 16, Line no. 54, Replace:
"FIGS. 5A-SC"
With:
--FIGS. 5A-5C--

Under Column No. 17, Line nos. 29-30, Replace:
"input A (132-4A)"
With:
--input A (132-1A)--

Under Column No. 17, Line no. 56, Replace:
"with any, tissue"

With:
--with any tissue--

Under Column No. 18, Line no. 16, Replace:
"U.S. Pat Pub."
With:
--U.S. Pat. Pub.--

Under Column No. 18, Line no. 21, Replace:
"WIPO Pub Number"
With:
--WIPO Pub. Number--

Under Column No. 18, Line no. 25, Replace:
"U S. Pat Pub."
With:
--U.S. Pat. Pub.--

Under Column No. 18, Line no. 26, Replace:
"U.S. Pat Pub"
With:
--U.S. Pat. Pub.--

Under Column No. 18, Line no. 33, Replace:
"130, e.g., of the"
With:
--130, e.g. of the--

Under Column No. 18, Line no. 60, Replace:
"or entities: measuring"
With:
--or entities; measuring--

Under Column No. 19, Line no. 13, Replace:
"operatively. e.g.,"
With:
--operatively, e.g.--

Under Column No. 19, Line no. 15, Replace:
"device 13o. The"
With:
--device 130. The--

Under Column No. 20, Line no. 17, Replace:
"magnetic resonance. X-ray"

CERTIFICATE OF CORRECTION (continued)
U.S. Pat. No. 11,732,226 B2

With:
--magnetic resonance, X-ray--

Under Column No. 20, Line no. 31, Replace:
"e.g., as part"
With:
--e.g. as part--

Under Column No. 20, Line no. 47, Replace:
"etc., arrangements,"
With:
--etc. arrangements,--

Under Column No. 21, Line no. 51, Replace:
"(e.g., antibodies. DNA, RNA,"
With:
--(e.g., antibodies, DNA, RNA,--

Under Column No. 22, Line no. 17, Replace:
"glass. Various biosensing"
With:
--glass, various biosensing--

Under Column No. 22, Line no. 60, Replace:
"130, or (6)"
With:
--130; or (6)--

Under Column No. 23, Line no. 43, Replace:
"e.g., on the same"
With:
--e.g. on the same--

Under Column No. 23, Line no. 59, Replace:
"(e.g. wider the"
With:
--(e.g. under the--

Under Column No. 25, Line no. 64, Replace:
""fluidic teleportation.""
With:
--"fluidic teleportation,"--

Under Column No. 26, Line no. 64, Replace:
"coupled b connections"

With:
--coupled by connections--

Under Column No. 32, Line no. 26, Replace:
"method 809) can"
With:
--method 800 can--

Under Column No. 33, Line no. 65, Replace:
"allow charactering"
With:
--allow characterizing--

Under Column No. 35, Line no. 45, Replace:
"device in certain"
With:
--device. In certain--

Under Column No. 37, Line no. 7, Replace:
"more of the following,"
With:
--more of the following:--

Under Column No. 37, Line no. 54, Replace:
"have 124-way/2-position"
With:
--have 12 4-way/2-position--

Under Column No. 39, Line no. 22, Replace:
"C#, P thon,"
With:
--C#, Python,--

Under Column No. 40, Line no. 43, Replace:
"from know-n conditions"
With:
--from known conditions--

Under Column No. 40, Line no. 54, Replace:
"(e.g., power anal sis,"
With:
--(e.g., power analysis,--

Under Column No. 40, Line nos. 55-56, Replace:
"orthogonal experiment design."

With:
--orthogonal experiment design,--

Under Column No. 41, Line no. 11, Replace:
"1007, 1004 and 1009"
With:
--1007, 1008 and 1009--

Under Column No. 41, Line nos. 52-53, Replace:
"combinational analysis,"
With:
--combinatorial analysis,--

Under Column No. 43, Line nos. 16-17, Replace:
"user interface"
With:
--user interface.--

Under Column No. 44, Line no. 3, Replace:
"where "A" is a"
With:
--where "$A_0$" is a--

Under Column No. 44, Line no. 4, Replace:
"accumulation, if"
With:
--accumulation; if--

Under Column No. 44, Line no. 6, Replace:
"concentration of "A" then"
With:
--concentration of "A," then--

Under Column No. 47, Line no. 63, Replace:
"to error In certain"
With:
--to error. In certain--

Under Column No. 49, Line no. 31, Replace:
"Other Use Case"
With:
--Other Use Cases--

Under Column No. 49, Line no. 31, Replace:
"hypoxic hyperoxic"

CERTIFICATE OF CORRECTION (continued)
U.S. Pat. No. 11,732,226 B2

With:
-- hypoxic or hyperoxic --

In the Claims

Under Column No. 52, Claim 12, Line no. 67, Replace:
"the first first microphysiological"
With:
--the first microphysiological--

Under Column No. 53, Claim 15, Line no. 15, Replace:
"claim 13"
With:
--claim 12--

Under Column No. 53, Claim 16, Line no. 45, Replace:
"claim 13,"
With:
--claim 12,--